US012624030B2

(12) United States Patent
Arabeyre et al.

(10) Patent No.: US 12,624,030 B2
(45) Date of Patent: May 12, 2026

(54) 4-AMINO-3-(4-PHENOXYPHENYL)-1,3-DIHYDRO-2H-IMIDAZO[4,5-C]PYRIDIN-2-ONE DERIVATIVES AND SALTS THEREOF

(71) Applicant: Principia Biopharma Inc., Morristown, NJ (US)

(72) Inventors: Catherine Arabeyre, Prades le Lez (FR); Patricia Moliner, Perols (FR); Sabine Boisnard, Boulogne (FR); Damien Sallaberry, Le Plessis Robinson (FR); Serge Perard, Palaiseau (FR); Sebastien Roy, Sermaise (FR)

(73) Assignee: Principia Biopharma Inc., Morristown, NJ (US)

( * ) Notice: Subject to any disclaimer, the term of this patent is extended or adjusted under 35 U.S.C. 154(b) by 304 days.

(21) Appl. No.: 18/268,577

(22) PCT Filed: Dec. 22, 2021

(86) PCT No.: PCT/US2021/064800

§ 371 (c)(1),
(2) Date: Jun. 20, 2023

(87) PCT Pub. No.: WO2022/140511

PCT Pub. Date: Jun. 30, 2022

(65) Prior Publication Data

US 2024/0051955 A1 Feb. 15, 2024

Related U.S. Application Data

(60) Provisional application No. 63/245,288, filed on Sep. 17, 2021, provisional application No. 63/130,010, filed on Dec. 23, 2020.

(51) Int. Cl.
*C07D 471/04* (2006.01)

(52) U.S. Cl.
CPC .................................. *C07D 471/04* (2013.01)

(58) Field of Classification Search
CPC .................................................... C07D 471/04
USPC ........................................................... 514/303
See application file for complete search history.

(56) References Cited

U.S. PATENT DOCUMENTS

| | | | |
|---|---|---|---|
| 3,760,984 | A | 9/1973 | Theeuwes |
| 3,952,741 | A | 4/1976 | Baker |
| 7,772,226 | B2 | 8/2010 | Yoshikawa et al. |
| 8,557,803 | B2 | 10/2013 | Yamamoto et al. |
| 9,199,997 | B2 | 12/2015 | Yamamoto et al. |
| 9,688,676 | B2 | 6/2017 | Owens |
| 9,695,164 | B2 | 7/2017 | Zhu et al. |
| 11,969,418 | B2 | 4/2024 | Cho et al. |
| 12,049,463 | B2 | 7/2024 | Chen et al. |
| 2006/0045822 | A1 | 3/2006 | Timmons et al. |
| 2013/0079327 | A1 | 3/2013 | Yamamoto et al. |
| 2013/0197014 | A1 | 8/2013 | Chen et al. |
| 2014/0142099 | A1 | 5/2014 | Owens |
| 2014/0179680 | A1 | 6/2014 | Christopher et al. |
| 2021/0113568 | A1 | 4/2021 | Ariza |
| 2021/0244720 | A1 | 8/2021 | Cho et al. |
| 2022/0389011 | A1 | 12/2022 | Chen et al. |
| 2024/0018142 | A1 | 1/2024 | Sheng et al. |
| 2024/0051955 | A1 | 2/2024 | Arabeyre et al. |
| 2024/0173313 | A1 | 5/2024 | Dukovic et al. |
| 2024/0238267 | A1 | 7/2024 | Calderone et al. |
| 2024/0366585 | A1 | 11/2024 | Cho et al. |
| 2024/0391915 | A1 | 11/2024 | Chen et al. |
| 2025/0034130 | A1 | 1/2025 | Chen et al. |
| 2025/0101021 | A1 | 3/2025 | Bailly et al. |
| 2025/0145618 | A1 | 5/2025 | Owens et al. |
| 2025/0197402 | A1 | 6/2025 | Goldstein et al. |
| 2025/0262193 | A1 | 8/2025 | Syed |
| 2025/0282777 | A1 | 9/2025 | Baltes et al. |
| 2025/0354998 | A1 | 11/2025 | Blazier et al. |
| 2026/0022123 | A1 | 1/2026 | Kane, Jr. et al. |
| 2026/0027100 | A1 | 1/2026 | Turner et al. |
| 2026/0060974 | A1 | 3/2026 | Dukovic et al. |

FOREIGN PATENT DOCUMENTS

| | | | |
|---|---|---|---|
| AU | 2022290946 | A1 | 1/2024 |
| CA | 2975072 | A1 | 8/2016 |
| CN | 101610676 | A | 12/2009 |
| CN | 103502249 | A | 1/2014 |
| CN | 104640861 | A | 5/2015 |
| CN | 105753863 | A | 7/2016 |
| EA | 020001 | B1 | 7/2014 |
| EP | 2578585 | A1 | 4/2013 |
| EP | 2786996 | A1 | 10/2014 |
| EP | 4328226 | A1 | 2/2024 |
| EP | 4342468 | A1 | 3/2024 |

(Continued)

OTHER PUBLICATIONS

Core Study Information and Informed Consent Form for Clinical Trial Identifier No. DRI15928, marked "Property of the Sanofi Group—strictly confidential" and dated Feb. 12, 2019.

Core Study Information and Informed Consent Form for Clinical Trial Identifier No. DRI15928, marked "Property of the Sanofi Group—strictly confidential" and dated Oct. 22, 2018 (18 pages).

Core Study Information and Informed Consent Form for Clinical Trial Identifier No. EFC16033, marked "Property of the Sanofi Group—strictly confidential" and dated, Jul. 6, 2023 (20 pages).

Core Study Information and Informed Consent Form for Clinical Trial Identifier No. EFC16034, marked "Property of the Sanofi Group—strictly confidential" and dated Feb. 27, 2023 (20 pages).

Core Study Information and Informed Consent Form for Clinical Trial Identifier No. EFC16035, marked "Property of the Sanofi Group—strictly confidential" and dated Feb. 27, 2023 (21 pages).

(Continued)

*Primary Examiner* — Niloofar Rahmani
(74) *Attorney, Agent, or Firm* — McNeill PLLC

(57) ABSTRACT

The present disclosure relates to 4-amino-3-(4-phenoxyphenyl)-1,3-dihydro-2H-imidazo[4,5-c]pyridin-2-one variants or derivatives, and salts thereof, for use as agonists and antagonists. The disclosure further relates to compositions, methods of preparing, and methods of treatment.

29 Claims, No Drawings

(56) References Cited

FOREIGN PATENT DOCUMENTS

| | | | |
|---|---|---|---|
| JP | 2010504324 | A | 2/2010 |
| JP | 2012246314 | A | 12/2012 |
| JP | 2013507448 | A | 3/2013 |
| JP | 2014517838 | A | 7/2014 |
| JP | 2016504277 | A | 2/2016 |
| JP | 2016094368 | A | 5/2016 |
| JP | 2018516935 | A | 6/2018 |
| JP | 2024544724 | A | 12/2024 |
| RU | 204139111 | A | 8/2005 |
| WO | 2003037890 | A2 | 5/2003 |
| WO | 2006031878 | A2 | 3/2006 |
| WO | 2006086634 | A2 | 8/2006 |
| WO | 2007142755 | A2 | 12/2007 |
| WO | 2008039218 | A2 | 4/2008 |
| WO | 2009010491 | A1 | 1/2009 |
| WO | 2010034796 | A1 | 4/2010 |
| WO | 2011046964 | A2 | 4/2011 |
| WO | 2011152351 | A1 | 12/2011 |
| WO | 2012158764 | A1 | 11/2012 |
| WO | 2012158785 | A1 | 11/2012 |
| WO | 2012170976 | A2 | 12/2012 |
| WO | 2013116382 | A1 | 8/2013 |
| WO | 2013184572 | A1 | 12/2013 |
| WO | 2013184757 | A1 | 12/2013 |
| WO | 2013191965 | A1 | 12/2013 |
| WO | 2014039899 | A1 | 3/2014 |
| WO | 2014078578 | A1 | 5/2014 |
| WO | 2014100620 | A2 | 6/2014 |
| WO | 2015132799 | A2 | 9/2015 |
| WO | 2016057500 | A1 | 4/2016 |
| WO | 2016089722 | A1 | 6/2016 |
| WO | 2016121777 | A1 | 8/2016 |
| WO | 2016/196840 | * | 12/2016 |
| WO | 2016196840 | A1 | 12/2016 |
| WO | 2017041536 | A1 | 3/2017 |
| WO | 2017066014 | A1 | 4/2017 |
| WO | 2017087445 | A1 | 5/2017 |
| WO | 2018096141 | A1 | 5/2018 |
| WO | 2021150476 | A1 | 7/2021 |
| WO | 2021247748 | A1 | 12/2021 |
| WO | 2022081512 | A1 | 4/2022 |
| WO | 2022140511 | A1 | 6/2022 |
| WO | 20220121670 | A1 | 6/2022 |
| WO | 2022223027 | A1 | 10/2022 |
| WO | 2022242740 | A1 | 11/2022 |
| WO | 2022257845 | A1 | 12/2022 |
| WO | 2023031840 | A1 | 3/2023 |
| WO | 2023122072 | A1 | 6/2023 |
| WO | 2023220370 | A1 | 11/2023 |
| WO | 2023244587 | A1 | 12/2023 |
| WO | 2023249980 | A1 | 12/2023 |
| WO | 2024006406 | A1 | 1/2024 |
| WO | 2024081168 | A1 | 4/2024 |
| WO | 2024137604 | A1 | 6/2024 |
| WO | 2024163542 | A2 | 8/2024 |
| WO | 2025188862 | A1 | 9/2025 |
| WO | 2026050513 | A1 | 3/2026 |

OTHER PUBLICATIONS

Core Study Information and Informed Consent Form for Clinical Trial Identifier No. EFC16645, marked "Property of the Sanofi Group—strictly confidential" and dated Feb. 27, 2023 (20 pages).
Core Study Information and Informed Consent Form for Clinical Trial Identifier No. EFC17262, marked "Property of the Sanofi Group—strictly confidential" and dated Sep. 14, 2022 (22 pages).
Core Study Information and Informed Consent Form for Clinical Trial Identifier No. LTS16004, marked "Property of the Sanofi Group—strictly confidential" and dated Jun. 28, 2023 (19 pages).
Core Study Information and Informed Consent Form for Clinical Trial Identifier No. POP16398, marked "Property of the Sanofi Group—strictly confidential" and dated Jun. 16, 2022 (22 pages).
Core Study Information and Informed Consent Form for Clinical Trial Identifier No. POP16399, marked "Property of the Sanofi Group—strictly confidential" and dated May 31, 2022 (22 pages).
Participant Information Sheet and Informed Consent Form for Sponsor Study No. BEX16018, marked "Property of the Sanofi Group—strictly confidential" and dated Aug. 9, 2019 (30 pages).
Aaltonen et al., "Solid form screening—A review", European Journal of Pharmaceutics and Biopharmaceutics, 2009, vol. 71(1), 23-37 (see part 1 Introduction and background (1.1, 1.2) doi:10.1016/j.ejpb.2008.07.014).
Bernstein, J., "Polymorphism of molecular crystals", Moscow, Nauka, Ch. 7.3.2., Bioavailability, pp. 324-330 (2007).
Council for International Organizations of Medical Sciences (CIOMS), "Drug-induced liver injury (DILI): Current status and future directions for drug development and the post-market setting" (2020) (176 pages).
FDA Guidance for Industry Drug-Induced Liver Injury: Premarketing Clinical Evaluation; U.S. Department of Health and Human Services, Food and Drug Administration, Center for Drug Evaluation and Research (CDER), Center for Biologics Evaluation and Research (CBER), Jul. 2009 (28 pages).
Kümmerer, Pharmaceuticals in the environment, Annual Review of Environment and Resources, v. 35, pp. 57-75, doi: 10.1146/annurev-environ-052809-161223 (see the abstract, p. 60) (2010).
Sarma et al., "Solid formation of pharmaceuticals: Polymorphs, salt and cocrystals", Korean J.Chem. Eng., 28(2), pp. 315-322 (p. 315-317 section "Introduction", "Polymorphism") (2011).
Sanofi Press Release, "Patient enrollment of phase III tolebrutinib trials paused in the U.S.", (Jun. 30, 2022) (2 pages).
Giovannoni, Gavin, "Smouldering MS: the real MS becomes a tractable problem", Sep. 2, 2024 (7 pages).
Greenberg, B.M., "Bruton's Tyrosine Kinase Inhibitors for Multiple Sclerosis Treatment: A New Frontier", Neurol Clin, 42, pp. 155-163 (2024).
Gruber et al., "BTK regulates microglial function and neuroinflammation in human stem cell models and mouse models of multiple sclerosis", Nature Communications, 115:10116 (2024) (17 pages).
Gruber et al., "Central Effects of BTK Inhibition in Neuroinflammation (808)", Neurology, Multiple Sclerosis: Basic Science, 94(15_Supplement), Apr. 14, 2020 (2 pages).
Gruber et al., "Central Effects of BTK Inhibition in Neuroinflammation", AAN, Presentation 808, 2020 (12 pages).
Gruber et al., "Decoding Bruton's Tyrosine Kinase Signaling in Neuroinflammation", ECTRIMS-ACTRIMS 2020, P0311 (10 pages).
Gruber et al., "Decoding bruton's tyrosine kinase signalling in neuroinflammation", P0311, Multiple Sclerosis Journal, 26: (S3), p. 270 (2020).
Gruber et al., "Establishing a Role for the Bruton's Tyrosine Kinase Inhibitor Tolebrutinib in Modulating Neuroinflammation and Disease Progression in MS", AAN 2021, Platform S25:003 (13 pages).
Gruber et al., Establishing a Role for the Bruton's Tyrosine Kinase Inhibitor Tolebrutinib in Modulating Neuroinflammation and Disease Progression in MS (1974), Neurology, MS and CNS Inflammatory Disease: Emerging Therapeutics and Biomarkers, 96 (15_supplement) (Apr. 13, 2021).
Gruber et al., "Evaluating the effect of a Bruton's tyrosine kinase inhibitor in a murine experimental autoimmune encephalomyelitis model of multiple sclerosis", P174, Multiple Sclerosis Journal, 28: (3S), pp. 244-245 (2022).
Gruber et al., "Evaluating the Effect of a Bruton's Tyrosine Kinase Inhibitor in a Murine Experimental Autoimmune Encephalomyelitis Model of Multiple Sclerosis", P174, Presented at the 38th Congress of the European Committee for Treatment and Research in Multiple Sclerosis (ECTRIMS); Amsterdam, the Netherlands; Oct. 26-28, 2022 (1 page).
Gruber et al., "Evaluating the effect of BTK inhibitor tolebrutinib in human microglia", P391, Multiple Sclerosis Journal, 27: (2S), pp. 376-377 (2021).
Gruber et al., "Evaluating the Effect of BTK Inhibitor Tolebrutinib in Human Microglia", P391, Presented at the 37th Congress of the European Committee for Treatment and Research in Multiple Sclerosis, Oct. 13-15, 2021, Virtual (1 page).

(56) References Cited

OTHER PUBLICATIONS

Gruber et al., "Evaluating the Effect of BTK Inhibitor Tolebrutinib in Human Tri-cultre", Presented at the American Academy of Neurology (AAN) Virtual Annual Meeting, 2594, Apr. 24-26, 2022 (1 page).
Gruber et al., "Evaluating the Effect of BTK Inhibitor Tolebrutinib in Human Tri-culture (P1-1.Virtual)", 2594, Neurology, MS and CNS Inflammatory Disease Virtual, 98(18_supplement), (May 3, 2022) (2 pages).
Gruber et al., "Evaluating the Effect of BTK Inhibitor Tolebrutinib in Modulating Microglia-Driven Neuroinflammation and MS Progression", EPR-182, European Journal of Neurology, 28 (Suppl. 1), p. 327 (2017).
Gruber et al., "Evaluating the Effect of BTK Inhibitor Tolebrutinib in Modulating Microglia-Driven Neuroinflammation and MS Progression", EAN 2021, EPR-182 (8 pages).
Guerra et al., "Cerebrospinal fluid proteomic dissection of chronic neuroinflammation in Multiple Sclerosis patients", National Institutes of Health National Institute of Neurological Disorders and Stroke, ACTRIMS, P362 (1 page) (2025).
Guerra et al., "Cerebrospinal Fluid Proteomic Dissection of Chronic Neuroinflammation in Multiple Sclerosis", P362, Multiple Sclerosis Journal, 31: (2S), pp. 194-195 (2025).
Hegen et al., "Recent developments in MOG-IgG associated neurological disorder", Ther Adv Neurol Disord, vol. 13, pp. 1-20 (2020).
Hilfiker et al., "Relevance of Solid-state Properties for Pharmaceutical Products", Polymorphism in the Pharmaceutical Industry, Wiley-VCL, XP002528052, pp. 1-19 (Jan. 1, 2006).
International Search Report and Written Opinion of the International Searching Authority issued in International Application No. PCT/US2023/025170 on Sep. 29, 2023 (10 pages).
International Search Report and Written Opinion of the International Searching Authority issued in International Application No. PCT/US2025/018520 on Jul. 28, 2025 (15 pages).
Kappos et al., "Contribution of Relapse-Independent Progression vs Relapse-AssociatedWorsening to Overall ConfirmedDisability Accumulation in Typical Relapsing Multiple Sclerosis in a Pooled Analysis of 2 Randomized Clinical Trials", JAMA Neurol., 77(9), pp. 1132-1140, Published online Jun. 8, 2020.
Kappos et al., "Efficacy of Siponimod in Secondary Progressive Multiple Sclerosis: Results of the Phase 3 Study (CT.002)", Neurology, Clinical Trials, 88(16_supplement) (Apr. 18, 2017) (5 pages).
Kappos et al., "Ponesimod compared with teriflunomide in patients with relapsing multiple sclerosis in the active-comparator phase 3 OPTIMUM Study", JAMA Neurol. Published online Mar. 29, 2021 (32 pages).
Kramer et al., "Bruton tyrosine kinase inhibitors for multiple sclerosis", Nature Reviews Neurology, 19, pp. 289-304 (May 2023).
Lindsey Shapiro, PhD, "Target smoldering inflammation. Data from Phase 3 trials show therapy slows disability progression in MS", Presented at EuropeanCommittee for Treatment and Research in Multiple Sclerosis (ECTRIMS) annual meeting, Sep. 18-20, 2024, online and in-person in Copenhagen (9 pages).
Lublin et al., "Defining the clinical course of multiple sclerosis: Results of an international survey", Neurology, 46, pp. 907-911 (1996).
Martin et al., "Bruton's Tyrosine Kinase Inhibition Promotes Myelin Repair", Brain Plasticity 5, pp. 123-133 (2020).
Meglio, Marco, "BTK Inhibitor Tolebrutinib Slows Disability Progression in Phase 3 HERCULES Study of Non-Relapsing Secondary Progressive MS", NeurologyLive, MJH Life Sciences, Sep. 3, 2024 (5 pages).
Merck KGaA, Darmstadt, Germany, News Release, "Initiation of New Patients on Evobrutinib Paused in the U.S.; Fully Enrolled Phase III Evobrutinib Studies Continue", Apr. 12, 2023 (2 pages).
Merck KGaA, News Release, "Merck KGaA, Darmstadt, Germany Provides Update on Phase III Results for Evobrutinib in Relapsing Multiple Sclerosis", Darmstadt, Germany, Dec. 5, 2023 (3 pages).
Montalban et al., "Bruton's tyrosine kinase inhibitor evobrutinib (M2951) in patients withrelapsing Multiple sclerosis: a randomised, placebo-controlled, phase 2 study", O1205, European Journal of Neurology, 26 (Suppl. 1), p. 32 (2019).
Montalban et al., "Characterisation of the safety profile of evobrutinib in over 1000 patients from phase II clinical trials in multiple sclerosis, rheumatoid arthritis and systemic lupus erythematosus: an integrated safety analysis", J Neurol Neurosurg Psychiatry; 94:1-9 (2023).
Montalban et al., "Effect of evobrutinib, a Bruton's tyrosine kinase inhibitor, on immune cell and immunoglobulin levels over 48 weeks in a phase 2 study in relapsing multiple sclerosis", P1358, Multiple Sclerosis Journal, 25: (S2), p. 748 (2019).
Montalban et al., "Efficacy and Safety of the Bruton's Tyrosine Kinase Inhibitor Evobrutinib (M2951) in Patients with Relapsing Multiple Sclerosis over 48 Weeks: a Randomized, Placebo-Controlled, Phase 2 Study (S56.004)", Neurology, MS Trials and Treatment, 92(15_supplement) (Apr. 9, 2019) (2 pages).
Montalban et al., "Efficacy and safety results after >3.5 years of treatment with the Bruton's tyrosine kinase inhibitor evobrutinib in relapsing multiple sclerosis: Long-term follow-up of a Phase II randomised clinical trial with a cerebrospinal fluid sub-study", Multiple Sclerosis Journal, vol. 30(4-5), pp. 558-570 (2024).
Montalban et al., "Rationale and Design of two Phase 3 Randomized Controlled Trials (Evolution RMS 1&2) Evaluation the Bruton's Tyrosine Kinase Inhibitor Evobrutinib in Patients with Relapsing Multiple Sclerosis (4071)", Neurology, Multiple Sclerosis: Clinical Trials and Therapeutics 3, 94(15_supplement) Apr. 14, 2020 (3 pages).
Montalban et al., "Safety and efficacy of evobrutinib in relapsing multiple sclerosis (evolutionRMS1 and evolutionRMS2): two multicentre, randomised, double-blind, active-controlled, phase 3 trials", Lancet Neurol, 23: 1119-1132 (2024).
Multiple Sclerosis Trust, "Tolebrutinib. Other names: SAR442168, PRN2246", Last Updated Sep. 5, 2024 (8 pages).
NHS Oxford University Hospitals, "MOG Antibody Demyelination. Information for patients", Apr. 2019 (12 pages).
Nicolas et al., "Absorption, Metabolism, and Excretion of [14C]-Tolebrutinib After Oral Administration in Humans, Contribution of the Metabolites to Pharmacological Activity", Clinical Drug Investigation, 43, pp. 653-665 (2023).
Nicolas et al., "Tolebrutinib Demonstrates Cerebrospinal Fluid Exposure at Bioactive Levels in a Single-Ascending Dose Study in Healthy Volunteers", P151, Presented at the 8th Annual Americas Committee for Treatment and Research in Multiple Sclerosis (ACTRIMS) Forum; San Diego, CA, USA; Feb. 23-25, 2023 (1 page).
Nicolas et al., "Tolebrutinib Demonstrates Cerebrospinal Fluid Exposure at Bioactive Levels in a Single-Ascending Dose Study in Healthy Volunteers", P151, Multiple Sclerosis Journal, 29:(2S), p. 89 (2023).
Oh et al., "Safety and clinical efficacy outcomes from the Long-term extension study of tolebrutinib in patients with relapsing multiple sclerosis: 2-year results", P308, Multiple Sclerosis Journal, 28: (3S), pp. 342-343 (2022).
Oh et al., "Efficacy and Safety of Tolebrutinib Versus Teriflunomide in Relapsing Multiple Sclerosis: Results From the Phase 3 GEMINI 1 and 2 Trials", ECTRIMS 2024, Presentation #0135, Presented at the 40th Congress of the European Committee for Treatment and Research in Multiple Sclerosis; Sep. 18-20, 2024; Copenhagen, Denmark (16 pages).
Oh et al., "Efficacy and Safety of Tolebrutinib Versus Teriflunomide in Relapsing Multiple Sclerosis: Results from the Phase 3 GEMINI 1 and 2 Trials", O135/4026, Multiple Sclerosis Journal; 30: (3S), pp. 1145-1146 (2024).
Oh et al., "MRI, Safety, and Efficacy Outcomes in Patients with Relapsing MS: 18-month Results from the Long-term Extension Study of Tolebrutinib", P102, Presented at the American Committee for Treatment and Research in Multiple Sclerosis (ACTRIMS) Forum, Feb. 24-26, 2022, West Palm Beach, FL (1 page).

(56) References Cited

OTHER PUBLICATIONS

Oh et al., "MRI, Safety, and Efficacy Outcomes in Patients with Relapsing MS: 18-month Results from the Long-term Extension Study of Tolebrutinib", P102, Multiple Sclerosis Journal, 28: (1S), p. 66 (2022).
Oh et al., "Paramagnetic Rim Lesions as a Prognostic and Predictive Biomarker in the Tolebrutinib Phase 3 Trials for Disability Outcomes", LB1.1, Multiple Sclerosis Journal, 31: (2S), pp. 10-11 (2025).
Oh et al., "Paramagnetic Rim Lesions as a Prognostic and Predictive Biomarker in the Tolebrutinib Phase 3 Trials for Disability Outcomes", P755, Presented at the 10th Annual Americas Committee for Treatment and Research in Multiple Sclerosis (ACTRIMS) Forum, Feb. 27-Mar. 1, 2025; West Palm Beach, Florida (11 pages).
Oh et al., "Safety and Clinical Efficacy Outcomes From the Long-term Extension Study of Tolebrutinib in Participants With Relapsing Multiple Sclerosis: 2.5-Year Results", AAN 2023, Platform S16 010 (11 pages).
Oh et al., "Safety and Clinical Efficacy Outcomes from the Long-term Extension Study of Tolebrutinib in Participants with Relapsing Multiple Sclerosis: 2.5-Year Results", (S16.010), Neurology, MS Clinical Trials and Therapeutics, 100 (17_supplement_2) (Apr. 28, 2023)(3 pages).
Oh et al., "Safety and Clinical Efficacy Outcomes from the Long-term Extension Study of Tolebrutinib in Participants with Relapsing Multiple Sclerosis:3-Year Results", P278/1470, Multiple Sclerosis Journal, 29: (3S), pp. 334-335 (2023).
Oh et al., "Safety and Clinical Efficacy Outcomes From the Long-Term Extension Study of Tolebrutinib in Participants With Relapsing Multiple Sclerosis: 3-Year Results", P278, Presented at the 9th Joint ECTRIMS-ACTRIMS Meeting; Milan, Italy; Oct. 11-13, 2023 (1 page).
Oh et al., "Safety and Clinical Efficacy Outcomes from the Long-Term Extension Study of Tolebrutinib in Patients with Relapsing Multiple Sclerosis: 2-Year Results", P308, Presented at the 38th Congress of the European Committee for Treatment and Research in Multiple Sclerosis (ECTRIMS); Amsterdam, the Netherlands; Oct. 26-28, 2022 (1 page).
Oh et al., "Safety and Efficacy Outcomes From the Long-term Extension Study of Tolebrutinib in Patients With Relapsing MS: Year 1 Results", P667, Presented at the 37th Congress of the European Committee for Treatment and Research in Multiple Sclerosis, Oct. 13-15, 2021, Virtual (1 page).
Oh et al., "Safety and efficacy outcomes from the long-term extension study of tolebrutinib in patients with relapsing MS: Year 1 results", P667, Multiple Sclerosis Journal, 27: (2S), pp. 571-572 (2021).
Oh et al., "Safety and Efficacy Outcomes in Patients with Relapsing MS: 18-month Results from the Longterm Extension Study of Tolebrutinib", AAN 2022, Platform S 14:003 (10 pages).
Oh et al., "Tolebrutinib versus Teriflunomide in Relapsing Multiple Sclerosis", The New England Journal of Medicine, Apr. 8, 2025 (12 pages); DOI: 10.1056/NEJMoa2415985.
Orlandi et al., "Tolebrutinib. Bruton tyrosine kinase (BTK) inhibitor Treatment of multiple sclerosis", Drugs of the Future, 47(5), pp. 325-336 (2022).
Osborne, R., "MS Aubagio tableau: Sanofi talks tolebrutinib, Immunic the pick?", BioWorld, Sep. 20, 2024 (3 pages) (www.bioworld.com/articles/712670-ms-aubagio-tableau-sanofi-talks-tolebrutinib-immunic-the-pick.
Pachner et al., "Clinical utility of a molecular signature in inflammatory demyelinating disease", Neurol Neuroimmunol Neuroinflamm, 6:e520 (2019) (10 pages).
Papasouliotis et al., "Determination of a clinically effective evobrutinib dose: Exposure-response analyses of a phase II relapsing multiple sclerosis study", Clin Transl Sci., 15, pp. 2888-2898 (2022).
Polman et al., "Diagnostic Criteria for Multiple Sclerosis: 2005 Revisions to the McDonald Criteria", Ann Neurol, 58, pp. 840-846 (2005).
Real Talk MS, "ECTRIMS Extra: Results from the Tolebrutinib Phase 3 Clinical Trial for RRMS with Dr. Jiwon Oh", Oct. 4, 2024 (6 pages).
Real Talk MS, "Episode 373: ECTRIMS Research Roundup Part 2 with Dr. Bruce Bebo", with transcript, Oct. 22, 2024 (11 pages).
Real Talk MS, "RealTalk MS ECTRIMS Extra: Tolebrutinib and RRMS", with transcript, Dec. 15, 2024 (11 pages).
Real Talk MS, "RealTalk MS ECTRIMS Extra: Tolebrutinib and SPMS", with transcript, Dec. 15, 2024 (10 pages).
Real Talk MS, "RealTalk MS, Episode 369: ECTRIMS 2024 with Kristine Werner Ozug and Dr. Bruce Bebo", with translation, Sep. 24, 2024 (12 pages).
Reich et al., "A Phase 2 Trial of Tolebrutinib, a Bruton's Tyrosine Kinase Inhibitor, for Chronic Active Lesions in Multiple Sclerosis", National Institute of Neurological Disorders and Stroke, EPO-600, Presentation (1 page) (2024).
Reich et al., "A phase 2 trial of tolebrutinib, a Bruton's tyrosine kinase inhibitor, for chronic active lesions in multiple sclerosis", EPO-600, EAN, Abstract, 687 (2024).
Reich et al., "Efficacy and safety outcomes in patients with relapsing forms of MS treated with the CNS-Penetrating BTK inhibitor SAR442168: results from the phase 2b trial", O4010, European Journal of Neurology, 27 (Suppl. 1), p. 91 (2020).
Reich et al., "Efficacy and Safety Outcomes in Patients With Relapsing Forms of MS Treated With the CNS-Penetrating BTK Inhibitor SAR442168: Results From the Phase 2b Trial", Presentation from EAN 2020, O4010 (17 pages).
Reich et al., "MRI Outcomes from the Long-term Extension Study of Tolebrutinib in Participants with Relapsing Multiple Sclerosis: 3-Year Results", P684/1478, Multiple Sclerosis Journal, 29:592 (3S)(2023).
Reich et al., "MRI Outcomes From the Long-Term Extension Study of Tolebrutinib in Participants With Relapsing Multiple Sclerosis: 3-Year Results", P684, Presented at the 9th Joint ECTRIMS-ACTRIMS Meeting; Milan, Italy; Oct. 11-13, 2023 (1 page).
Reich et al., "MRI Outcomes from the Long-term Extension Study of Tolebrutinib in Patients with Relapsing MS: 18-Month Results", Presented at the American Academy of Neurology (AAN) Virtual Annual Meeting, Apr. 24-26, 2022 (1 page).
Reich et al., "MRI Outcomes from the Long-Term Extension Study of Tolebrutinib in Patients with Relapsing Multiple Sclerosis: 2-Year Results", P297, Presented at the 38th Congress of the European Committee for Treatment and Research in Multiple Sclerosis (ECTRIMS); Amsterdam, the Netherlands; Oct. 26-28, 2022 (1 page).
Reich et al., MRI Outcomes from the Long-term Extension Study of Tolebrutinib in Patients with Relapsing Multiple Sclerosis: 18-Month Results (P1-1. Virtual), Neurology, MS and CNS Inflammatory Disease Virtual, 98 (18_supplement) (May 3, 2022) (1 page).
Reich et al., "MRI outcomes from the long-term extension study of tolebrutinib in patients with relapsing multiple sclerosis: 2-year results", P297, Multiple Sclerosis Journal, 28: (3S), pp. 334-335 (2022).
Reich et al., "MRI outcomes from the long-term extension study of tolebrutinib in relapsing MS: Year 1 results", P666, Multiple Sclerosis Journal, 27: (2S), p. 571 (2021).
Reich et al., "MRI Outcomes From the Long-term Extension Study of Tolebrutinib in Relapsing MS: Year 1 Results", P666, Presented at the 37th Congress of the European Committee for Treatment and Research in Multiple Sclerosis, Oct. 13-15, 2021, Virtual (1 page).
Rijvers et al., "Human T-bet+ B cell development is associated with BTK activity and suppressed by evobrutinib", JCI insight, 7(16): e160909 (2022).
Rocky Mountain MS Center, "BTK inhibitors Update: Tolebrutinib Phase 3 Clinical Trial Results", Sep. 16, 2024 (3 pages).
Sanofi Media Update, "Patient enrollment of phase III tolebrutinib trials paused in the U.S.", 2 pages, Jun. 30, 2022.
Sanofi Press Release, "Tolebrutinib phase 3 data published in NEJM demonstrate benefit on disability progression in multiple sclerosis", 4 pages, Apr. 8, 2025.
Sanofi Press Release, "Tolebrutinib regulatory submission accepted for priority review in the US for patients with multiple sclerosis", Mar. 25, 2025 (3 pages).

(56) References Cited

OTHER PUBLICATIONS

Sanofi, Amended Clinical Trial Protocol 08, "An interventional, Phase 3 extension study to investigate long-term safety and tolerability of tolebrutinib in participants with relapsing multiple sclerosis, primary progressive multiple sclerosis, or nonrelapsing secondary progressive multiple sclerosis", LTS17043, EUCT 2023-503631-18 (Sep. 27, 2024) (140 pages).
Sanofi, Amended Clinicial Trial Protocol 14, "A Phase 3, randomized, double-blind, efficacy andsafety study comparing SAR442168 to placebo inparticipants with primary progressive multiplesclerosis (PERSEUS)", EFC16035, SAR442168 (Oct. 31, 2024) (163 pages).
Scalfari et al., "Smouldering-Associated Worsening in Multiple Sclerosis: An International Consensus Statement on Definition, Biology, Clinical Implications, and Future Directions", Annals of Neurology, 96, pp. 826-845 (2024).
Schwind et al., "Quantitative functional measures in MS: What is a reliable change?" Neurology, 58, pp. 1294-1296 (2002).
Smith et al., "Phase 1 Clinical Trial of PRN2246 (SAR442168), a Covalent BTK Inhibitor Demonstrates Safety, CNS Exposure and Therapeutic Levels of BTK Occupancy", ACTRIMS, P072, Feb. 28, 2019 (1 page).
Syed et al., "Efficacy and Safety of Tolebrutinib in Adults with Generalized Myasthenia Gravis: Phase 3 Study Design", eP03.04.09, J Neuromusc Dis, Abstracts, S246-S247 (2022).
Syed et al., "Efficacy and Safety of Tolebrutinib in Patients with Highly Active Relapsing MS: Subgroup Analysis of the Phase 2b Study (2260)", Neurology, MS and CNS Inflammatory Disease: Emerging Therapeutics and Biomarkers, 96 (15_supplement) (Apr. 13, 2021) (3 pages).
Syed et al., "Subgroup Analysis of Patients With Relapsing MS and Highly Active Disease in the Tolebrutinib Phase 2b Study", AAN 2021, Platform S25:004 (11 pages).
Turner et al., "Comparative CNS Pharmacology of Tolebrutinib Versus Other BTK Inhibitor Candidates for Treating MS (S46.007)", Neurology, MS Therapeutics and Clinical Decision Making, AAN, 100 (17_supplement_2), Apr. 28, 2023 (2 pages).
Traboulsee et al., "Lack of Rebound Disease Activity in Patients with Relapsing Multiple Sclerosis Following Placebo Run-Out in the Tolebrutinib Phase 2b Trial", P296, Presented at the 38th Congress of the European Committee for Treatment and Research in Multiple Sclerosis (ECTRIMS); Amsterdam, the Netherlands; Oct. 26-28, 2022 (1 page).
Turner et al., "Comparative CNS Pharmacology of the Bruton's Tyrosine Kinase (BTK) Inhibitor Tolebrutinib Versus Other BTK Inhibitor Candidates for Treating Multiple Sclerosis", Drugs in R&D, 24, pp. 263-274 (2024).
Notification of Transmittal of The International Search Report and The Written Opinion of the International Searching Authority issued in International Application No. PCT/US2021/064800 on Apr. 4, 2022 (11 pages).
Chang, Betty Y., et al., "The Bruton tyrosine kinase inhibitor PCI-32765 ameliorates autoimmune arthritis by inhibition of multiple effector cells." Arthritis Research & Therapy, 2011; vol. 13, Article No. R115.
Chen et al., "A 2-in-1 Adaptive Phase 2/3 Design for Expedited Oncology Drug Development", Contemporary Clinical Trials, vol. 64, pp. 238-242.
Chen et al., "The effect of Bruton's tyrosine kinase (BTK) inhibitors on collagen-induced platelet aggregation, BTK, and tyrosine kinase expressed in hepatocellular carcinoma (TEC)", Eur J Haematol., 2018;101, pp. 604-612.
Chiang et al., "Juvenile myasthenia gravis", Muscle Nerve, 39, pp. 423-431 (2009).
Chisari et al., "Rituximab for the treatment of multiple sclerosis: a review", J Neurol., 8, pp. 1-25 (Jan. 2021).
Chitnis et al., "Demographics of pediatric-onset multiple sclerosis in an MS center population from the Northeastern United States", Mult Scler., 15(5), pp. 627-631 (May 2009) doi: 10.1177/1352458508101933. Epub Mar. 19, 2009.
Clinical Trial Results of EU Clinical Trials Register No. 2018-003927-12, "A Phase2b dose-finding study for SAR442168, a Bruton's tyrosine kinase inhibitor, in participants with relapsing multiple sclerosis", Dec. 31, 2020 (23 pages).
ClinicalTrial.gov ID No. NCT05132569, "Efficacy and Safety of Tolebrutinib (SAR442168) Tablets in Adult Participants With Generalized Myasthenia Gravis (URSA)", Last Updated Mar. 10, 2023 (9 pages).
ClinicalTrials.gov ID No. NCT03889639, "Dose-finding Study for SAR442168 in Relapsing Multiple Sclerosis", Last Updated Mar. 8, 2023 (11 pages).
ClinicalTrials.gov ID No. NCT03996291, "Long Term Safety and Efficacy Study of Tolebrutinib (SAR442168) in Participants with Relapsing Multiple Sclerosis", Last Updated Apr. 24, 2023 (8 pages).
ClinicalTrials.gov ID No. NCT04171310, "Study of Excretion Balance and Pharmacokinetics of [14C]-SAR442168 in Healthy Male Subjects", Last Updated Apr. 25, 2022 (7 pages).
ClinicalTrials.gov ID No. NCT04410978, "Relapsing Forms of Multiple Sclerosis (RMS) Study of Bruton's Tyrosine Kinase (BTK) Inhibitor Tolebrutinib (SAR442168) (Gemini 1)", Last Updated Aug. 8, 2022 (11 pages).
ClinicalTrials.gov ID No. NCT04410991, "Relapsing Forms of Multiple Sclerosis (RMS) Study of Bruton's Tyrosine Kinase (BTK) Inhibitor Tolebrutinib (SAR442168) (Gemini 2)", Last Updated Aug. 8, 2022 (9 pages).
ClinicalTrials.gov ID No. NCT04411641, "Nonrelapsing Secondary Progressive Multiple Sclerosis (NRSPMS) Study of Bruton's Tyrosine Kinase (BTK) Inhibitor Tolebrutinib (SAR442168) (HERCULES)", Last Updated Feb. 10, 2023 (9 pages).
ClinicalTrials.gov ID No. NCT04458051, "Primary Progressive Multiple Sclerosis (PPMS) Study of Bruton's Tyrosine Kinase (BTK) Inhibitor Tolebrutinib (SAR442168) (Perseus)", Last Updated Feb. 1, 2023 (9 pages).
ClinicalTrials.gov ID No. NCT04742400, "Tolebrutinib, a Brain-penetrant Bruton s Tyrosine Kinase Inhibitor, for the Modulation of Chronically Inflamed White Matter Lesions in Multiple Sclerosis", Last Updated Jul. 3, 2023 (12 pages).
ClinicalTrials.gov ID No. NCT05282030, "Study to Assess the Plasma Concentration of Tolebrutinib Given as a Tablet to Adult Participants With Renal Impairment Compared to Healthy Participants", Last Updated Jan. 26, 2023 (8 pages).
ClinicalTrials.gov ID No. NCT05283915, "Study to Assess the Plasma Concentration of Tolebrutinib Given as a Tablet to Adult Participants with Mild Hepatic Impairment Compared to Participants With Normal Hepatic Function", Last Updated Nov. 8, 2022 (8 pages).
Coles et al., "Monoclonal antibody treatment exposes three mechanisms underlying the clinical course of multiple sclerosis", Ann Neurol, 46(3), pp. 296-304 (1999).
Common Terminology Criteria for Adverse Events (CTCAE) Quick Reference (May 28, 2009) (196 pages) (http://evs.nci.nih.gov/ftp1/CTCAE/CTCAE_4.03_2010-06-14_QuickReference_5x7.pdf).
Confavreux et al., "Natural history of multiple sclerosis: a unifying concept", Brain., 129(Pt 3), pp. 606-616 (Mar. 2006).
Corneth et al., "BTK Signaling in B Cell Differentiation and Autoimmunity. In: Kurosaki T., Wienands J. (eds) B Cell Receptor Signaling", Current Topics in Microbiology and Immunology, vol. 393. Springer, Cham. https://doi.org/10.1007/82_2015_478 (2015).
Cottrell et al., "The natural history of multiple sclerosis: a geographically based study. 5. The clinical features and natural history of pimary progressive multiple sclerosis", Brain, 122, pp. 625-639 (1999).
Crawford et al., "Discovery of GDC-0853: A Potent, Selective, and Noncovalent Bruton's Tyrosine Kinase Inhibitor in Early Clinical Development", J Med Chem., 22;61(6), pp. 2227-2245 (2018).
Cron, et al. "Thymus involvement in early-onset myasthenia gravis", Ann N Y Acad Sci., 1412(1), pp. 137-145 (Jan. 2018).
Dahl et al., "Radiosynthesis of a Bruton's tyrosine kinase inhibitor, [11C]Tolebrutinib, via palladium-NiXantphos-mediated carbonylation", J Label Compd Radiopharm., 63, pp. 482-487 (2020).

(56) References Cited

OTHER PUBLICATIONS

Dalton et al., "Effect of natalizumab on conversion of gadolinium enhancing lesions to T1 hypointense lesions in relapsing multiple sclerosis", J Neurol, 251, pp. 407-413 (2004).
Debouverie et al., "Multiple sclerosis with a progressive course from onset in Lorraine-Eastern France", J Neurol, 254, pp. 1370-1375 (2007).
Deenen et al., "The Epidemiology of Neuromuscular Disorders: A Comprehensive Overview of the Literature", J Neuromuscul Dis., 2(1), pp. 73-85 (2015).
Dendrou et al., "Immunopathology of multiple sclerosis", Nature Reviews Immunology, 15, pp. 545-558 (2015).
Di Paolo, et al., "Specific Btk inhibition suppresses B cell- and myeloid cell-mediated arthritis", Nature Chemical Biology, vol. 7, pp. 41-50 (Jan. 2011).
Dilokthornsakul et al., "Multiple Sclerosis Prevalence in the United States Commercially Insured Population", Neurology, 86(11), pp. 1014-1021 (Mar. 15, 2016).
Duquette et al., "Multiple sclerosis in childhood: Clinical profile in 125 patients", Journal of Pediatrics, 111, pp. 359-363 (1987).
EMD Serono Inc., "Positive lake-breaking Phase II data evaluating investigational oral therapy, evobrutinib in RMS [Online]", Oct. 12, 2018. Available from: URL:http://media.emdserono.com/press-releases?item=122714 (7 pages).
English translation of CN 105753863 A, published Jul. 13, 2016 [57 pages].
English Translation of Japanese Patent No. 2012246314A, issued on Dec. 13, 2012 (120 pages).
English translation of WO 2022/223027, published Oct. 27, 2022, retrieved from Espacenet on Jan. 23, 2023 (2022) (17 pages).
Erickson et al., "Bruton's Tyrosine Kinase Small Molecule Inhibitors Induce a Distinct Pancreatic Toxicity in Rats." J Pharmacol Exp Ther. 2017;360(1):226-38.
Ethnic Factors in The Acceptability of Foreign Clinical Data E5(R1) http://www.ich.org (Sep. 1998) (15 pages).
EU Clinical Trials Register No. 2018-003927-12, "A Phase2b dose-finding study for SAR442168, a Bruton's tyrosine kinase inhibitor, in participants with relapsing multiple sclerosis", first entered into EudraCT Jan. 11, 2019 (5 pages).
EU Clinical Trials Register No. 2018-004731-76, "Long-term extension safety and efficacy study of SAR442168 in participants with relapsing multiple sclerosis", first entered into EudraCT Feb. 25, 2019 (6 pages).
EU Clinical Trials Register No. 2020-000637-41, "A Phase 3, randomized, double-blind efficacy and safety study comparing SAR442168 to teriflunomide (Aubagio®) in participants with relapsing forms of multiple sclerosis", first entered into EudraCT Jun. 17, 2020 (7 pages).
EU Clinical Trials Register No. 2020-000644-55, "A Phase 3, randomized, double-blind efficacy and safety study comparing SAR442168 to teriflunomide (Aubagio®) in participants with relapsing forms of multiple sclerosis", first entered into EudraCT Jun. 15, 2020 (7 pages).
EU Clinical Trials Register No. 2020-000645-14, A Phase 3, randomized, double-blind, efficacy and safety study comparing SAR442168 to placebo in participants with primary progressive multiple sclerosis (PERSEUS), first entered into EudraCT Jul. 27, 2020 (6 pages).
EU Clinical Trials Register No. 2020-00647-30, "A Phase 3, randomized, double-blind, efficacy and safety study comparing SAR442168 to placebo in participants with nonrelapsing secondary progressive multiple sclerosis", first entered into EudraCT Jun. 16, 2020 (6 pages).
EU Clinical Trials Register No. 2021-003898-59, "A Phase 3, randomized, double-blind, placebo-controlled, parallel-group study to evaluate the efficacy and safety of tolbrutinib (SAR442168) in adults with generalized myasthenia gravis (MG)", first entered into EudraCT Oct. 6, 2021 (7 pages).
European Medicines Agency. "Guideline on the investigation of drug interactions." Jun. 21, 2012.
Evans et al., "Inhibition of Btk with CC-292 Provides Early Pharmacodynamic Assessment of Activity in Mice and Humans", J Pharmacol Exp Ther, 346(2), pp. 219-228 (Aug. 2013).
Evoli A., "Acquired myasthenia gravis in childhood", Curr Opin Neurol., 23(5), pp. 536-540 (Oct. 2010).
Fadda et al., "Canadian Pediatric Demyelinating Disease Network. MRI and laboratory features and the performance of international criteria in the diagnosis of multiple sclerosis in children and adolescents: a prospective cohort study", Lancet Child Adolesc Health., 2(3), pp. 191-204 (Mar. 2018).
"General Tests, Processes and Apparatus—2.58 X-Ray Powder Diffraction Method", Japanese Pharmacopoeia, 16th edition, 2011, pp. 75-79 (English version).
English Translation of Japanese Patent No. 2016-094368A, issued on May 26, 2016 (15 pages).
Sanofi Press Release, "Tolebrutinib designated Breakthrough Therapy by the FDA for non-relapsing secondary progressive multiple sclerosis", Dec. 13, 2024 (3 pages).
Kappos et al., "Ocrelizumab in relapsing-remitting multiple sclerosis: a phase 2, randomised, placebo-controlled, multicentre trial", The Lancet, 378(9805), pp. 1779-1787 (Nov. 19, 2011).
Kappos L, et; al., "Siponimod versus placebo in secondary progressive multiple sclerosis (EXPAND): a double-blind, randomised, phase 3 study.", Lancet. 2018;391(10127):1263-73.
Kappos, L., et al., "Natalizumab treatment for multiple sclerosis: recommendations for patient selection and monitoring", Lancet Neurol, 6(5), pp. 431-441 (2007).
Kim et al., "Imidazo[1,5-a]quinoxalines as irreversible BTK inhibitors for the treatment of rheumatoid arthritis", Bioorg Med Chem Lett., 21, pp. 6258-6263 (2011).
Kozuki, T., "Skin problems and EGFR-tyrosine kinase inhibitor." Jpn J Clin Oncol., 46(4), pp. 291-298. (Apr. 2016).
Krupp et al., "International Pediatric Multiple Sclerosis Study Group. International Pediatric Multiple Sclerosis Study Group", Multiple Sclerosis Journal., 19, pp. 1261-1267 (2011).
Kuks J.B.M., "Clinical Presentations of Myasthenia Gravis: Myasthenia Gravis and Related Disorders", Current Clinical Neurology, 2018. p. 58-100.
Kurtzke J F, "Rating neurologic impairment in multiple sclerosis: an expanded disability status scale (EDSS).", Neurology. 1983;33(11):1444-52.
Langer-Gould et al., "Incidence of acquired CNS demyelinating syndromes in a multiethnic cohort of children", Neurology, 77(12), pp. 1143-1148 (Sep. 2011).
Lazaridis et al., "Myasthenia Gravis: Autoantibody Specificities and Their Role in MG Management", Front Neurol, p. 30;11:59698 (2020).
Lebakken et al., "Development and applications of a broad-coverage, TR-FRET-based kinase binding assay platform", J Biomol Screen, 14, pp. 924-935 (2009).
Lee et al., "B cell depletion therapies in autoimmune disease: advances and mechanistic insights", Nature Reviews Drug Discovery, 20(3), pp. 179-199 (Dec. 15, 2020).
Lee et al., "Juvenile Myasthenia Gravis in Korea: Subgroup Analysis According to Sex and Onset Age", J Child Neurol, 31(14), pp. 1561-1568 (Dec. 2016).
Lee et al., "Safety, pharmacokinetics, and pharmacodynamics of BMS-986142, a novel reversible BTK inhibitor, in healthy participants", European Journal of Clinical Pharmacology, 73(6), pp. 689-698 (2017).
Lehmann-Horn K, et. al., "Deciphering the role of B cells in multiple sclerosis—towards specific targeting of pathogenic function.", Int J Mol Sci. 2017; 18(10):2048.
Li et al., "Comparative efficacy and acceptability of disease-modifying therapies in patients with relapsing-remitting multiple sclerosis: a systematic review and network meta-analysis", J Neurol, pp. doi: 10.1007/s00415-019-09395-w (2020).
Linder et al., "Outcome in juvenile-onset myasthenia gravis: a retrospective study with long-term follow-up of 79 patients", J Neurol., 244(8), pp. 515-520 (Aug. 1997).
Lindstrom et al., "Antibody to acetylcholine receptor in myasthenia gravis. Prevalence, clinical correlates, and diagnostic value", Neurology., 26(11), pp. 1054-1059 (Nov. 1976).

(56) References Cited

OTHER PUBLICATIONS

Lipsky et al., "Incidence and risk factors of bleeding-related adverse events in patients with chronic lymphocytic leukemia treated with ibrutinib", Haematologica., 100(12), pp. 1571-1578 (Dec. 2015).
Liu et al., "Analysis of mortality and related factors in 2195 adult myasthenia gravis patients in a 10-year follow-up study", Neurol India, 65(3), pp. 518-524 (May-Jun. 2017).
Liu et al., "Disability outcome measures in therapeutic trials of relapsing-remitting multiple sclerosis: effects of heterogeneity of disease course in placebo cohorts", J Neurol Neurosurg Psychiatry, vol. 68, pp. 450-457 (2000).
Liu et al., "Tacrolimus Improves Symptoms of Children With Myasthenia Gravis Refractory to Prednisone", Pediatr Neurol., 77, pp. 42-47 (Dec. 2017).
Lublin F D, et al., "Defining the clinical course of multiple sclerosis: the 2013 revisions.", Neurology. 2014;83(3):278-86.
Lynch et al., "Epidermal growth factor receptor inhibitor-associated cutaneous toxicities: an evolving paradigm in clinical management", Oncologist, 12(5), pp. 610-621 (May 2007).
Mader et al., "Pathomechanisms in demyelination and astrocytopathy: autoantibodies to AQP4, MOG, GFAP, GRP78 and beyond", Current Opinion in Neurology, 35(3), pp. 427-435 (Jun. 1, 2022).
Mangla et al., "Pleiotropic consequences of Bruton tyrosine kinase deficiency in myeloid lineages lead to poor inflammatory responses", Blood, 104, pp. 1191-1197 (2004).
Mansukhani et al., "Incidence and Ocular Features of Pediatric Myasthenias", Am J Ophthalmol., 200, pp. 242-249 (Apr. 2019).
Marta et al., "Microglial Fc receptors mediate physiological changes resulting from antibody cross-linking of myelin oligodendrocyte glycoprotein", J Neuroimmunol., 196(1-2), pp. 35-40 (2008).
Massimiliano et al., "Smoothness of gait detects early alterations of walking in persons with multiple sclerosis without disability", Gait & Posture, 58, pp. 307-309 (2017).
McGrogan et al., "The Incidence of Myasthenia Gravis: A Systematic Literature Review", Neuroepidemiology, 34, pp. 171-183 (2010).
McPherson et al., "Correlation of Quantitative Myasthenia Gravis and Myasthenia Gravis Activities of Daily Living scales in the MGTX study", Muscle Nerve, 62(2), pp. 261-266 (2020).
Medicinenet.com, Definition of Cancer (2004). (http://www.medterms.com) (1 page).
Mehta et al., "Iron is a Sensitive Biomarker for Inflammation in Multiple Sclerosis Lesions", PLOS One, 8(3), p. e57573 (Mar. 14, 2013).
Merck Press release. Merck KGaA, Darmstadt, Germany, "Announces Positive Phase IIB Results for Evobrutinib in Relapsing Multiple Sclerosis.", Mar. 7, 2018.
Mexhitaj et al., "Abnormal effector and regulatory T cell subsets in paediatric-onset multiple sclerosis", Brain, 142(3), pp. 617-632 (2019).
Meyer-Moock et al., "Systematic literature review and validity evaluation of the expanded disability status scale (EDSS) and the multiple sclerosis functional composite (MSFC) in patients with multiple sclerosis", BMC Neurol., 14, p. 58 (Mar. 25, 2014).
Miller, R., "Chapter 10—Population Pharmacokinetics", Principles of clinical pharmacology, second edition, pp. 129-139 (2007).
Mohamed et al., "Bruton's tyrosine kinase (Btk): function, regulation, and transformation with special emphasis on the PH domain", Immunol Rev., 228, pp. 58-73 (2009).
Montalban et al., "Evobrutinib Phase 2 MS manuscript—Supplement", Electronic resource, URL: https://scientiasalut.gencat.cat/bitstream/handle/11351/4593/placebo_controlled_trial_oral_BTK_inhibitor_multiple_sclerosis_2019_appendix.pdf?sequence=3&isAllowed=y, date of access Apr. 22, 2024, table S2.
Montalban et al., "Placebo-Controlled Trial of an Oral BTK Inhibitor in Multiple Sclerosis", The New England Journal of Medicine, 380(25), pp. 2406-2417 (Jun. 20, 2019).
Montalban X, et al. "Ocrelizumab versus placebo in primary progressive multiple sclerosis", N Engl J Med. 2017;376(3):209-20.
Morrow et al., "Predicting loss of employment over three years in multiple sclerosis: Clinically meaningful cognitive decline", Clin Neuropsychol, 24, pp. 1131-1145 (2010).
Mowry et al., "Multiple sclerosis susceptibility genes: associations with relapse severity and recovery", PLoS One 2013; 8:e75416.
Munot et al., "242nd ENMC international diagnosis and management of juvenile myasthenia gravis Hoofddorp, the Netherlands, Mar. 1-3, 2019", Neuromuscul Disord., 30, pp. 254-264 (2010).
Muppidi et al., "MG-ADL: Still a relevant outcome measure", Muscle Nerve, vol. 44, pp. 727-731 (2011).
Muppidi, "The myasthenia gravis-specific activities of daily living profile", Ann N.Y. Acad Sci, vol. 1274, pp. 114-119 (2012).
Murray et al., "Semiparametric Bayesian Commensurate Survival Model for Post-Market Medical Device Surveillance with Non-Exchangeable Historical Data", Biometrics, 70, pp. 185-191 (Mar. 2014).
Narayanaswami et al., "International Consensus Guidance for Management of Myasthenia Gravis: 2020 Update", Neurology, 96(3), pp. 114-122 (Jan. 19, 2021).
National MS Society web site (https://www.nationalmssociety.org/What-is-MS/MS-FAQ-s) (5 pages).
Navarro et al., "Antiviral Immunity", Curr Immunol Rev., 7, pp. 19-24 (2011).
Absinta et al., "Association of Chronic Active Multiple Sclerosis Lesions With Disability In Vivo", JAMA Neurology, 76 (12), pp. 1474-1483 (2019).
Akinsanya et al., "Toward the Use of Paramagnetic Rim Lesions in Proof-of-Concept Clinical Trials for Treating Chronic Inflammation in Multiple Sclerosis", National Institute of Neurological Disorders and Stroke, ACTRIMS, P126, 2021 (10 pages).
Akinsanya et al., "Toward the Use of Paramagnetic Rim Lesions in Proof-of-Concept Clinical Trials for Treating Chronic Inflammation in Multiple Sclerosis", P126, Multiple Sclerosis Journal, 27: (1S), pp. 74-75 (2021).
Ali Raza et al., "(0058/1599) Cerebrospinal fluid myeloid modulation in patients with multiple sclerosis treated with tolebrutinib", Multiple Sclerosis Journal; 29: (3S), pp. 41-42 (2023).
Ali Raza et al., "Cerebrospinal fluid and serum proteome signature for chronic active multiple sclerosis", P253, National Institute of Neurological Disorders and Stroke, ECTRIMS (1 page) (2024).
Ali Raza et al., "Cerebrospinal fluid myeloid modulation in patients with multiple sclerosis treated with tolebrutinib", National Institute of Neurological Disorders and Stroke, ECTRIMS 2023, Italy (11 pages).
Ali Raza et al., "CSF and serum proteome signature for chronic active multiple sclerosis", P253/1586, Multiple Sclerosis Journal, 30: (3S), p. 303 (2024).
Arnold et al., "Effect of Evobrutinib on Slowly Expanding Lesion vol. in Relapsing Multiple Sclerosis. A Post Hoc Analysis of a Phase 2 Trial", Neurology®, 102:e208058 (2024) (11 pages).
Bagnato et al., "Associations between chronic active lesions and clinical outcomes in multiple sclerosis: A systematic literature review", JMCP.org, 31(7), pp. 694-721 (Jul. 2025).
Bagnato et al., "Imaging chronic active lesions in multiple sclerosis: a consensus statement", Brain, 147, pp. 2913-2933 (2024).
Barr et al., "Microglial BTK Signaling Regulates Immune-Mediated Cortical Demyelination", P196, Multiple Sclerosis Journal, 27: (1S), pp. 107-108 (2021).
Barr et al., "Microglial BTK signaling regulates immune-mediated cortical demyelination", Poster P196, ACTRIMS (10 pages) (2021).
Becker et al., "Safety, Tolerability, Pharmacokinetics, Target Occupancy, and Concentration-QT Analysis of the Novel BTK Inhibitor Evobrutinib in Healthy Volunteers", Clin Transl Sci, 13, pp. 325-336 (2020).
Blazier et al., "Evaluating Large Scale Proteomic Changes in Cerebrospinal Fluid of Multiple Sclerosis Patients Treated with Tolebrutinib", P019, Presented at the 8th Annual Americas Committee for Treatment and Research in Multiple Sclerosis (ACTRIMS) Forum; San Diego, CA, USA; Feb. 23-25, 2023 (1 page).
Blazier et al., "Evaluating large scale proteomic changes in cerebrospinal fluid of multiple sclerosis patients", EP1037, Multiple Sclerosis Journal; 28: (3S), pp. 833-834 (2022).

(56) References Cited

OTHER PUBLICATIONS

Blazier et al., "Evaluating Large Scale Proteomic Changes in Cerebrospinal Fluid of Multiple Sclerosis Patients", Presented at the 38th Congress of the European Committee for Treatment and Research in Multiple Sclerosis, Oct. 26-28, 2022, Amsterdam, the Netherlands (1 page).
Blazier et al., "Tolebrutinib Can Reverse Multiple Sclerosis-Induced Cerebrospinal Fluid Proteomic Alterations", P645, Presented at the 9th Joint ECTRIMS-ACTRIMS Meeting; Milan, Italy; Oct. 11-13, 2023.
Bojanowski et al., "Efficacy and Safety of the Bruton's Tyrosine Kinase Inhibitor Evobrutinib in Patients with Relapsing Multiple Sclerosis over 48 Weeks: a Randomised, Placebocontrolled, Phase 2 Study", Multiple Sclerosis Journal 2020; NP69-NP70 (2020).
Bosworth, Ted, "No Support for BTK Inhibitor in Phase 3 Multiple Sclerosis Trial", ACTRIMS 2024, Medscape Medical News, 4 pages (Mar. 7, 2024).
Cabanis et al., "A phase I trial assessing the safety, pharmacokinetics, cerebrospinal fluid penetrance, and food effect of BTK inhibitor tolebrutinib in healthy volunteers", Clin Transl Sci., 17:e13693 (2024) (12 pages).
Cagol et al., "Association of Spinal Cord Atrophy and Brain Paramagnetic Rim Lesions With Progression Independent of Relapse Activity in People With MS", Neurology, 102:e207768 (2024) (14 pages).
Calabresi, P.A., "Progress toward Mitigating Disability Progression in Multiple Sclerosis", The New England Journal of Medicine, 392;19, pp. 1966-1968 (2025).
Caldwell et al., "Discovery of Evobrutinib: An Oral, Potent, and Highly Selective, Covalent Bruton's Tyrosine Kinase (BTK) Inhibitor for the Treatment of Immunological Diseases", J. Med. Chem., 62, pp. 7643-7655 (2019).
Chertcoff et al., "Recent Advances in Diagnostic, Prognostic, and Disease-Monitoring Biomarkers in Multiple Sclerosis", Neurol Clin, 42, pp. 15-38 (2024).
Chomyk et al., "Transcript Profiles of Microglia/Macrophage Cells at the Borders of Chronic Active and Subpial Gray Matter Lesions in Multiple Sclerosis", Ann Neurol, 95, pp. 907-916 (2024).
Ciccarelli et al., "Using the Progression Independent of Relapse Activity Framework to Unveil the Pathobiological Foundations of Multiple Sclerosis", Neurology, 103:e209444 (2024) (10 pages).
ClincialTrials.gov, "A Study to Investigate Long-term Safety and Tolerability of Tolebrutinib in Participants With Multiple Sclerosis", NCT06372145, Record History Tab, Version 1, Last Updated Jul. 8, 2025 (13 pages).
ClincialTrials.gov, "Dose-finding Study for SAR442168 in Relapsing Multiple Sclerosis", NCT03889639, Record History Tab, Version 18, Last Updated Mar. 8, 2023 (21 pages).
ClincialTrials.gov, "Efficacy and Safety of Tolebrutinib (SAR442168) Tablets in Adult Participants With Generalized Myasthenia Gravis (URSA)", NCT05132569, Record History Tab, Version 2, Last Updated Apr. 8, 2024 (13 pages).
ClincialTrials.gov, "Efficacy and Safety of Tolebrutinib (SAR442168) Tablets in Adult Participants With Generalized Myasthenia Gravis (URSA)", NCT05132569, Record History Tab, Version 17, Last Updated Apr. 8, 2024 (62 pages).
ClincialTrials.gov, "Efficacy and Safety of Tolebrutinib (SAR442168) Tablets in Adult Participants With Generalized Myasthenia Gravis (URSA)", NCT05132569, Record History Tab, Version 10, Last Updated Apr. 8, 2024 (16 pages).
ClincialTrials.gov, "Long Term Safety and Efficacy Study of Tolebrutinib (SAR442168) in Participants With Relapsing Multiple Sclerosis", NCT03996291, Record History Tab, Version 15, Last Updated Dec. 27, 2024 (15 pages).
ClincialTrials.gov, "Long Term Safety and Efficacy Study of Tolebrutinib (SAR442168) in Participants With Relapsing Multiple Sclerosis", NCT03996291, Record History Tab, Version 17, Last Updated Dec. 27, 2024 (15 pages).
ClincialTrials.gov, "Long Term Safety and Efficacy Study of Tolebrutinib (SAR442168) in Participants With Relapsing Multiple Sclerosis", NCT03996291, Record History Tab, Version 1, Last Updated Dec. 27, 2024 (13 pages).
ClincialTrials.gov, "Long Term Safety and Efficacy Study of Tolebrutinib (SAR442168) in Participants With Relapsing Multiple Sclerosis", NCT03996291, Record History Tab, Version 13, Last Updated Dec. 27, 2024 (17 pages).
ClincialTrials.gov, "Long Term Safety and Efficacy Study of Tolebrutinib (SAR442168) in Participants With Relapsing Multiple Sclerosis", NCT03996291, Record History Tab, Version 3, Last Updated Dec. 27, 2024 (13 pages).
ClincialTrials.gov, "Study of Drug-drug Interaction of the Effects of Gemfibrozil and Rifampicin on SAR442168 in Healthy Adult Subjects", NCT06064539, Record History Tab, Version 1, Last Updated Oct. 3, 2023 (10 pages).
ClincialTrials.gov, "Study of the Tolerability and Pharmacokinetics of Oral Doses of SAR442168 With a Food Effect Investigation in Healthy Adult Participants", NCT06106074, Record History Tab, Version 1, Last Updated Oct. 30, 2023 (10 pages).
ClincialTrials.gov, "Study to Assess the Plasma Concentration of Tolebrutinib Given as a Tablet to Adult Participants with Mild Hepatic Impairment Compared to Participants with Normal Hepatic Function", NCT05283915, Record History Tab, Version 4, Last Updated Jan. 15, 2025 (11 pages).
ClincialTrials.gov, "Tolebrutinib, a Brain-penetrant Bruton's Tyrosine Kinase Inhibitor, for the Modulation of Chronically Inflamed White Matter Lesions in Multiple Sclerosis", NCT04742400, Record History Tab, Version 159, Last Updated Aug. 13, 2024 (29 pages).
ClincialTrials.gov, "Tolebrutinib, a Brain-penetrant Bruton's Tyrosine Kinase Inhibitor, for the Modulation of Chronically Inflamed White Matter Lesions in Multiple Sclerosis", NCT04742400, Record History Tab, Version 95, Last Updated Aug. 13, 2024 (29 pages).
ClincialTrials.gov, "Tolebrutinib, a Brain-penetrant Bruton's Tyrosine Kinase Inhibitor, for the Modulation of Chronically Inflamed White Matter Lesions in Multiple Sclerosis", NCT04742400, Record History Tab, Version 145, Last Updated Aug. 13, 2024 (29 pages).
ClincialTrials.gov, "Tolebrutinib, a Brain-penetrant Bruton's Tyrosine Kinase Inhibitor, for the Modulation of Chronically Inflamed White Matter Lesions in Multiple Sclerosis", NCT04742400, Record History Tab, Version 167, Last Updated Aug. 13, 2024 (41 pages).
ClinicalTrials.gov "Dose-finding Study for SAR442168 in Relapsing Multiple Sclerosis", NCT03889639, v1, Last Updated Mar. 8, 2023 (17 pages).
ClinicalTrials.gov "Dose-finding Study for SAR442168 in Relapsing Multiple Sclerosis", NCT03889639, ver 17, Last Updated Mar. 8, 2023 (21 pages).
ClincialTrials.gov, "Dose-finding Study for SAR442168 in Relapsing Multiple Sclerosis", NCT03889639, Record History Tab, Version 20, Last Updated Mar. 8, 2023 (55 pages).
ClincialTrials.gov, "Nonrelapsing Secondary Progressive Multiple Sclerosis (NRSPMS) Study of Bruton's Tyrosine Kinase (BTK) Inhibitor Tolebrutinib (SAR442168)(HERCULES) (HERCULES)", NCT04411641, Record History Tab, Version 1, Last Updated Jul. 2, 2025 (15 pages).
ClincialTrials.gov, "Nonrelapsing Secondary Progressive Multiple Sclerosis (NRSPMS) Study of Bruton's Tyrosine Kinase (BTK) Inhibitor Tolebrutinib (SAR442168)(HERCULES) (HERCULES)", NCT04411641, Record History Tab, Version 14, Last Updated Jul. 2, 2025 (21 pages).
ClincialTrials.gov, "Nonrelapsing Secondary Progressive Multiple Sclerosis (NRSPMS) Study of Bruton's Tyrosine Kinase (BTK) Inhibitor Tolebrutinib (SAR442168)(HERCULES) (HERCULES)", NCT04411641, Record History Tab, Version 20, Last Updated Jul. 2, 2025 (15 pages).
ClincialTrials.gov, "Nonrelapsing Secondary Progressive Multiple Sclerosis (NRSPMS) Study of Bruton's Tyrosine Kinase (BTK) Inhibitor Tolebrutinib (SAR442168)(HERCULES) (HERCULES)", NCT04411641, Record History Tab, Version 31, Last Updated Jul. 2, 2025 (39 pages).
Sparaco et al., "The Role of Wearable Devices in Multiple Sclerosis", Mult Scler Int.; Review Article, v. 2018.

(56) References Cited

OTHER PUBLICATIONS

Sprenger et al., "Association of brain vol. loss and long-term disability outcomes in patients with multiple sclerosis treated with teriflunomide", Multiple Sclerosis Journal, pp. 1-10 (2019).
Stathopoulos et al., "Evolution of Anti-B Cell Therapeutics in Autoimmune Neurological Diseases", Neurotherapeutics, 19(3), pp. 691-710 (Feb. 18, 2022).
Stys, et al., "Will the real multiple sclerosis please stand up?", Nat Rev Neurosci., 13(7), pp. 507-514 (2012).
Tan et al., "Targeting the SYK-BTK axis for the treatment of immunological and hematological disorders: Recent progress and therapeutic perspectives", Pharmacol Ther., 138(2), pp. 294-309 (2013).
Tang, et al., "Cardiac side effects of bruton tyrosine kinase (BTK) inhibitors", Leuk Lymphoma, 59(7), pp. 1554-1564 (Jul. 2018).
Thompson A J, et al., "Diagnosis of multiple sclerosis: 2017 revisions of the McDonald criteria.", Lancet Neurol.; 17(2):162-73 (2018).
Thompson et al., "Multiple sclerosis", Lancet, 391(10130), 1622-1636 (2018).
Tomassini et al., "Predicting the profile of increasing disability in multiple sclerosis", Multiple Sclerosis Journal, 25(9), pp. 1306-1315 (2019).
Torke et al., "Inhibition of Bruton's tyrosine kinase interfers with pathogenic B-cell development in inflammatory CNS demyelinating disease", ACTA Neuropathologica, 140(4), pp. 535-548 (Aug. 6, 2020).
Traboulsee Anthony et. al., "Design of a Phase 2b Dose-finding Trial to Evaluate Safety and Efficacy of the CNS-penetrant BTK Inhibitor SAR442168 in Patients with Relapsing Forms of Multiple Sclerosis (804) : Neurology", Neurology, Apr. 14, 2020 (Apr. 14, 2020), XP055794139, Retrieved from the Internet: URL:https://n.neurology.org/content/94/15 Supplement/804.abstract—[retrieved by ISA on Apr. 12, 2021].
Traboulsee et al., "Lack of rebound disease activity in patients with relapsing multiple sclerosis following placebo run-out in the tolebrutinib phase 2b trial", Multiple Sclerosis Journal, 28(3_suppl), pp. 130-691 (Oct. 12, 2022).
Tsai et al., "Increased subsequent risk of myasthenia gravis in children with allergic diseases", J Neuroimmunol., 276 (1-2), pp. 202-206 (Nov. 15, 2014).
Tur et al., "Assessing treatment outcomes in multiple sclerosis trials and in the clinical setting", Neurology, 14, pp. 75-93 (2018).
US FDA. In vitro metabolism and transporter-mediated drug-drug interaction studies. [Online]. [Cited Nov. 20, 2018]. Available from:URL:https://www.fda.gov/downloads/Drugs/GuidanceComplianceRegulatoryInformation/Guidances/UCM581965.pdf.
Uzawa et al., "Roles of cytokines and T cells in the pathogenesis of myasthenia gravis", Clin Exp Immunol., 203, pp. 366-374 (2020).
Van Rosmalen et al., "Including historical data in the analysis of clinical trials: Is it worth the effort?", Statistical Methods in Medical Research., 27(10), pp. 3167-3182 (2018).
Vanderver et al., "Relative incidence of inherited white matter disorders in childhood to acquired pediatric demyelinating disorders", Semin Pediatr Neurol., 19(4), pp. 219-223. doi:10.1016/j.spen.2012.10.001. (2012).
Vandiedonck et al., "Genetics of autoimmune myasthenia gravis: the multifaceted contribution of the HLA complex", J Autoimmun., 25 Suppl:6-11 (2005).
Venkateswaran et al., "Pediatric Multiple Sclerosis", The Neurologist, 16(2), pp. 92-105 (Mar. 2010).
Volmering et al., "The Neutrophil Btk Signalosome Regulates Integrin Activation During Sterile Inflammation", Immunity, 44, pp. 73-87 (2016).
Von Budingen, et al., "B cell exchange across the blood brain barrier in multiple sclerosis", J. Clin. Invest., 122(12), pp. 4533-4543 (2012).
Von Lindern et al., "Control of erythropoiesis by erythropoietin and stem cell factor: A novel role for Bruton's tyrosine kinase", Cell Cycle, 3(7), pp. 876-879 (2004).
Wakefield, "Fluorinated Pharmaceuticals", Innovations in Pharmaceutical Technology, pp. 74-78 (2003).
Waldman et al., "Multiple sclerosis in children: an update on clinical diagnosis, therapeutic strategies, and research", Lancet Neurol., 13(9), pp. 936-948. doi: 10.1016/S1474-4422(14)70093-6. Review (Sep. 2014).
Waldman et al., "Pediatric multiple sclerosis: Clinical features and outcome", Neurology, 87(9 Suppl 2):S74-81. (Aug. 30, 2016).
Wang, M.L., "Targeting BTK with Ibrutinib in Relapsed or Refractory Mantle-Cell Lymphoma." N Engl J Med., 369(6), Jun. 19, 2013. [Epub ahead of print].
Wassmer et al., "International Pediatric MS Study Group Global Members Symposium report", Neurology, 87(Suppl 2): S110-S116 (2016).
Weber et al., "B cell activation influences T cell polarization and outcome of anti-CD20 B cell depletion in CNS autoimmunity", Ann Neurol., 68(3), pp. 369-383 (Sep. 2010).
WebMD. 10 Ways to Prevent Psoriasis Flare-Ups. (2016) Web< http://www.webmd.com/skin-problems-and-treatments/psoriasis/prevent-flare-ups>.
WebMD. Multiple Sclerosis (MS)-Prevention. (2015) Web: < http://wwwv.webmd.com/multiple-sclerosis/tc/multiple-sclerosis-ms-prevention>.
Wermuth, Camille G., "Molecular Variation Based on Isosteric Replacements" in Chapter 13, The Practice of Medicinal Chemistry, Academic: 1996, pp. 203-237.
Wong et al., "Real-world validation of the 2017 McDonald criteria for pediatric MS", Neurol, 6:e528 (2019).
Wu et al., "Second-generation inhibitors of Bruton tyrosine kinase", J Hematol Oncol., 9(1), p. 80 (2016).
Xu et al., "RN486, a selective Bruton's tyrosine kinase inhibitor, abrogates immune hypersensitivity responses and arthritis in rodents", J Pharmacol Exp Ther, 341(1), pp. 90-103 (2012).
Yan et al., "Comparison of anti-acetylcholine receptor profiles between Chinese cases of adult- and juvenile-onset myasthenia gravis using cell-based assays", J Neuroimmunol., 349:577403 (Dec. 15, 2020).
Yeh et al., "Pediatric multiple sclerosis", Nat. Rev. Neurol., 5, pp. 621-631 (2009).
Yeshokumar et al., "Pediatric multiple sclerosis", Curr Opin Neurol., 30(3), pp. 216-221 (Jun. 2017).
Yi et al., "B cells in the pathophysiology of myasthenia gravis", Muscle Nerve, 57(2), pp. 172-184 (Feb. 2018).
Zavalishin et al., "Multiple sclerosis: modern concept of pathogenesis and pathogenetic treatment", Annals of Clinical and Experimental Neurology, 1(1), pp. 32-40 (2007) (English translation).
Zhao, et al., "The role of innate immunity in myasthenia gravis", Autoimmun Rev., 20(5):102800 (2021).
Zhong et al., "HLA in myasthenia gravis: From superficial correlation to underlying mechanism", Autoimmun Rev., 18(9):102349 (Sep. 2019).
Acalabrutinib [prescribing information]. Wilmington, DE: AstraZeneca Pharmaceuticals LP;2017 [Revised Oct. 2017; cited Aug. 12, 2021]. Available from:https://www.accessdata.fda.gov/drugsatfda_docs/label/2017/210259s000lbl.pdf.
Advani, et al., "Bruton tyrosine kinase inhibitor ibrutinib (PCI-32765) has significant activity in patients with relapsed/refractory B-cell malignancies." Journal of Clinical Oncology, 31, pp. 88-94 (2013).
Aguilar, C, "Ibrutinib-related bleeding: pathogenesis, clinical implications and management." Blood Coagul Fibrinolysis, 29(6), pp. 481-487 (Sep. 2018).
Alabbad, et al. "Monoclonal Antibody Based Therapies for Myasthenia Gravis." BioDrugs., 34(5), pp. 557-566 (Oct. 2020).
Alroughani et al., "Pediatric multiple sclerosis—a review", BMC Neurology, 18:27 (2018) (8 pages).
Amato et al, "Interrater reliability in assessing functional systems and disability on the Kurtzke scale in multiple sclerosis", Arch Neurol., 45(7), pp. 746-748 (Jul. 1988).

(56) References Cited

OTHER PUBLICATIONS

American Cancer Society. Can Non-Hodgkins Lymphoma Be Prevented? (2016) Web: https://www.cancer.org/cancer/non-hodgkin-lymphoma/causes-risks-prevention/prevention.html (3 pages).
Aragonès et al., "Prevalence of myasthenia gravis in the Catalan county of Osona", Neurologia., 32(1), pp. 1-5 (Jan.-Feb. 2017).
Arora, et al., "Role of Tyrosine Kinase Inhibitors in Cancer Therapy," J. Pharmacol. Exp. Ther., 2005, 315:971-979.
Auto-immune Diseases: Medlineplus (2014). Web: http://www.nlm.nih.gov/medlineplus/autoimmunediseases.html.
Azevedo et al., "Whole-brain atrophy: ready for implementation into clinical decision-making in multiple sclerosis?", Curr Opin Neurol., 29(3), pp. 237-242 (Jun. 2016).
Balto et al., "Accuracy and precision of smartphone applications and commercially available motion sensors in multiple sclerosis", Mult Scler J Exp Transl Clin (Mar. 4, 2016).
Banwell et al., "Incidence of acquired demyelination of the CNS in Canadian children", Neurology, 72(3), pp. 232-239 (Jan. 20, 2009). doi: 10.1212/01.wnl.0000339482. 84392.bd.
Banwell et al., "Multiple sclerosis in children: clinical diagnosis, therapeutic strategies, and future directions", Lancet Neurology, 6, pp. 887-902 (2007).
Barnett et al., "Measuring Clinical Treatment Response in Myasthenia Gravis", Neurol Clin, 36(2), pp. 339-353 (2018).
Barnett et al., "A conceptual framework for evaluating impairments in myasthenia gravis", PLoS One, 9(5), pp. 1-9 (2014).
Barnett et al., "Development and validation of the Myasthenia Gravis Impairment Index", Neurology, 87(9), pp. 879-886 (Aug. 30, 2016).
Barnett et al., "Myasthenia Gravis Impairment Index: Responsiveness, meaningful, change, and relative efficiency", Neurology, 5:89(23), pp. 2357-2364 (2017).
Barohn et al., "Reliability testing of the quantitative myasthenia gravis score", Ann N.Y. Acad Sci, 841, pp. 769-772 (1998).
Bar-Or et al., Clinical Perspectives on the Molecular and Pharmacological Attributes of Anti-CD20 Therapies for Multiple Sclerosis, CNS Drugs, 35(9), pp. 985-997 (Sep. 2021).
Barraud et al., "Clinical features and evolution of juvenile myasthenia gravis in a French cohort", Muscle Nerve, 57(4), pp. 603-609 (Apr. 2018).
Bedlack et al., "Quantitative myasthenia gravis score: Assessment of responsiveness and longitudinal validity", Neurology, vol. 64, pp. 1968-1970 (2005).
Benedict et al., "Characterizing cognitive function during relapse in multiple sclerosis", Mult Scler., 20(13), pp. 1745-1752 (Nov. 2014) doi: 10.1177/1352458514533229.
Benedict et al., "Improved cognitive outcomes in patients with relapsing-remitting multiple sclerosis treated with daclizumab beta: results from the DECIDE study", Mult Scler J, 24(6), pp. 795-804 (2018).
Berger, et al., "PML diagnostic criteria: consensus statement from the AAN Neuroinfectious Disease Section", Neurology, vol. 80, No. 15, pp. 1430-1438 (Apr. 9, 2013).
Bergsland et al., "Subcortical and Cortical Gray Matter Atrophy in a Large Sample of Patients with Clinically Isolated Syndrome and Early Relapsing-Remitting Multiple Sclerosis", Am J Neuroradiol, 33(8), pp. 1573-1578 (2012).
Berrih-Aknin, et al., "Myasthenia Gravis: a comprehensive review of immune dysregulation and etiological mechanisms", J Autoimmun., vol. 52, pp. 90-100 (Aug. 2014).
Bhaskaran, et al., "Pancreatic Effects of a Bruton's Tyrosine Kinase Small-molecule Inhibitor in Rats Are Strain-dependent", Toxicol Pathol., vol. 46(4), pp. 460-472 (Jun. 2018).
Blauth, et al., "The ins and outs of B cells in multiple sclerosis", Front. Immunol., vol. 6, p. 565 (Nov. 5, 2015).
Boiko et al., "Early onset multiple sclerosis: a longitudinal study", Neurology, 59, pp. 1006-1010 (2002).
Bornkamp et al., "Package 'DoseFinding': Planning and analyzing dose finding experiments," Version 0.9-16, CRAN. Jan. 4, 2018.
Breiner et al., "Epidemiology of myasthenia gravis in Ontario, Canada", Neuromuscul Disord., 26(1), pp. 41-46 (Jan. 2016).
Brenneman et al., "Mechanistic investigations of test article-induced pancreatic toxicity at the endocrine-exocrine interface in the rat", Toxicol Pathol., 42(1), pp. 229-242 (Jan. 2014).
Brittain, Harry, "Polymorphism in Pharmaceutical Solids, 2nd Edition", CRC Press, 2009 (229 pages).
Brown et al. "Incidence of and risk factors for major haemorrhage in patients treated with ibrutinib: An integrated analysis.", Br. J. Haematol., 184(4), pp. 558-569 ( Feb. 2019).
Bubuioc et al. "The epidemiology of myasthenia gravis.", J Med Life., 14(1), pp. 7-16 (Jan.-Mar. 2021).
Buoen, C., et al. "How first-time-in-human studies are being performed: a survey of phase I dose-escalation trials in healthy volunteers published between 1995 and 2004." J Clin Pharmacol. Oct. 2005, vol. 45, No. 10, pp. 1123-1136.
Burdick et al., "Confidence intervals on variance components.", Marcel Dekker, NY. 1992.
Burger J A, et al., "Targeting B cell receptor signalling in cancer: preclinical and clinical advances.", Nat Rev Cancer. 2018;18(3):148-67.
Bye et al., "Severe platelet dysfunction in NHL patients receiving ibrutinib is absent in patients receiving acalabrutinib", Blood Adv., 1(26), pp. 2610-2623 (Dec. 12, 2017).
Byrd et al., "Acalabrutinib (ACP-196) in relapsed chronic lymphocytic leukemia", N Engl J Med., 374(4), pp. 323-332 (2016).
Byrd et al., "Targeting BTK with Ibrutinib in Relapsed Chronic Lymphocytic Leukemia", N Engl J Med., 369(1), pp. 32-42 (Jun. 19, 2013).
Cadavid et al., "The EDSS-Plus, an improved endpoint for disability progression in secondary progressive multiple sclerosis", Multiple Sclerosis Journal, 23(1), pp. 94-105 (2017).
Caira, Mino R., "Crystalline Polymorphism of Organic Compounds", Topics in Current Chemistry, 198, pp. 163-208 (Jan. 1, 1998).
Carr et al., "A systematic review of population based epidemiological studies in Myasthenia Gravis", BMC Neurology, 10(46), pp. 1-9 (Jun. 18, 2010).
Case et al., "Accuracy of smartphone applications and wearable devices for tracking physical activity data", JAMA, 313(6), pp. 625-626.
Cavalcante et al., "Etiology of myasthenia gravis: innate immunity signature in pathological thymus", Autoimmun Rev., 12(9), pp. 863-874 (Jul. 2013).
Cavalcante et al., "Toll-like receptors 7 and 9 in myasthenia gravis thymus: amplifiers of autoimmunity?" Annals of the New York Academy of Science, Feb. 2018;1413(1):11-24.
Center for Drug Evaluation and Research, Summary Basis of Approval, Acalabrutinib, Application No. 210259Orig1s000, 2017.
Center for Drug Evaluation and Research, Summary Basis of Approval, Ibrutinib, Application No. 205552Orig1s000, 2013.
Turner et al., "Comparative CNS Pharmacology of Tolebrutinib Versus Other BTK Inhibitor Candidates for Treating MS", AAN 2023, Presentation 007 (13 pages).
Turner et al., "Comparative CNS Pharmacology of Tolebrutinib Versus Other BTK Inhibitor Candidates for Treating MS", Presented at the Americas Committee for Treatment and Research in Multiple Sclerosis (ACTRIMS) Forum, Feb. 24-26, 2022, West Palm Beach, FL, USA (1 page).
Turner, T.J., "Comparative CNS Pharmacology of Tolebrutinib Versus Other BTK Inhibitor Candidates for Treating MS", P162, Multiple Sclerosis Journal, 28: (1S), pp. 94-95 (2022).
Vermersch et al., "Bruton's Tyrosine Kinase Inhibitor Tolebrutinib in Patients With Progressive MS: Design of the Phase 3 PERSEUS and HERCULES Trials", EPO-455, Presented at the 7th Congress/2nd Virtual Congress of the European Academy of Neurology (EAN), Jun. 19-22, 2021 (1 page).
Vermersch et al., BTK Inhibitor Tolebrutinib in Patients With Progressive MS: Design of Phase 3PERSEUS and HERCULES Trials, EPO-455, European Journal of Neurology, 28 (Suppl. 1), p. 727 (2021).

(56) References Cited

OTHER PUBLICATIONS

Waldron, James, "Sanofi's tolebrutinib fails 2 of trio of phase 3 MS trials, but pharma still plans FDA filing", Fierce Biotech, Sep. 2, 2024 (3 pages).
WHO, "International Nonproprietary Names forPharmaceutical Substances (INN)", WHO Drug Information, List 84, vol. 34, No. 3, 2020 (115 pages).
WHO, "International Nonproprietary Names forPharmaceutical Substances (INN)", WHO Drug Information, Proposed List 112, vol. 33, No. 4, 2019 (139 pages).
Wiendl et al., "Baseline Characteristics in the Tolebrutinib Phase 3 Relapsing Multiple Sclerosis GEMINI 1 and 2 Trials", EPO-664, Presented at 9th Congress of the European Academy of Neurology (EAN), Jul. 1-4, 2023, Budapest, Hungary (1 page).
Wiendl et al., "EPO-664, Baseline Characteristics in the Tolebrutinib Phase 3 Relapsing Multiple Sclerosis GEMINI 1 and 2 Trials", EPO-224, European Journal of Neurology, 30 (Suppl. 1), pp. 649-742 (2023).
Wirak et al., "Bruton's Tyrosine Kinase Regulates Microglial Proinflammatory Pathways—Implications for Multiple Sclerosis", P134, Presented at the 9th Joint ECTRIMS-ACTRIMS Meeting; Milan, Italy; Oct. 11-13, 2023 (1 page).
Wirak et al., "Bruton's tyrosine kinase regulates microglial proinflammatory pathways—implications for multiple sclerosis", P134/2063, Multiple Sclerosis Journal, 29: (3S), p. 229 (2023).
Wynford-Thomas et al., "Neurological update: MOG antibody disease", Journal of Neurology, 266, pp. 1280-1286 (2019).
"ASENT2021 Annual Meeting Abstracts ED—Vink Robert; Bullock M. Ross," Neurotherapeutics, 18(3), pp. 2134-2151 (2021).
Blazier A., "Tolebrutinib Can Reverse Multiple Sclerosis Induced Cerebrospinal Fluid Proteomic Alterations", Multiple Sclerosis Journal, 29(3) supplement, p. 564 (2023).
Blazier, A., "Evaluating Large Scale Proteomic Changes in Cerebrospinal Fluid of Multiple Sclerosis Patients Treated with Tolebrutinib", Multiple Sclerosis, 29(2) supplement, pp. 26-27 (2023).
International Search Report and Written Opinion issued in International Application No. PCT/US2024/013658 on Jul. 31, 2024 (25 pages).
Iwanowski et al., "CXCL10 and CXCL13 chemokines in patients with relapsing remitting and primary progressive multiple sclerosis", Journal of Neurological Sciences, vol. 380, pp. 22-26 (2017).
Kuhle J., "Evobrutinib, a Bruton's tyrosine kinase inhibitor, decreases neurofilament light chain levels over 2.5 years of treatment in patients with relapsing multiple sclerosis", Multiple Sclerosis Journal, 28(3 Supplement), pp. 822-823 (2022).
Martynova, E., "Serum and Cerebrospinal Fluid Cytokine Biomarkers for Diagnosis of Multiple Sclerosis", Mediators of Inflammation, vol. 2020, pp. 1-10 (2020).
Nuesslein-Hildesheim, B., "Remibrutinib inhibits neuroflammation driven by B cells and myeloid cells in preclinical models of multiple sclerosis," Multiple Sclerosis, vol. 28, No. 3 supplement, pp. 220-221 (2022).
Puthenparampil, M., "Wide Cytokine Analysis in Cerebrospinal Fluid at Diagnosis Identified CCL-3 as a Possible Prognostic Factor for Multiple Sclerosis," Frontiers in Immunology, vol. 11, p. 174 (2020).
Yang et al., "Current and Future Biomarkers in Multiple Sclerosis", International Journal of Molecular Sciences, 23 (11), p. 5877 (2022).
Sanofi Press Release: "Tolebrutinib meets primary endpoint in HERCULES phase 3 study, the first and only to show reduction in disability accumulation in non-relapsing secondary progressive multiple sclerosis", 3 pages (Sep. 2, 2024).
Sanofi Press Release: "Tolebrutinib demonstrated a 31% delay in time to onset of confirmed disability progression in non-relapsing secondary progressive multiple sclerosis phase 3 study", 4 pages (Sep. 20, 2024).
ClinicalTrials.gov, "Nonrelapsing Secondary Progressive Multiple Sclerosis (NRSPMS) Study of Bruton's Tyrosine Kinase (BTK) Inhibitor Tolebrutinib (SAR442168)(HERCULES)(HERCULES)", NCT04411641, Record History Tab, Version 32, Last Updated Jul. 2, 2025 (90 pages).
ClinicalTrials.gov, "Primary Progressive Multiple Sclerosis (PPMS) Study of Bruton's Tyrosine Kinase (BTK) Inhibitor Tolebrutinib (SAR442168) (PERSEUS) (PERSEUS)", NCT04458051, Record History Tab, Version 42, Last Updated Jan. 13, 2025 (39 pages).
ClinicalTrials.gov, "Primary Progressive Multiple Sclerosis (PPMS) Study of Bruton's Tyrosine Kinase (BTK) Inhibitor Tolebrutinib (SAR442168) (PERSEUS) (PERSEUS)", NCT04458051, Record History Tab, Version 25, Last Updated Jan. 13, 2025 (51 pages).
ClinicalTrials.gov, "Primary Progressive Multiple Sclerosis (PPMS) Study of Bruton's Tyrosine Kinase (BTK) Inhibitor Tolebrutinib (SAR442168) (PERSEUS) (PERSEUS)", NCT04458051, Record History Tab, Version 43, Last Updated Jan. 13, 2025 (38 pages).
ClinicalTrials.gov, "Primary Progressive Multiple Sclerosis (PPMS) Study of Bruton's Tyrosine Kinase (BTK) Inhibitor Tolebrutinib (SAR442168) (PERSEUS) (PERSEUS)", NCT04458051, Record History Tab, Version 1, Last Updated Jan. 13, 2025 (15 pages).
ClinicalTrials.gov, "Primary Progressive Multiple Sclerosis (PPMS) Study of Bruton's Tyrosine Kinase (BTK) Inhibitor Tolebrutinib (SAR442168) (PERSEUS) (PERSEUS)", NCT04458051, Record History Tab, Version 11, Last Updated Jan. 13, 2025 (22 pages).
ClinicalTrials.gov, "Primary Progressive Multiple Sclerosis (PPMS) Study of Bruton's Tyrosine Kinase (BTK) Inhibitor Tolebrutinib (SAR442168) (PERSEUS) (PERSEUS)", NCT04458051, Record History Tab, Version 39, Last Updated Jan. 13, 2025 (56 pages).
ClinicalTrials.gov, "Relapsing Forms of Multiple Sclerosis (RMS) Study of Bruton's Tyrosine Kinase (BTK) Inhibitor Tolebrutinib (SAR442168) (GEMINI 2) (GEMINI 2)", NCT04410991, Record History Tab, Version 1, Last Updated Jul. 2, 2025 (16 pages).
ClinicalTrials.gov, "Relapsing Forms of Multiple Sclerosis (RMS) Study of Bruton's Tyrosine Kinase (BTK) Inhibitor Tolebrutinib (SAR442168) (GEMINI 1)(GEMINI 1)", NCT04410978, Records History Tab, Version 17, Last Updated Jul. 2, 2025 (24 pages).
ClinicalTrials.gov, "Relapsing Forms of Multiple Sclerosis (RMS) Study of Bruton's Tyrosine Kinase (BTK) Inhibitor Tolebrutinib (SAR442168) (Gemini 2) (GEMINI 2)", NCT04410991, Record History Tab, Version 26, Last Updated Jul. 2, 2025 (33 pages).
ClinicalTrials.gov, "Relapsing Forms of Multiple Sclerosis (RMS) Study of Bruton's Tyrosine Kinase (BTK) Inhibitor Tolebrutinib (SAR442168) (GEMINI 1)(GEMINI 1)", NCT04410978, Records History Tab, Version 26, Last Updated Jul. 2, 2025 (34 pages).
ClinicalTrials.gov, "Relapsing Forms of Multiple Sclerosis (RMS) Study of Bruton's Tyrosine Kinase (BTK) Inhibitor Tolebrutinib (SAR442168) (GEMINI 1)(GEMINI 1)", NCT04410978, Records History Tab, Version 44, Last Updated Jul. 2, 2025 (75 pages).
ClinicalTrials.gov, "Relapsing Forms of Multiple Sclerosis (RMS) Study of Bruton's Tyrosine Kinase (BTK) Inhibitor Tolebrutinib (SAR442168) (GEMINI 2) (GEMINI 2)", NCT04410991, Record History Tab, Version 40, Last Updated Jul. 2, 2025 (72 pages).
ClinicalTrials.gov, "Relapsing Forms of Multiple Sclerosis (RMS) Study of Bruton's Tyrosine Kinase (BTK) Inhibitor Tolebrutinib (SAR442168) (GEMINI 1)(GEMINI 1)", NCT04410978, Records History Tab, Version 1, Last Updated Jul. 2, 2025 (17 pages).
ClinicalTrials.gov, "Relapsing Forms of Multiple Sclerosis (RMS) Study of Bruton's Tyrosine Kinase (BTK) Inhibitor Tolebrutinib (SAR442168) (GEMINI 2) (GEMINI 2)", NCT04410991, Record History Tab, Version 18, Last Updated Jul. 2, 2025 (23 pages).
ClinicalTrials.gov, "Study of Excretion Balance and Pharmacokinetics of [14C]-SAR442168 in Healthy Male Subjects", NCT04171310, Record History Tab, Version 1, Last Updated Apr. 25, 2022 (9 pages).
ClinicalTrials.gov, "Study to Assess the Plasma Concentration of Tolebrutinib Given as a Tablet to Adult Participants With Mild Hepatic Impairment Compared to Participants With Normal Hepatic Function", NCT05283915, Record History Tab, Last Updated Jan. 15, 2025 (11 pages).
ClinicalTrials.gov, "Study to Assess the Plasma Concentration of Tolebrutinib Given as a Tablet to Adult Participants with Renal Impairment Compared to Healthy Participants", NCT05282030, Version 5, Record History Tab, Last Updated Feb. 6, 2025 (12 pages).

(56) References Cited

OTHER PUBLICATIONS

ClinicalTrials.gov, "Study to Assess the Plasma Concentration of Tolebrutinib Given as a Tablet to Adult Participants With Renal Impairment Compared to Healthy Participants", NCT05282030, Record History Tab, Version 1, Last Updated Feb. 6, 2025 (11 pages).
ClinicalTrials.gov, "Tolebrutinib, a Brain-penetrant Bruton's Tyrosine Kinase Inhibitor, for the Modulation of Chronically Inflamed White Matter Lesions in Multiple Sclerosis", NCT04742400, Record History Tab—V157, Last Updated Aug. 13, 2024 (29 pages).
ClinicalTrials.gov, "Tolebrutinib, a Brain-penetrant Bruton's Tyrosine Kinase Inhibitor, for the Modulation of Chronically Inflamed White Matter Lesions in Multiple Sclerosis", NCT04742400, Record History Tab, Version 145, Last Updated Aug. 13, 2024 (29 pages).
ClinicalTrials.gov, "Tolebrutinib, a Brain-penetrant Bruton's Tyrosine Kinase Inhibitor, for the Modulation of Chronically Inflamed White Matter Lesions in Multiple Sclerosis", NCT04742400, Record History Tab, Version 1, Last Updated Aug. 13, 2024 (27 pages).
Confaverux et al., "Oral terifl unomide for patients with relapsing multiple sclerosis (TOWER): a randomised, double-blind, placebocontrolled, phase 3 trial", Lancet Neurol, 13, pp. 247-256 (2014).
Correale, J., "BTK inhibitors as potential therapies for multiple sclerosis", The Lancet Neurology, 20, pp. 689-691 (Sep. 2021).
Dal-Bianco et al., "Chronic active lesions in multiple sclerosis: classification, terminology, and clinical significance", The Adv Neurol Disord, 17, pp. 1-25 (2024).
Disano et al., "Intrathecally produced CXCL13: A predictive biomarker in multiple sclerosis", Multiple Sclerosis Journal-Experimental, Translational and Clinical, pp. 1-12 (Oct.-Dec. 2020).
EU Clinical Trials Register, "A study to investigate long-term safety and tolerability of tolebrutinib in particpants with multipe sclerosis", EUCT 2023-503631-18-01, 2023 (141 pages).
EU Clinical Trials Register, "Clinical trial results: A Phase 3, randomized, double-blind efficacy and safety study comparing SAR442168 to teriflunomide (Aubagio®) in participants with relapsing forms of multiple sclerosis (GEMINI 2)", v1, EU-CTR2020-000644-55, Jul. 6, 2025 (32 pages).
EU Clinical Trials Register, "Clinical trial results: A Phase 3, randomized, double-blind, efficacy and safety study comparing SAR442168 to placebo in participants with nonrelapsing secondary progressive multiple sclerosis (HERCULES)", v1, 2020-000647-30, Jul. 6, 2025 (63 pages).
EU Clinical Trials Register, "Primary Progressive Multiple Sclerosis (PPMS) Study of Bruton's Tyrosine Kinase (BTK) Inhibitor tolebrutinib (SAR442168)(PERSEUS)", v1, 2024-514495-41-00, 2024 (91 pages).
EU Clinical Trials Register, Clinical trial results: A Phase 3, randomized, double-blind efficacy and safety study comparing SAR442168 to teriflunomide (Aubagio®) in participants with relapsing forms of multiple sclerosis (GEMINI 1), v1, EU-CTR2020-000637-41, Jul. 6, 2025 (35 pages).
European Medical Journal, "Sanofi's MS drug delivers surprising Phase III results", obtained from https://emjreviews.com/en-us/emj-gold/news/sanofis-ms-drug-delivers-suprising-phase-iii-results/, Sep. 3, 2024 (5 pages).
Fier et al., "A Multifunctional Reagent Designed for the Site-Selective Amination of Pyridines", Journal of the American Chemical Society, 142(19), pp. 8614-8618 (May 13, 2020).
Fox et al., "(DMT37) Baseline Characteristics in the Tolebrutinib Phase 3 Primary Progressive Multiple Sclerosis PERSEUS Clinical Trial", International Journal of MS Care, 27(1): 42 (May/Jun. 2025).
Fox et al., "(PLA-A4) Disability Outcomes in Tolebrutinib Phase 3 Trials in Nonrelapsing Secondary Progressive Multiple Sclerosis and Relapsing Multiple Sclerosis", International Journal of MS Care, 27(1), pp. 5-6 (May/Jun. 2025).
Fox et al., "Baseline Characteristics in the Tolebrutinib Phase 3 Non-Relapsing Secondary Progressive Multiple Sclerosis (nrSPMS) HERCULES Clinical Trial", P1476/1293, Multiple Sclerosis Journal, 29: (3S), pp. 938-939 (2023).
Fox et al., "Baseline Characteristics in the Tolebrutinib Phase 3 Non-Relapsing Secondary Progressive Multiple Sclerosis (nrSPMS) HERCULES Clinical Trial", P1476, Presented at the 9th Joint ECTRIMS-ACTRIMS Meeting; Milan, Italy; Oct. 11-13, 2023 (1 page).
Fox et al., "Baseline Characteristics in the Tolebrutinib Phase 3 Primary Progressive Multiple Sclerosis PERSEUS Clinical Trial", DMT37, Presented at the Consortium of Multiple Sclerosis Centers Annual Meeting, May 28-31, 2025; Phoenix, Arizona (1 page).
Fox et al., "Characteristics and Outcomes of COVID-19 Cases from the Long-term Extension Study of Tolebrutinib in Patients with Relapsing MS", P126, Presented at the Americas Committee for Treatment and Research in Multiple Sclerosis (ACTRIMS) Forum, Feb. 24-26, 2022, West Palm Beach, FL, USA (1 page).
Fox et al., "Characteristics and Outcomes of COVID-19 Cases from the Long-term Extension Study of Tolebrutinib in Patients with Relapsing MS", P126, Multiple Sclerosis Journal, 28: (1S), p. 77 (2022).
Fox et al., "Disability Outcomes in Tolebrutinib Phase 3 Trials in Non-Relapsing Secondary Progressive Multiple Sclerosis and Relapsing Multiple Sclerosis", Presentation PLA-A4, Presented at the Consortium of Multiple Sclerosis Centers Annual Meeting, May 28-31, 2025; Phoenix, Arizona (12 pages).
Fox et al., "Efficacy and Safety of Tolebrutinib Versus Placebo in Non-Relapsing Secondary Progressive Multiple Sclerosis: Results from the Phase 3 HERCULES Trial", O136/4027, Multiple Sclerosis Journal, 30: (3S), pp. 1146-1147 (2024).
Fox et al., "Efficacy and Safety of Tolebrutinib Versus Placebo in Non-Relapsing Secondary Progressive Multiple Sclerosis: Results From the Phase 3 HERCULES Trial", Presentation #0136. Presented at the 40th Congress of the European Committee for Treatment and Research in Multiple Sclerosis; Sep. 18-20, 2024; Copenhagen, Denmark (15 pages).
Fox et al., "MRI, efficacy, and safety of tolebrutinib in patients with highly active disease (HAD): 2-year data from the phase 2b Long-term safety (LTS) Study", P292, Multiple Sclerosis Journal, 28: (3S), p. 331 (2022).
Fox et al., "MRI, Efficacy, and Safety of Tolebrutinib in Patients with Highly Active Disease: 2-Year Data from the Phase 2b Long-Term Safety Study", P292, Presented at the 38th Congress of the European Committee for Treatment and Research in Multiple Sclerosis (ECTRIMS); Amsterdam, the Netherlands; Oct. 26-28, 2022 (1 page).
Fox et al., "Tolebrutinib in Nonrelapsing Secondary Progressive Multiple Sclerosis", The New England Journal of Medicine, Apr. 8, 2025 (DOI: 10.1056/NEJMoa2415988) (10 pages).
Francesco et al., "PRN2246, a potent and selective blood brain barrier penetrating BTK inhibitor, exhibits efficacy in central nervous system immunity", ECTRIMS, P072 (1 page) (2017).
Gaitan et al., "Primary Outcome of a Phase 2 Clinical Trial of Tolebrutinib, a Brain-Penetrant BTK Inhibitor, for the Modulation of Chronically Inflamed White Matter Lesions in MS", National Institute of Neurological Disorders and Stroke, ACTRIMS, 2024 (16 pages).
Gaitan et al., "Primary Outcome of a Phase 2 Clinical Trial of Tolebrutinib, a Brain-Penetrant BTK Inhibitor, for the Modulation of Chronically Inflamed White Matter Lesions in MS", LB1.2, Multiple Sclerosis Journal, ACTRIMS, 30:(IS), p. 11 (2024).
Giovannoni, G., aka Prof G, "Breaking news—smouldering MS or the "real MS" becomes a tractable problem.", X, Sep. 2, 2024 (1 page).
Noêl, R. et al., "Synthesis and SAR of 4-(pyrazol-3-yl)-pyridines as novel c-jun N-terminal kinase inhibitors" Bioorganic & Medicinal Chemistry Letters, vol. 21, Issue 9, (2011) 2732-2735.
O'Connell et al., "Management of Juvenile Myasthenia Gravis", Front. Neurol., 11, p. 743 (2020).
O'Connor et al., "Randomized Trial of Oral Teriflunomide for Relapsing Multiple Sclerosis", N Engl J Med, 365, pp. 1293-1303 (2011).
Oh et al., "Emerging therapies to target CNS pathophysiology in multiple sclerosis", Nature Review Neurology, 18(8), pp. 466-475 (Jun. 13, 2022).

(56) References Cited

OTHER PUBLICATIONS

Oh et al., "Safety and clinical outcomes from the long-term extension study of tolebrutinib in patients with relapsing Multiple Sclerosis: 18-month results", Neurology, 98(18S, pp. 20220424-20220426 (May 3, 2022).
Okun et al., "Involvement of Fc receptors in disorders of the central nervous system", Neuromolecular Med., 12(2), pp. 164-178 (2010).
Online "https://www.chemicalbook.com/Chemical ProductProperty_EN_CB6195326.htm" dated by google to Oct. 1, 2014, Accessed Jun. 18, 2020 (4 pages).
Otallah et al., "Pediatric Multiple Sclerosis: an Update", Curr Neurol Neurosci Rep., 18(11), p. 76 (Sep. 18, 2018).
Owens et al., "Phase 1 clinical trial evaluating safety, exposure and pharmacodynamics of BTK inhibitor tolebrutinib (PRN2246, SAR442168)", Clin Transl Sci., 00, pp. 1-9 (2021).
Panichi Zanin Ferreira et al., "Disease progression and oxidative stress are associated with higher serum ferritin levels in patients with multiple sclerosis", J Neurol Sci, 373, pp. 236-241 (Epub Dec. 27, 2016).
Parr et al., "How common is childhood myasthenia? The UK incidence and prevalence of autoimmune and congenital myasthenia", Arch Dis Child, 99(6), pp. 539-542 (Jun. 2014).
Patani, G., Bioisosterism: A Rational Approach in Drug Design. Chem. Rev. 1996, vol. 96, No. 8, pp. 3147-3176.
Pedersen et al., "Late-onset myasthenia not on the increase: a nationwide register study in Denmark", 1996-2009. Eur J Neurol., 20, pp. 309-314 (2013).
Pellerin et al., "MOG autoantibodies trigger a tightly-controlled FcR and BTK-drive microglia proliferative response", Brain, 144(8), pp. 2361-2374 (Sep. 4, 2021).
Pennington et al., "The Necessary Nitrogen Atom: A Versatile High-Impact Design Element for Multiparameter Optimization," J. Med. Chem., ePub Feb. 8, 2017, 28 pages, DOI: 10.1021/acs.jmedchem 6b01807.
Peragallo JH., "Pediatric Myasthenia Gravis", Semin Pediatr Neurol., 24(2), pp. 116-121 (May 2017).
Phillips et al., "Sustained improvement in Expanded Disability Status Scale as a new efficacy measure of neurological change in multiple sclerosis: treatment effects with natalizumab in patients with relapsing", Multiple Sclerosis Journal, 17(8), pp. 970-979 (2011).
Popperud et al., "Juvenile myasthenia gravis in Norway: HLA-DRB1_04:04 is positively associated with prepubertal onset", PLoS One, 12(10): e0186383 (2017).
Press Release: "Sanofi to acquire Principia Biopharma", 6 pages (Aug. 17, 2020).
Ragheb et al., "B-Cell-Activating Factor and Autoimmune Myasthenia Gravis", Autoimmune Dis., 2011; 939520.
Rahmanzadeh R, et al., "Multiple sclerosis pathogenesis: missing pieces of an old puzzle.", Rev Neurosci. Jun. 8, 2018. pii: /j/revneuro.ahead-ofprint/revneuro-2018-0002/revneuro-2018-0002.XML. doi: 10.1515/revneuro-2018-0002.
Raisch et al., "Detection of cases of progressive multifocal leukoencephalopathy associated with new biologicals and targeted cancer therapies from the FDA's adverse event reporting system", Expert Opin Drug Saf., 15(8), pp. 1003-1011 (2016).
Ramanujam et al., "Utilizing twins concordance rates to infer the predisposition to myasthenia gravis", Twin Res. Hum. Genet., 13, pp. 129-136 (2011).
Rankin et al., "Selective inhibition of BTK prevents murine lupus and antibody-mediated glomerulonephritis", J Immunol., 191(9), pp. 4540-4550 (2013).
Rasche et al., "MRI Markers and Functional Performance in Patients With CIS and MS: A Cross-Sectional Study", Front Neurol, vol. 9(718), pp. 1-12 (2018).
Reich et al., "Safety and efficacy of tolebrutinib, an oral brain-penetrant BTK inhibitor, in relapsing multiple sclerosis: a phase 2b, randomised, double-blind, placebo-controlled trial", The Lancet Neurology, 20(9), pp. 729-738 (Sep. 1, 2021).
Renoux et al., "Natural History of Multiple Sclerosis with Childhood Onset", New England Journal of Medicine, 356, pp. 2603-2613 (2007).
Renoux et al., "The natural history of multiple sclerosis with childhood onset", Clin Neurol Neurosug., Nov. 2008;110(9), pp. 897-904. doi 10.1016/j.clineuro.2008.04.009. Epub Jun. 4, 2008.
Rigg et al., "Oral administration of Bruton's tyrosine kinase inhibitors impairs GPVI-mediated platelet function", Am J Physiol Cell Physiol., 310(5), pp. C373-C380 (Mar. 2016).
Robinet et al., "Review on Toll-Like Receptor Activation in Myasthenia Gravis: Application to the Development of New Experimental Models", Clin Rev Allergy Immunol., 52(1), pp. 133-147 (Feb. 2017).
Roschewski et al., "Inhibition of Burton tyrosine kinase in patients with severe COVID-19", Sci. Immunol. 10.1126/sciimmunol.abd0110 (2020).
Rovaris et al., "MRI markers of destructive pathology in multiple sclerosis-related cognitive dysfunction", Journal of the Neurological Sciences 245(1-2), pp. 111-116 (2006).
Rudko et al., "Monitoring increased iron levels in multiple sclerosis using MRI", Future Neurology, 9(4), pp. 387-391 (Jul. 1, 2014).
Sanders, D., et al., "International consensus guidance for management of myasthenia gravis: Executive summary", Neurology., 87(4), pp. 419-425 (Jul. 26, 2016).
Scalfari et al., "Onset of secondary progressive phase and long-term evolution of multiple sclerosis", Neurol Neurosurg Psychiatry., pp. 67-75 (2013).
Scalfari, et al., "Mortality in patients with multiple sclerosis", Neurology, 81, pp. 184-192 (2013).
Scheers et al., "Absorption, Metabolism, and Excretion of Oral 14C Radiolabeled Ibrutinib: An Open-Label, Phase 1, Single-Dose Study in Healthy Men", Drug Metab Dispos, vol. 43, pp. 289-207 (2015).
Schutt, et al., "BTK knockout rat model demonstrates rat-specific BTK inhibitor-related pancreatic pathology is on-target and unlikely to be relevant for humans [abstract 70]", Presented at 35th Annual Symposium of the Society of Toxicologic Pathology; Jun. 26-29, 2016; San Diego, CA. p. 77.
Selcen et al., "High-dose intravenous immunoglobulin therapy in juvenile myasthenia gravis", Pediatr Neurol, 22, pp. 40-43 (2000).
Sengupta et al., "MicroRNA and mRNA expression associated with ectopic germinal centers in thymus of myasthenia gravis", PLoS One, 13(10):e0205464 (Oct. 11, 2018).
Sfagos et al., "Serum ferritin, transferrin and soluble transferrin receptor levels in multiple sclerosis patients", Multiple Sclerosis Journal, 11(3), pp. 272-275 (Jun. 1, 2005).
Shatzel et al., "Ibrutinib-associated bleeding: pathogenesis, management and risk reduction strategies", J Thromb Haemost., 15(5), pp. 835-847., Epub Mar. 27, 2017. (May 2017).
Shi et al., "Purine derivatives as potent Bruton's tyrosine kinase (BTK) inhibitors for autoimmune diseases", Bioorganic & Medicinal Chemistry Letters, 24, pp. 2206-2211 (2014).
Sibaud et al., "Dermatological Toxicities of Bruton's Tyrosine Kinase Inhibitors", Am. J. Clin. Dermatol., 21, pp. 799-812 (2020).
Sideras et al., "Molecular and cellular aspects of X-linked agammaglobulinemia",, Adv Immunol., 59, pp. 135-223 (1995).
Smith P F et.al., "Phase 1 clinical trial of PRN2246 (SAR441268), a covalent BTK inhibitor demonstrates safety, CNS exposure and therapeutic levels of BTK occupancy", Database accession No. EMB 628003781 abstract & Multiple Sclerosis Journal Apr. 1, 2019 Sage Publications LTD NLD, vol. 25, No. Supplement 1, Apr. 1, 2019 (Apr. 1, 2019), pp. 52 CONF Feb. 28, 2019 to Mar. 2, 2019 Dallas, TX—4th Annual.
Sobieszczuk et al., "Myasthenia Gravis in Poland: National Healthcare Database Epidemiological Study", Neuroepidemiology, 19, pp. 1-8 (Feb. 2021).
Sormani et al., "Magnetic resonance imaging as a potential surrogate for relapses in multiple sclerosis: a meta-analytic approach.", Ann Neurol.; 65(3), pp. 268-275 (2009).
Sormani et al., "MRI lesions as a surrogate for relapses in multiple sclerosis: a meta analysis of randomised trials", Lancet Neurol., 12(7), pp. 669-676 (Jul. 2013).

(56) References Cited

OTHER PUBLICATIONS

Sormani et al., "Surrogate endpoints for EDSS worsening in multiple sclerosis a meta-analytic approach.", Neurology.; 75(4), pp. 302-309 (2010).
FDA Center for Drug Evaluation and Research. In Vitro Drug Interaction Studies—Cytochrome P450 Enzyme- and Transporter-Mediated Drug Interactions Guidance for Industry. Jan. 2020.
FDA Guidance for Industry: Estimating the maximum safe starting dose in initial clinical trials for therapeutics in adult healthy volunteers. Jul. 2005.
Fischer J S, et al., "The Multiple Sclerosis Functional Composite Measure (MSFC): an integrated approach to MS clinical outcome assessment. National MS Society Clinical Outcomes Assessment Task Force.", Mult Scler. 1999;5(4):244-50.
Francesco M R et.al, "PRN2246, a potent and selective blood brain barrier penetrating BTK inhibitor, exhibits efficacy in central nervous system immunity", Database accession No. EMB-619358129abstract & Multiple Sclerosis Journal Oct. 1, 2017 Sage Publications Ltd NLD, vol. 23, No. 3, Supplement 1, Oct. 1, 2017 (Oct. 1, 2017), pp. 511; CONF Oct. 25, 2017 to Oct. 28, 2017 Paris—7th Joint.
Fu et al., "Ocular toxicities associated with targeted anticancer agents: an analysis of clinical data with management suggestions", Oncotarget, 8(35), pp. 58709-58727 (May 2017).
Futatani et al., "Bruton's tyrosine kinase is present in normal platelets and its absence identifies patients with X-linked agammaglobulinaemia and carrier females", Br J Haematol., 114(1), pp. 141-149 (2001).
Ghezzi et al., "Long-Term Effect of Immediate Versus Delayed Fingolimod Treatment in Young Adult Patients with Relapsing-Remitting Multiple Sclerosis: Pooled Analysis from the Freedoms/Freedoms II Trials", Neurology and Therapy, 8, pp. 461-475 (2019).
Ghezzi et al., "Multiple sclerosis in childhood: clinical features of 149 cases", Multiple Sclerosis, 3, pp. 443-446 (1997).
Gilhus et al., "Myasthenia gravis", Nat Rev Dis Primers., 5(30), pp. 1-19 (2019).
Gilhus et al., "Myasthenia gravis: subgroup classification and therapeutic strategies", Lancet Neurol., 14(10), pp. 1023-1036 (Oct. 2015).
Giovannoni et al., "The COVID-19 pandemic and the use of MS disease-modifying therapies" [published online ahead of print, Mar. 27, 2020]. Mult Scler Relat Disord., vol. 39, 102073 (Apr. 2020).
Goldman et al., "Oral Bruton tyrosine kinase inhibitors block activation of the platelet Fc receptor CD32a (FcγRIIA): a new option in HIT?", Thrombosis and hemostasis, 3(23_, pp. 4021-4033, Electronic resource, URL: https://ashpublications.org/bloodadvances/article/3/23/4021/429246 /Oral-Bruton-tyrosine-kinase-inhibitors-block, date of access Apr. 22, 2024, p. 2028 right col. par. 1.
Gough et al., "Assessment of dose proportionality: report from the statisticians in the pharmaceutical industry / pharmacokinetics UK joint working party", Drug Information J, 29, pp. 1039-1048 (1995).
Harding et al., "Modelling the Natural History of Primary Progressive Multiple Sclerosis", J Neurol Neurosurg Psychiatry, 86(1), pp. 13-19 (2014).
Hata et al., "Involvement of Bruton's tyrosine kinase in FcepsilonRI-dependent mast cell degranulation and cytokine production", J Exp Med., 187(8), pp. 1235-1247 (1998).
Hauser et al., "B-Cell Depletion with Rituximab in Relapsing-Remitting Multiple Sclerosis", N Engl J Med., 358, pp. 676-688 (2008).
Hauser, SL, et al., "Ocrelizumab versus Interferon Beta-1a in Relapsing Multiple Sclerosis." N Engl J Med. 2017;376(3):221-34. Epub Dec. 21, 2016.
Hehir et al., "Generalized Myasthenia Gravis: Classification, Clinical Presentation, Natural History, and Epidemiology", Neurol Clin., 36(2), pp. 253-260 (May 2018).
Hemmer B, et. al., "Immunopathogenesis and immunotherapy of multiple sclerosis.", Nat Clin Pract Neurol. 2006;2(4):201-11.
Hemmer B, et. al., "Role of the innate and adaptive immune responses in the course of multiple sclerosis.", Lancet Neurol. 2015;14(4):406-19.
Holcmann et al., "Mechanisms underlying skin disorders induced by EGFR inhibitors", Mol Cell Oncol., 2(4):e1004969 (Jun. 2015).
Honigberg et al., "The Bruton tyrosine kinase inhibitor PCI-32765 blocks B-cell activation and is efficacious in models of autoimmune disease and B-cell malignancy", Proc. Natl Acad Sci USA, 107(29), pp. 13075-13080 (Jul. 20, 2010).
Horwood et al., "Bruton's tyrosine kinase is required for lipopolysaccharide induced tumor necrosis factor alpha production", J Exp Med, 197(12), pp. 1603-1611 (2003).
Howard et al., "QMG and MG-ADL Correlations: Study of Eculizumab Treatment of Myasthenia Gravis", Muscle & Nerve, 56(2), pp. 328-330 (Aug. 2017).
Howard et al., "Safety and efficacy of eculizumab in anti-acetylcholine receptor antibody-positive refractory generalized myasthenia gravis (REGAIN): a phase 3, randomised, double-blind, placebo-controlled, multicentre study", Lancet Neurol., 16(12), pp. 976-986 (Dec. 2017).
Huang et al., "Clinical characteristics of juvenile myasthenia gravis in southern China", Front Neurol., 9, p. 77 (2018).
Hundelshausen et al., "Bleeding by Bruton tyrosine kinase-inhibitors: Dependency on drug type and disease", Cancers, 13(5), p. 1103 (Jan. 2021).
Hutcheson et al., "Modulating proximal cell signaling by targeting Btk ameliorates humoral autoimmunity and end-organ disease in murine lupus", Arthritis Res Ther., 14: R243 (2012).
Ibrahim et al., "The power prior: theory and applications", Statist. Med., 34, pp. 3724-3749 (2015).
Ibrutinib [prescribing information]. Horsham, PA: Janssen Biotech, Inc.; 2013 [Revised Jan. 2015; cited Aug. 12, 2021]. Available from: https://www.accessdata.fda.gov/drugsatfda_docs/label/2015/205552s002lbl.pdf.
Imbruvica [package insert]. Pharmacyclics, Inc., Sunnyvale, CA; 2017.
Ingle et al., "Magnetic resonance imagin in primary progressive multiple sclerosis", Journal of Rehabilitation Research and Development, 39(2), pp. 261-272 (Mar./Apr. 2002).
International Preliminary Report on Patentability issued in International Application No. PCT/CN2022/096779 on Nov. 21, 2023 (12 pages).
International Search Report and Written Opinion in corresponding International Patent Application No. PCT/US2021/013883, mailed Apr. 28, 2021 (12 pages).
International Search Report and Written Opinion issued in International Application No. PCT/CN2021/132028, dated Feb. 18, 2022 (English translation provided) (2 pages).
International Search Report and Written Opinion issued in International Application No. PCT/US2022/053479 on Apr. 11, 2023 (13 pages).
International Search Report and Written Opinion issued in International Application No. PCT/US2023/022042 on Aug. 11, 2023 (13 pages).
International Search Report and Written Opinion issued in International Application No. PCT/US2023/025808 on Oct. 2, 2023 (24 pages).
International Search Report and Written Opinion issued in International Application No. PCT/US2023/026526 on Oct. 12, 2023 (12 pages).
International Search Report and Written Opinion issued in International Application No. PCT/US2023/034655 on Feb. 2, 2024 (13 pages).
International Search Report and Written Opinion issued in International Application No. PCT/US2023/084784 on Mar. 18, 2024 (17 pages).
International Search Report and Written Opinion mailed Aug. 16, 2016, issued in corresponding International Application No. PCT/US2016/035588 (9 pages).
International Search Report for International Application No. PCT/CN2016/084057, mailed Sep. 2, 2016 (4 pages) (English translation).

(56) References Cited

OTHER PUBLICATIONS

Irwin, S., "Comprehensive observational assessment: Ia. A systematic, quantitative procedure for assessing the behavioral and physiologic state of the mouse", Psychopharmacologia, 13(3), pp. 222-257 (1968).
Itachaki et al., "Experience with ibrutinib for first-line use in patients with chronic lymphocytic leukemia", Ther Adv Hematol., 9(1), pp. 3-19 (Jan. 2018).
Jaretzki et al., "Myasthenia gravis: recommendations for clinical research standards. Task Force of the Medical Scientific Advisory Board of the Myasthenia Gravis Foundation of America", Neurology, 55(1), pp. 16-23 (Jul. 12, 2000).
Johnson, "Modelling approaches to dose estimation in children", Br J Clin Pharmacol, 59(6), pp. 663-669 (2005).
Kalincik et al., "Treatment effectiveness of alemtuzumab compared with natalizumab, fingolimod, and interferon beta in relapsing-remitting multiple sclerosis: a cohort study", Lancet Neurol, 16, pp. 271-281 (2017).
Kaminski, "Treatment of Myasthenia Gravis. In: Kaminski HJ, Kusner LL, editors", Current Clinical Neurology: Myasthenia Gravis and Related Disorders 3rd edition, pp. 169-187 (2018).
Kapoor et al., "Effect of natalizumab on disease progression in secondary progressive multiple sclerosis (ASCEND): a phase 3, randomised, double-blind, placebo-controlled trial with an open-label extension", Lancet Neurol, 17: 405-415 (2018).
Bader, Saskia, "Invitation to Pay Additional Fees and, Where Applicable, Protest Fee with Annex to Form PCT/ ISA/206 Communication Relating to the Results of the Partial International Search Report", mailed in International Application No. PCT/ US2025/043964 on Dec. 16, 2025 (12 pages).
Baharlou, S., "International Preliminary Report on Patentability", issued in International Application No. PCT/ US2023/022042 on Nov. 7, 2024 (9 pages).
Baharlou, S., "International Preliminary Report on Patentability", issued in International Application No. PCT/ US2023/025170 on Dec. 10, 2024 (6 pages).
Bar-Or et al., "Blood Immunoglobulin Levels and Immune Cell Populations in the Phase 3 HERCULES Trial of Tolebrutinib in Non-Relapsing Secondary Progressive Multiple Sclerosis", Ectrims, P297, Presented at the 41st Congress of the European Committee for Treatment and Research in Multiple Sclerosis; Sep. 24-26, 2025; Barcelona, Spain (1 page).
Bar-Or, et al., "Blood Immunoglobulin Levels and Immune Cell Populations in the Phase 3 HERCULES Trial of Tolebrutinib in Non-Relapsing Secondary Progressive Multiple Sclerosis", P297, Multiple Sclerosis Journal, 31: (3S), 136-762, pp. 352-353 (2025).
Baston, E., "Extended European Search Report", issued in European Application No. EP 21902377.7 on Oct. 28, 2024 (6 pages).
Doherty, F., "International Preliminary Report on Patentability", issued in International Application No. PCT/US2022/053479 on Jun. 20, 2024 (9 pages).
Doherty, F., "International Preliminary Report on Patentability", issued in International Application No. PCT/US2023/084784 on Jun. 24, 2025 (13 pages).
Fox et al., "Subgroup Analyses of the Phase 3 Tolebrutinib in nrSPMS HERCULES Trial", Ectrims, P796, Presented at the 41st Congress of the European Committee for Treatment and Research in Multiple Sclerosis; Sep. 24-26, 2025; Barcelona, Spain (1 page).
Fox et al., "Subgroup Analyses of the Phase 3 Tolebrutinib in nrSPMS HERCULES Trial", Multiple Sclerosis Journal; 31: (3S) 136-762, pp. 671-672 (2025).
Gavriliu, D., "Extended European Search Report", issued in European Application No. 22188609.6 on Nov. 9, 2022 (7 pages).
Gavriliu, D., "Extended European Search Report", issued in European Patent Application No. 21169631.5 on Aug. 15, 2021 (13 pages).
Giovannoni, G., "Tolebrutinib PPMS trial is negative. The PERSEUS phase 3 study of tolebrutinib in primary progressive multiple sclerosis (PPMS) did not meet its primary endpoint.", MS-Selfie Research, Dec. 15, 2025 (6 pages).
Gulf News, "Emirates Drug Establishment grants global first approval for 'Tolebrutinib' for secondary progressive multiple sclerosis (SPMS)", Aug. 26, 2025 (11 pages).
Kleidernigg, Oliver, "Extended European Search Report", issued in European Application No. 22819443.7, mailed on May 23, 2025 (7 pages).
Kobayashi, M., "International Preliminary Report on Patentability", issued in International Application No. PCT/US2024/013658 on Jul. 31, 2025 (16 pages).
Kramer et al., "Bruton tyrosine kinase inhibitors in multiple sclerosis: evidence and expectations", Current Opinion in Neurology 37(3): pp. 237-244, Jun. 2024.
Lee, Sun Hwa, "International Preliminary Report on Patentability, issued in International Application No. PCT/US2021/064800" on Jun. 13, 2023 (9 pages).
Nakamura, Y., "International Preliminary Report on Patentability", International Application No. PCT/US2023/034655 on Apr. 15, 2025 (9 pages).
Nickitas-Etienne, A., "International Preliminary Report on Patentability", issued in International Application No. PCT/US2016/ 035588 on Dec. 5, 2017 (6 pages).
Nickitas-Etienne, A., "International Preliminary Report on Patentability", issued in International Application No. PCT/US2021/ 013883 on Jul. 26, 2022 (8 pages).
Nicolas et al., "Tolebrutinib Plasma Exposure and Efficacy Response in the Phase 3 HERCULES Trial in nrSPMS", Ectrims, P292, Presented at the 41st Congress of the European Committee for Treatment and Research in Multiple Sclerosis; Sep. 24-26, 2025; Barcelona, Spain (1 page).
Nicolas et al., "Tolebrutinib Plasma Exposure and Efficacy Response in the Phase 3 HERCULES Trial in nrSPMS", P292, Multiple Sclerosis Journal; 31: (3S) 136-762, pp. 347-348 (2025).
Oh et al., "Effects of Tolebrutinib on Progression Independent of Relapse Activity in the Phase 3 GEMINI Relapsing MS Trials", Multiple Sclerosis Journal 2025; 31: (3S) 136-762, p. 670 (2025).
Oh et al., "Effects of Tolebrutinib on Progression Independent of Relapse Activity in the Phase 3 GEMINI Relapsing MS Trials", Ectrims, P794, Presented at the 41st Congress of the European Committee for Treatment and Research in Multiple Sclerosis; Sep. 24-26, 2025; Barcelona, Spain (1 page).
Oh et al., "Tolebrutinib Phase 2b Long-Term Extension Study Two-Year Safety, MRI, and Clinical Efficacy Outcomes in Patients With Relapsing Multiple Sclerosis", Neurology Open Access, 1(3), 1: e000028 (Sep. 2025) (13 pages).
Rochaix, T., "International Preliminary Report on Patentability", issued in International Application No. PCT/ US2023/026526 on Dec. 18, 2024 (9 pages).
Sanofi Press Release, "Sanofi provides update on tolebrutinib in primary progressive multiple sclerosis", Dec. 15, 2025 (3 pages).
Schulte-Mecklenbeck et al., "Tolebrutinib treatment induces complex alterations of the peripheral immune-regulatory network in the blood of patients with non-relapsing secondary progressive MS—results from the TOLEDYNAMIC study", P315, Multiple Sclerosis Journal; 31: (3S) 136-762, pp. 364-365 (2025).
Schulte-Mecklenbeck et al., "Tolebrutinib treatment induces complex alterations of the peripheral immune-regulatory network in the blood of patients with non-relapsing secondary progressive MS—first results from the TOLEDYNAMIC study", Ectrims, P315, Poster Presentation Sep. 24, 2025 (1 page).
Vermersch et al., "Effects of Tolebrutinib on MSQOL-54 in the HERCULES Phase 3 Trial in nrSPMS", ECTRIMS, P810, Presented at the 41st Congress of the European Committee for Treatment and Research in Multiple Sclerosis; Sep. 24-26, 2025; Barcelona, Spain (1 page).
Vermersch et al., "Effects of Tolebrutinib on MSQOL-54 in the HERCULES Phase 3 trial in nrSPMS", Multiple Sclerosis Journal; 31: (3S) 136-762, pp. 684-685 (2025).
Wang, X., "International Preliminary Report on Patentability", issued in International Application No. PCT/ US2023/025808 on Dec. 18, 2024 (14 pages).
Wiendl et al., "Blood Immunoglobulin Levels and Immune Cell Populations in the Phase 3 GEMINI Trials of Tolebrutinib in

(56) References Cited

OTHER PUBLICATIONS

Relapsing Multiple Sclerosis", P800, Multiple Sclerosis Journal 2025; 31: (3S) 136-762 (2 pages).
Wiendl et al., "Blood Immunoglobulin Levels and Immune Cell Populations in the Phase 3 GEMINI Trials of Tolebrutinib in Relapsing Multiple Sclerosis", ECTRIMS, P800, Presented at the 41st Congress of the European Committee for Treatment and Research in Multiple Sclerosis; Sep. 24-26, 2025; Barcelona, Spain (1 page).
Pacreu Largo, Marta, "Notification of Transmittal of the International Search Report and the Written Opinion of the International Searching Authority, or the Declaration", issued in International Application No. PCT/US2025/043964, mailed on Feb. 6, 2026 (19 pages).

* cited by examiner

4-AMINO-3-(4-PHENOXYPHENYL)-1,3-DIHYDRO-2H-IMIDAZO[4,5-C]PYRIDIN-2-ONE DERIVATIVES AND SALTS THEREOF

CROSS-REFERENCE TO RELATED APPLICATIONS

This application is a national phase entry pursuant to 35 U.S.C. § 371 of International Application No. PCT/US2021/064800, filed Dec. 22, 2021, which claims the benefit of priority of U.S. Provisional Application No. 63/130,010, filed Dec. 23, 2020, and U.S. Provisional Application No. 63/245,288, filed Sep. 17, 2021, the entire contents of each of which are incorporated by reference herein in their entirety.

This application claims priority of U.S. Provisional Application No. 63/130,010, filed Dec. 23, 2020, and U.S. Provisional Application No. 63/245,288, filed Sep. 17, 2021.

FIELD

The present disclosure relates to 4-amino-3-(4-phenoxyphenyl)-1,3-dihydro-2H-imidazo[4,5-c]pyridin-2-one variants or derivatives, and salts thereof, for use as agonists and antagonists. The disclosure further relates to pharmaceutical compositions, methods of preparing, and methods of treatment.

BACKGROUND

Small molecule drugs have found utility in a wide range of diseases and conditions. Some act as antagonists by blocking or dampening a biological response. Some act as agonists by activating a biological response. Others can function as both.

While many small molecule drugs are known, there is a need for new and different therapeutic agents. For example, according to National Center for Complementary and Integrative Health, about 2.5 million people world-wide, including some 400,000 people in the United States, suffer from multiple sclerosis ("MS"). While there are some drugs that are available for the treatment of MS, not everyone responds well to the available medications. Other examples of diseases or conditions where a need exists include autoimmune disorders such as lupus, pemphigus vulgaris, myasthenia gravis, Sjogren's syndrome, dry eye, multiple sclerosis, Wegener's granulomatosis, autoimmune hemolytic anemia, idiopathic thrombocytopenic purpura, Granulomatosis with Polyangiitis, or rheumatoid arthritis.

The present disclosure provides compounds that are tyrosine kinase inhibitors, in particular Bruton tyrosine kinase ("BTK") inhibitors, and are therefore useful for the treatment of diseases such as cancer, autoimmune, inflammatory, and thromboembolic diseases. Also provided are pharmaceutical compositions containing such compounds and processes for preparing such compounds.

BTK, a member of the Tec family non-receptor tyrosine kinases, is essential for B cell signaling downstream from the B-cell receptor. It is expressed in B cells and other hematopoietic cells such as monocytes, macrophages and mast cells. It functions in various aspects of B cell function that maintain the B cell repertoire (see Gauld S. B. et al., B cell antigen receptor signaling: roles in cell development and disease. Science, 296:1641-2. 2002). B cells play a role in rheumatoid arthritis (see Perosa F., et al., CD20-depleting therapy in autoimmune diseases: from basic research to the clinic. *J Intern Med.* 267:260-77. 2010 and Dörner T, et al. Targeting B cells in immune-mediated inflammatory disease: a comprehensive review of mechanisms of action and identification of biomarkers. *Pharmacol Ther.* 125:464-75. 2010 and Honigberg, L., et. al., The selective BTK inhibitor PCI-32765 blocks B cell and mast cell activation and prevents mouse collagen-induced arthritis. *Clin. Immunol* 127 S1:S111. 2008) and in other autoimmune diseases such as systemic lupus erythematosus and cancers (see Shlomchik M. J., et. al., The role of B cells in lpr/lpr-induced autoimmunity. *J. Exp Med.* 180:1295-1306. 1994; Honigberg L. A., The Bruton tyrosine kinase inhibitor PCI-32765 blocks B-cell activation and is efficacious in models of autoimmune disease and B-cell malignancy. *Proc. Natl. Acad. Sci.* 107:13075-80. 2010; and Mina-Osorio P, et al., Suppression of glomerulonephritis in lupus-prone NZB× NZW mice by RN486, a selective inhibitor of Bruton's tyrosine kinase. *Arthritis Rheum.* 65: 2380-91. 2013).

There is also potential for BTK inhibitors for treating allergic diseases (see Honigberg, L., et. al, The selective BTK inhibitor PCI-32765 blocks B cell and mast cell activation and prevents mouse collagen induced arthritis. *Clin. Immunol* 127 S1:S111. 2008). It was noted that the irreversible inhibitor suppresses passive cutaneous anaphylaxis (PCA) induced by IgE antigen complex in mice. These findings are in agreement with those noted with BTK-mutant mast cells and knockout mice and suggest that BTK inhibitors may be useful for the treatment of asthma, an IgE-dependent allergic disease of the airway.

Accordingly, compounds that inhibit BTK would be useful in treatment for diseases such as autoimmune diseases, inflammatory diseases, and cancer.

It has been surprisingly discovered that certain 4-amino-3-(4-phenoxyphenyl)-1,3-dihydro-2H-imidazo[4,5-c]pyridin-2-one derivatives act as agonists, antagonists, or both on a number of receptors that are implicated in many of the diseases and disorders, including those listed above.

SUMMARY

Described herein, in certain embodiments, are derivatives of 4-amino-3-(4-phenoxyphenyl)-1,3-dihydro-2H-imidazo[4,5-c]pyridin-2-one and salts thereof.

In one embodiment, disclosed herein is a compound of Formula I:

Formula I

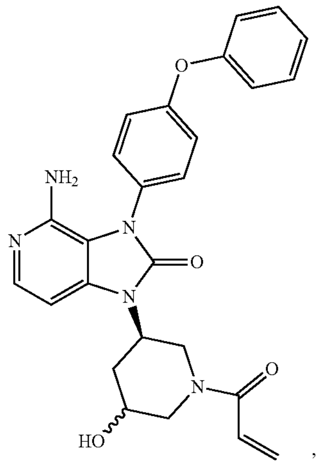

, or a salt thereof.

In one embodiment, disclosed herein is a compound of Formula Ia:

Formula Ia

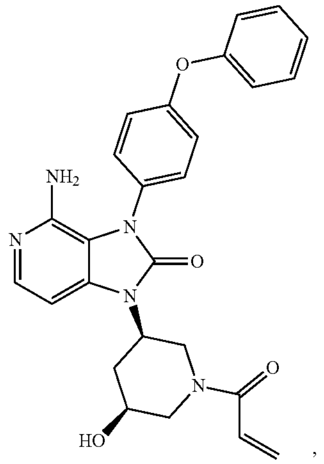

or a salt thereof. In another embodiment, the compound of Formula Ia or salt thereof is about 90% pure.

In another embodiment, disclosed herein is a compound of Formula Ib:

Formula Ib

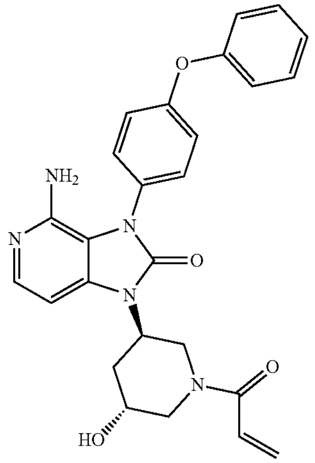

or a salt thereof, wherein the compound or salt thereof is about 90% pure.

In a further embodiment, disclosed herein is a compound of Formula II

Formula II

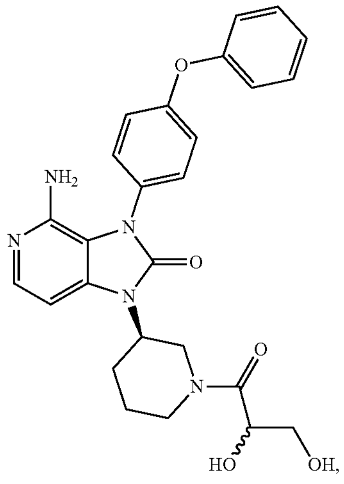

or salt thereof, wherein the compound or salt thereof is about 99.6% pure.

In another embodiment, disclosed herein is a composition comprising a pharmaceutically acceptable excipient and at least one compound chosen from:

Formula Ia

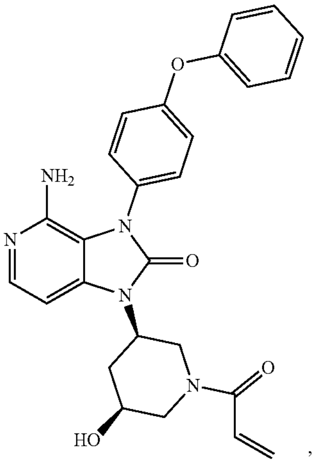

Formula Ib

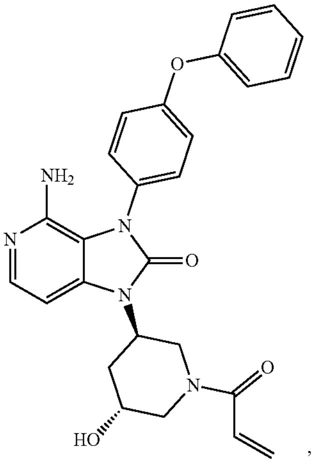

-continued

Formula II

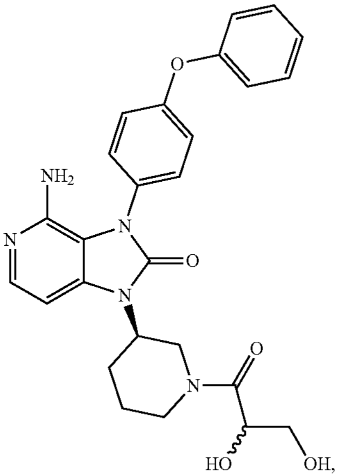

HO OH, and

Formula III

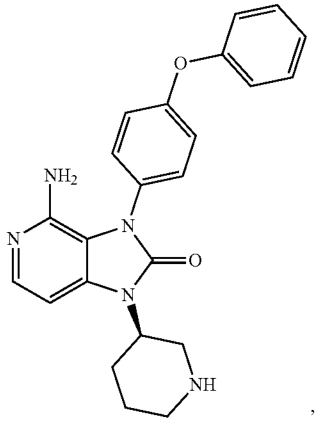

, or a salt thereof.

In a further embodiment, disclosed herein is a method of preparing a compound of Formula Ia or salt thereof, the method comprising reacting a compound of Formula VIa Formula VIa

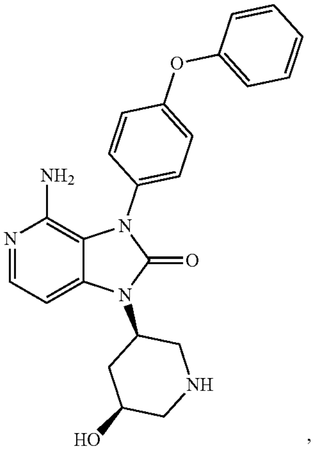

, with acryloyl chloride.

In a further embodiment, disclosed herein is a method of preparing a compound of Formula Ib or salt thereof, the method comprising reacting a compound of Formula VIb Formula VIb

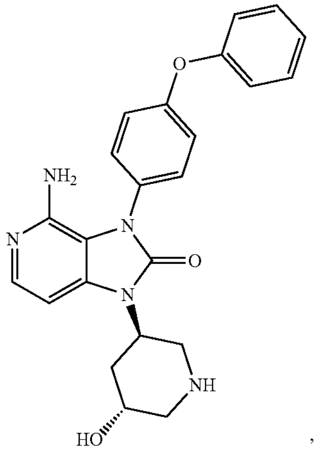

, with acryloyl chloride.

Additional objects and advantages will be set forth in part in the description which follows, and in part will be understood from the description, or may be learned by practice. The objects and advantages will be realized and attained by means of the elements and combinations particularly pointed out in the appended claims.

It is to be understood that both the foregoing summary and the following detailed description are exemplary and explanatory only and are not restrictive of the claims.

DESCRIPTION OF THE EMBODIMENTS

I. Definitions

Unless otherwise stated, the following terms used in the specification and claims are defined for the purposes of this disclosure and have the following meaning:

A "pharmaceutically acceptable carrier" or "pharmaceutically acceptable excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier" or "a pharmaceutically acceptable excipient" as used in the specification and claims includes both one and more than one such carrier or excipient.

"Treating" or "treatment" of a disease includes:

(1) preventing the disease, e.g., causing the clinical symptoms of the disease not to develop in a patient, e.g., a human patient, that may have been exposed to or predisposed to the disease but does not yet experience or display symptoms of the disease;

(2) inhibiting the disease, e.g., arresting or reducing the development of the disease or its clinical symptoms; or (3) relieving the disease, e.g., causing regression of the disease or its clinical symptoms.

"Optional" or "optionally" means that the subsequently described event or circumstance may but need not occur, and that the description includes instances where the event or circumstance occurs and instances in which it does not.

A "therapeutically effective amount" means the amount of the 4-amino-3-(4-phenoxyphenyl)-1,3-dihydro-2H-imidazo[4,5-c]pyridin-2-one derivative or salt thereof, that, when administered to a patient, e.g., a human patient for treating a disease, is sufficient to affect such treatment for the disease. The "therapeutically effective amount" will vary depending on the compound, the disease and its severity and the age, weight, etc., of the patient, e.g., a human patient to be treated.

"about X % pure" or "about X % purity" (where "X" is a number) means that the referenced compound is present in about X % as determined by area via HPLC (detected by UV @254 nm) of the total peak area.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a conjugate" includes a plurality of conjugates and reference to "a cell" includes a plurality of cells and the like.

Numeric ranges are inclusive of the numbers defining the range. Measured and measurable values are understood to be approximate, taking into account significant digits and the error associated with the measurement. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

"Or" is used in the inclusive sense, i.e., equivalent to "and/or," unless the context requires otherwise.

II. Compounds

In one aspect, provided herein are compounds that are 4-amino-3-(4-phenoxyphenyl)-1,3-dihydro-2H-imidazo[4,5-c]pyridin-2-one derivatives and salts thereof. In some embodiments, the compounds are about 50% pure. In some embodiments, the compounds are about 55% pure. In some embodiments, the compounds are about 60% pure. In some embodiments, the compounds are about 65% pure. In some embodiments, the compounds are about 70% pure. In some embodiments, the compounds are about 75% pure. In some embodiments, the compounds are about 80% pure. In some embodiments, the compounds are about 85% pure. In some embodiments, the compounds are about 90% pure. In some embodiments, the compounds are about 95% pure. In some embodiments, the compounds are about 98% pure. In some embodiments, the compounds are about 99% pure.

In one aspect, provided herein is a compound of Formula I:

Formula I

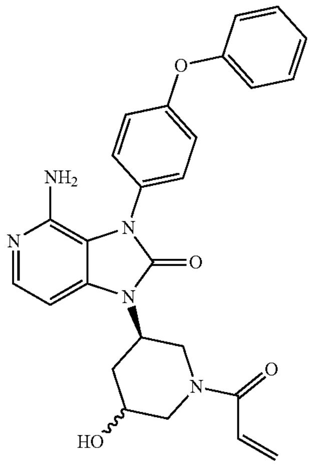

or a salt thereof.

In one aspect, provided herein is a compound of Formula Ia:

Formula Ia

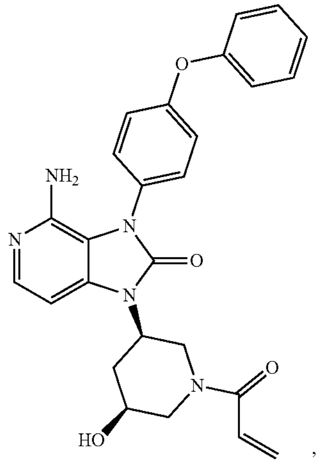

or a salt thereof. In some embodiments, the compound of Formula Ia or salt thereof is about 90% pure. In some embodiments, the compound of Formula Ia or salt thereof is about 95% pure. In some embodiments, the compound of Formula Ia or salt thereof is about 98% pure. In some embodiments, the compound of Formula Ia or salt thereof is about 99% pure.

In one aspect, provided herein is a compound of Formula Ib:

Formula Ib

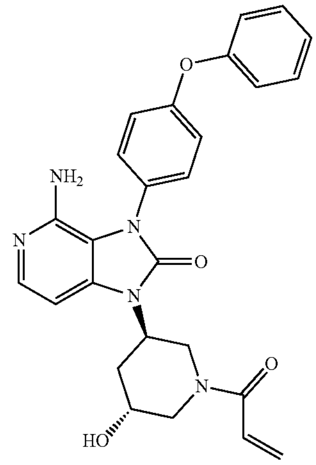

or a salt thereof, wherein the compound or salt thereof is about 90% pure. In some embodiments, the compound of Formula Ib or salt thereof is about 95% pure. In some embodiments, the compound of Formula Ib or salt thereof is about 98% pure. In some embodiments, the compound of Formula Ib or salt thereof is about 99% pure.

In one aspect, provided herein is a compound of Formula II

Formula II

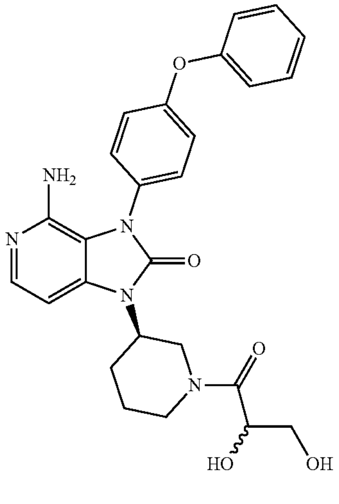

or salt thereof, wherein the compound or salt thereof is about 99.6% pure. In some embodiments, the compound is Formula IIa

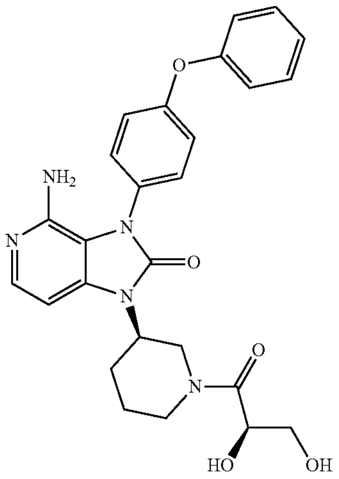

or salt thereof, wherein the compound or salt thereof is about 90% pure. In some embodiments, the compound of Formula IIa or salt thereof is about 95% pure. In some embodiments, the compound of Formula IIa or salt thereof is about 98% pure. In some instances, the compound is Formula IIb

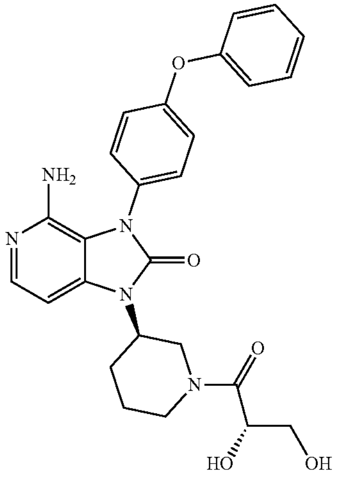

or salt thereof, wherein the compound or salt thereof is about 90% pure. In some embodiments, the compound of Formula IIb or salt thereof is about 95% pure.

In some embodiments, the compound of Formula IIb or salt thereof is about 98% pure.

In one aspect, the disclosure relates to a compound chosen from those of Formula III, Formula IV, and Formula V Formula III

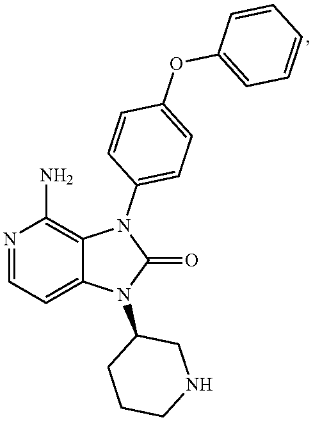

Formula IV

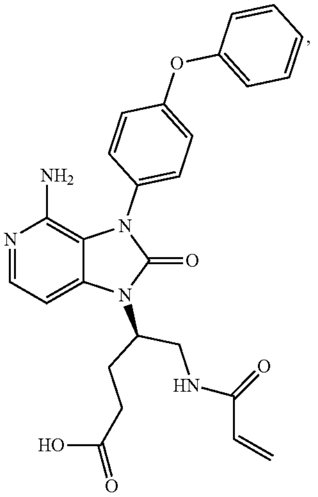

Formula V

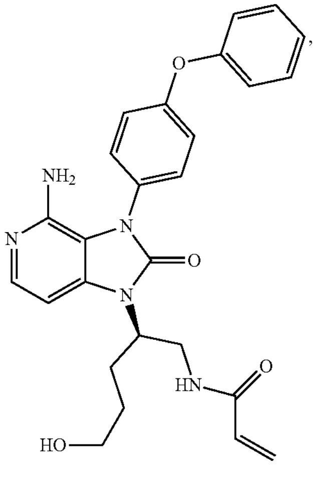

or salts thereof.

III. Compositions

In one aspect, provided herein are pharmaceutical compositions comprising a pharmaceutically acceptable excipient, and compounds which are variants or derivatives of 4-amino-3-(4-phenoxyphenyl)-1,3-dihydro-2H-imidazo[4,5-c]pyridin-2-one or salts thereof. These compounds were discovered by the present inventors as in vivo metabolites of (R)-1-(1-acryloylpiperidin-3-yl)-4-amino-3-(4-phenoxyphenyl)-1H-imidazo[4,5-c]pyridin-2(3H)-one.

In one embodiment, provided herein is a composition comprising a pharmaceutically acceptable excipient and at least one compound chosen from:

Formula Ia

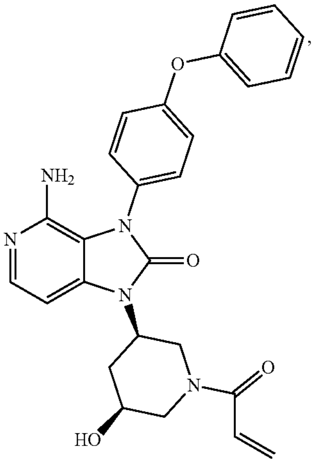

Formula Ib

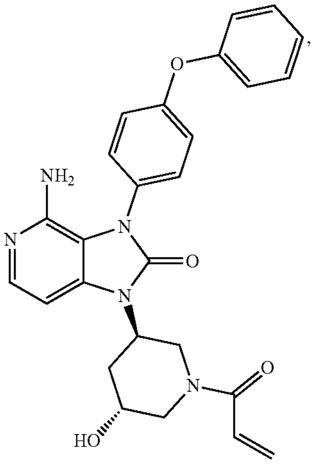

Formula II

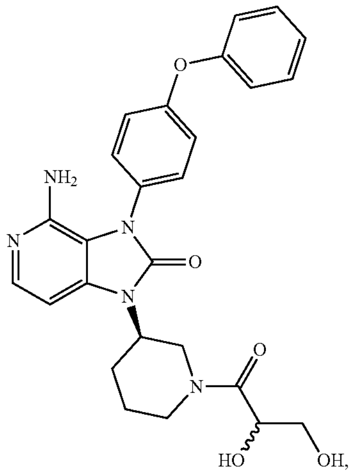

-continued
Formula III
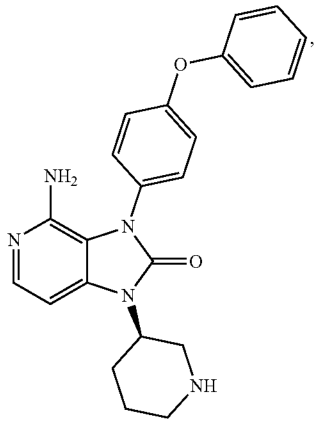
Formula IV
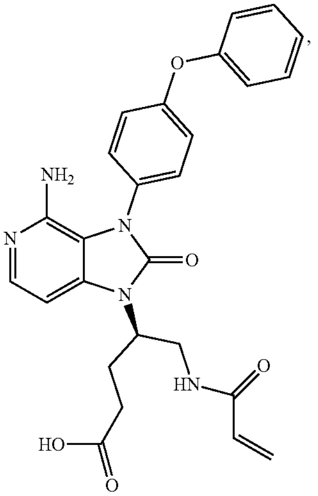
and
Formula V
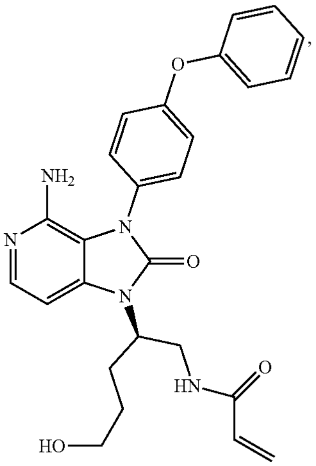
or a salt thereof. In some embodiments, at least one compound or salt thereof is present in an effective amount.
In one embodiment, provided herein is a composition comprising a pharmaceutically acceptable excipient and at least one compound chosen from:
Formula Ia
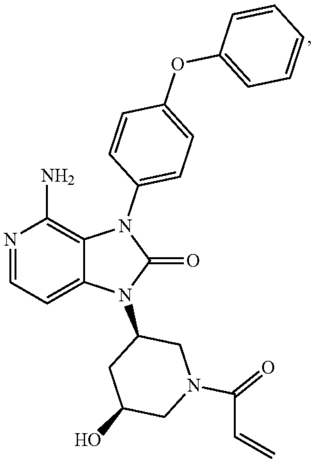
Formula Ib
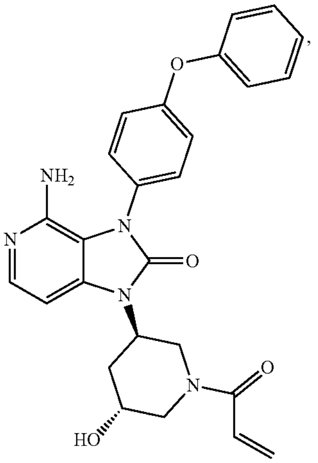
Formula II
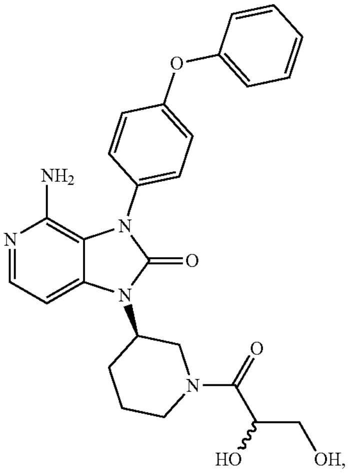
and -continued Formula III

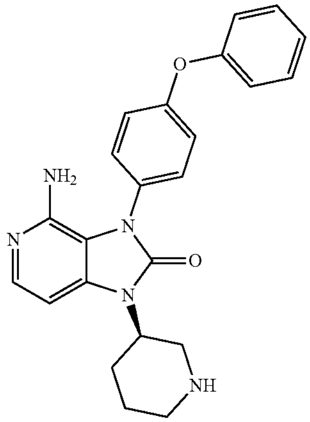

or a salt thereof.

In some embodiments, at least one compound or salt thereof is present in an effective amount. In one embodiment, provided herein is a composition comprising a pharmaceutically acceptable excipient and a compound of Formula Ia or a salt thereof. In some embodiments, the compound of Formula Ia or salt thereof is at least about 98% pure.

In one embodiment, provided herein is a composition comprising a pharmaceutically acceptable excipient and a compound of Formula Ib or a salt thereof. In some embodiments, the compound of Formula Ib or salt thereof is at least about 99% pure.

Pharmaceutical compositions according to the disclosure may take a form suitable for oral, buccal, parenteral, nasal, topical, or rectal administration, or a form suitable for administration by inhalation.

The compounds described herein can be used in the preparation of a composition, such as a pharmaceutical composition, by combining the compound as an active ingredient with a pharmaceutically acceptable excipient. Some examples of materials which can serve as pharmaceutically acceptable excipients include: sugars, such as lactose, glucose and sucrose; starches, such as corn starch and potato starch; cellulose and its derivatives, such as sodium carboxymethyl cellulose, ethyl cellulose and cellulose acetate; surfactants, such as polysorbate 80 (i.e., Tween 80); powdered tragacanth; malt; gelatin; talc; suppository bases, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates or polyanhydrides; and other non-toxic compatible substances employed in pharmaceutical compositions. Pharmaceutical compositions may be prepared by known pharmaceutical methods. Suitable formulations can be found in, for example, *Remington: The Science and Practice of Pharmacy*, Lippincott Williams & Wilkins, 21st ed. (2005), which is incorporated herein by reference.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol and the like; and metal chelating agents, such as citric acid, ethylenediamine tetraacetic acid (EDTA), sorbitol, tartaric acid, phosphoric acid and the like.

Compositions of the disclosure suitable for oral administration may be in the form of capsules, cachets, pills, tablets, lozenges (using a flavored basis, usually sucrose and acacia or tragacanth), powders, granules or as a solution or a suspension in an aqueous or non-aqueous liquid or as an oil-in-water or water-in-oil liquid emulsion or as an elixir or syrup or as pastilles (using an inert base, such as gelatin and glycerin or sucrose and acacia) or as mouth washes and the like, each containing a predetermined amount of a compound of the present disclosure as an active ingredient. A compound of the present disclosure may also be administered as a bolus, electuary or paste.

In solid dosage forms of the disclosure for oral administration (capsules, tablets, pills, dragées, powders, granules and the like), the active ingredient is mixed with one or more pharmaceutically-acceptable carriers, such as sodium citrate or dicalcium phosphate or any of the following: fillers or extenders, such as starches, lactose, sucrose, glucose, mannitol or silicic acid; binders, such as, for example, carboxymethylcellulose, alginates, gelatin, polyvinyl pyrrolidone, sucrose or acacia; humectants, such as glycerol; disintegrating agents, such as agar-agar, calcium carbonate, potato or tapioca starch, alginic acid, certain silicates and sodium carbonate; solution retarding agents, such as paraffin; absorption accelerators, such as quaternary ammonium compounds; wetting agents, such as, for example, cetyl alcohol, glycerol monostearate and non-ionic surfactants; absorbents, such as kaolin and bentonite clay; lubricants, such a talc, calcium stearate, magnesium stearate, solid polyethylene glycols, sodium lauryl sulfate and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using a binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets and other solid dosage forms of the pharmaceutical compositions of the present disclosure, such as dragées, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes or microspheres. They may be formulated for rapid release, e.g., freeze-dried. They may be sterilized by, for example, filtration through a bacteria-retaining filter or by incorporating sterilizing agents in the form of sterile solid compositions that can be dissolved in sterile water or some other sterile injectable medium immediately before use. These compositions may also optionally contain opacifying agents and may be of a composition that they release the active ingredient(s) only or in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth and mixtures thereof.

IV. Methods of Treatment

In one aspect, provided herein are methods of treatment comprising administering to a patient, e.g., a human patient, in need thereof an effective amount of a derivative of 4-amino-3-(4-phenoxyphenyl)-1,3-dihydro-2H-imidazo[4,5-c]pyridin-2-one or salt thereof. In another aspect, provided herein are methods of treatment comprising administering to a patient, e.g., a human patient, in need thereof a composition comprising a pharmaceutically acceptable excipient and an effective amount of a derivative of 4-amino-3-(4-phenoxyphenyl)-1,3-dihydro-2H-imidazo[4,5-c]pyridin-2-one or salt thereof.

In some embodiments, the method is a method of treating MS. In some embodiments, the method is a method of treating autoimmune disorders such as rheumatoid arthritis and lupus.

In one aspect, provided herein is a method of treatment comprising administering to a patient, e.g., a human patient, in need thereof an effective amount of a compound of Formula Ia:

Formula Ia

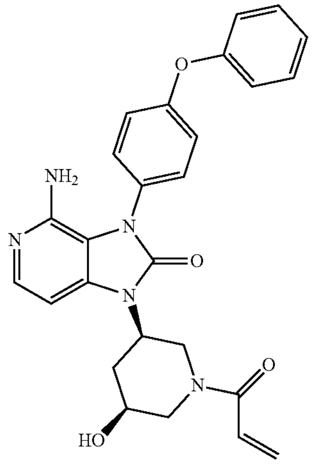

or a salt thereof. In some embodiments, the compound of Formula Ia or salt thereof is about 90% pure. In some embodiments, the compound of Formula Ia or salt thereof is about 95% pure. In some embodiments, the compound of Formula Ia or salt thereof is about 98% pure. In some embodiments, the compound of Formula Ia or salt thereof is about 99% pure.

In some embodiments, the method of treatment comprising administering to a patient, e.g., a human patient, in need thereof an effective amount of a compound of Formula Ia or salt thereof is a method of treating MS. In some embodiments, the method of treatment comprising administering to a patient, e.g., a human patient, in need thereof an effective amount of a compound of Formula Ia or salt thereof is a method of treating autoimmune disorders such as rheumatoid arthritis and lupus.

In one aspect, provided herein is a method of treatment comprising administering to a patient, e.g., a human patient, in need thereof an effective amount of a compound of Formula Ib:

Formula Ib

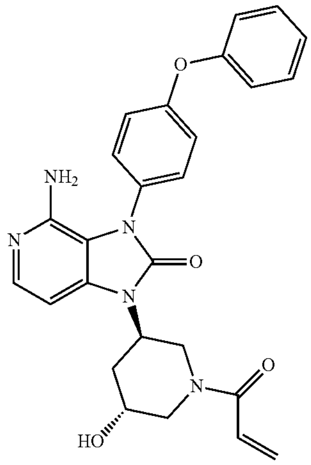

or a salt thereof, wherein the compound or salt thereof is about 90% pure. In some embodiments, the compound of Formula Ib or salt thereof is about 95% pure. In some embodiments, the compound of Formula Ib or salt thereof is about 98% pure. In some embodiments, the compound of Formula Ib or salt thereof is about 99% pure.

In some embodiments, the method of treatment comprising administering to a patient, e.g., a human patient, in need thereof an effective amount of a compound of Formula Ib or salt thereof is a method of treating MS. In some embodiments, the method of treatment comprising administering to a patient, e.g., a human patient, in need thereof an effective amount of a compound of Formula Ia or salt thereof is a of treating autoimmune disorders such as rheumatoid arthritis and lupus.

In one aspect, provided herein is a method of treatment comprising administering to a patient, e.g., a human patient, in need thereof an effective amount of a compound of Formula II:

Formula II

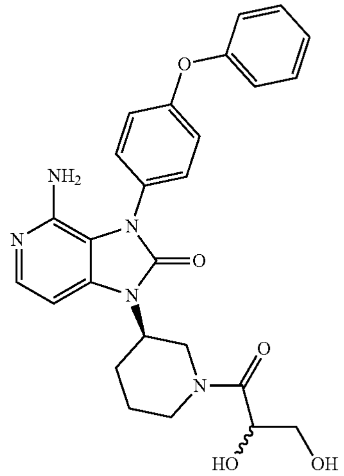

or salt thereof, wherein the compound or salt thereof is about 99.6% pure.

In some embodiments, the method of treatment comprising administering to a patient, e.g., a human patient, in need thereof an effective amount of a compound of Formula II or salt thereof is a method of treating MS. In some embodiments, the method of treatment comprising administering to a patient, e.g., a human patient, in need thereof an effective amount of a compound of Formula II or salt thereof is a of treating autoimmune disorders such as rheumatoid arthritis and lupus.

In some embodiments, the compound is

Formula IIa

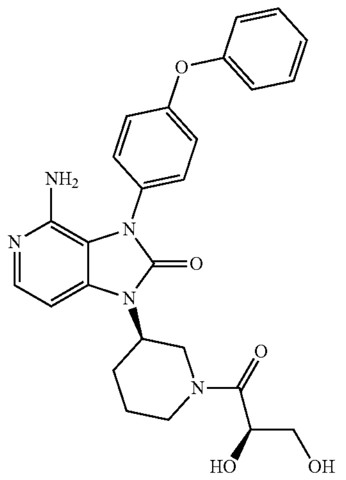

or salt thereof, wherein the compound of Formula IIa or salt thereof is about 90% pure. In some embodiments, the compound of Formula IIa or salt thereof is about 95% pure. In some embodiments, the compound of Formula IIa or salt thereof is about 98% pure.

In some embodiments, the method of treatment comprising administering to a patient, e.g., a human patient, in need thereof an effective amount of a compound of Formula IIa or salt thereof is a method of treating MS. In some embodiments, the method of treatment comprising administering to a patient, e.g., a human patient, in need thereof an effective amount of a compound of Formula IIa or salt thereof is a of treating autoimmune disorders such as rheumatoid arthritis and lupus.

In some instances, the compound is

Formula IIb

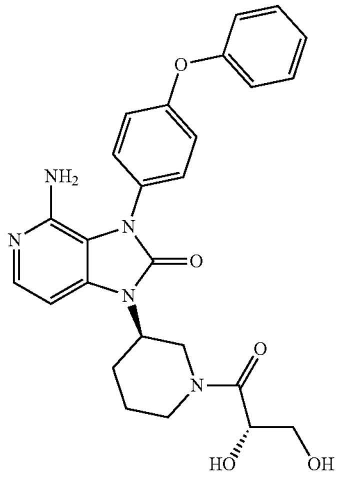

or salt thereof, wherein the compound of Formula IIb or salt thereof is about 90% pure. In some embodiments, the compound of Formula IIb or salt thereof is about 95% pure. In some embodiments, the compound of Formula IIb or salt thereof is about 98% pure.

In some embodiments, the method of treatment comprising administering to a patient, e.g., a human patient, in need thereof an effective amount of a compound of Formula IIb or salt thereof is a method of treating MS. In some embodiments, the method of treatment comprising administering to a patient, e.g., a human patient, in need thereof an effective amount of a compound of Formula IIb or salt thereof is a of treating an autoimmune disorder such as rheumatoid arthritis and lupus.

In one aspect, provided herein is a method of treatment comprising administering to a patient, e.g., a human patient, in need thereof a composition comprising a pharmaceutically acceptable excipient and an effective amount of at least one compound chosen from Formula Ia

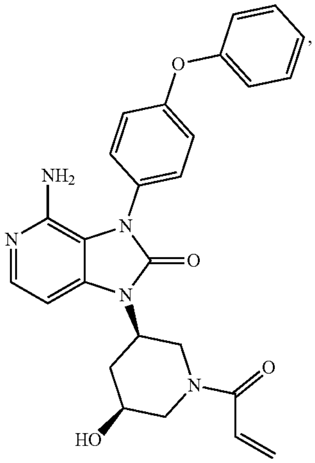

,

Formula Ib

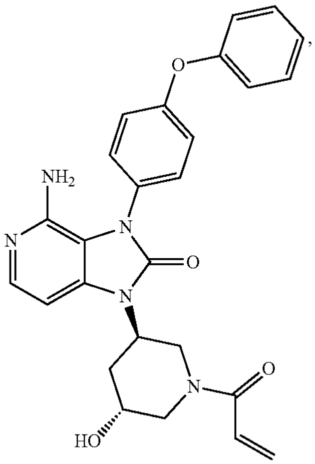

,

-continued

Formula II

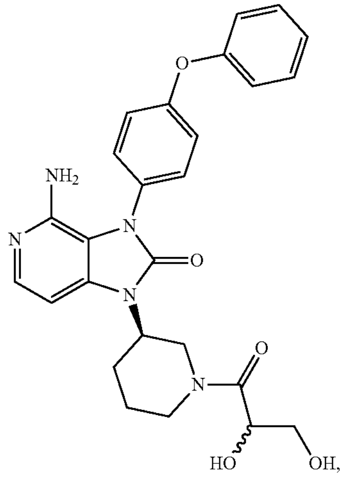

and

Formula III

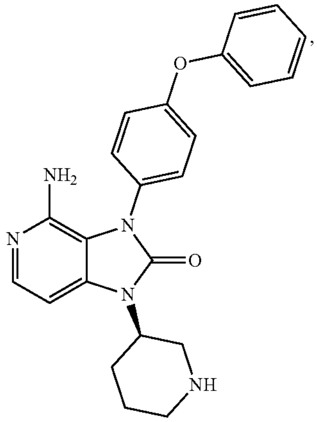

, or salt thereof. In some embodiments, at least one compound or salt thereof is present in an effective amount. In some embodiments, the compound or salt thereof is about 90% pure. In some embodiments, the compound or salt thereof is about 95% pure. In some embodiments, the compound or salt thereof is about 98% pure. In some embodiments, the compound or salt thereof is about 99% pure.

In some embodiments, the method of treatment comprising administering to a patient, e.g., a human patient, in need thereof a composition comprising a pharmaceutically acceptable excipient and an effective amount of at least one compound chosen from Formula Ia, Formula Ib, Formula II, and Formula III or salt thereof is a method of treating MS. In some embodiments, the method of treatment comprising administering to a patient, e.g., a human patient, in need thereof a composition comprising a pharmaceutically acceptable excipient and an effective amount of at least one compound chosen from Formula Ia, Formula Ib, Formula II, and Formula III, or salt thereof is a method of treating an autoimmune disorder such as rheumatoid arthritis and lupus.

In one aspect, provided herein are compositions for use as a medicament for treating a patient, e.g., a human patient, in need thereof comprising an effective amount of a derivative of 4-amino-3-(4-phenoxyphenyl)-1,3-dihydro-2H-imidazo[4,5-c]pyridin-2-one or salt thereof. In another aspect, provided herein are compositions for use as a medicament for treating a patient, e.g., a human patient, in need thereof comprising a pharmaceutically acceptable excipient and an effective amount of a derivative of 4-amino-3-(4-phenoxy-phenyl)-1,3-dihydro-2H-imidazo[4,5-c]pyridin-2-one or salt thereof.

In some embodiments, the medicament is for treating MS. In some embodiments, the medicament is for treating auto-immune disorders such as rheumatoid arthritis and lupus.

In one aspect, provided herein is a composition for use as a medicament for treating a patient, e.g., a human patient, in need thereof comprising an effective amount of a compound of Formula Ia:

Formula Ia

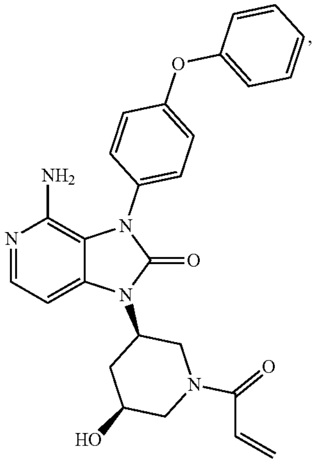

or a salt thereof. In some embodiments, the compound of Formula Ia or salt thereof is about 90% pure. In some embodiments, the compound of Formula Ia or salt thereof is about 95% pure. In some embodiments, the compound of Formula Ia or salt thereof is about 98% pure. In some embodiments, the compound of Formula Ia or salt thereof is about 99% pure.

In some embodiments, the composition for use as a medicament for treating a patient, e.g., a human patient, in need thereof comprises an effective amount of a compound of Formula Ia or salt thereof for treating MS. In some embodiments, the composition for use as a medicament for treating a patient, e.g., a human patient, in need thereof comprises an effective amount of a compound of Formula Ia or salt thereof for treating autoimmune disorders such as rheumatoid arthritis and lupus.

In one aspect, provided herein is a composition for use as a medicament for treating a patient, e.g., a human patient, in need thereof comprising an effective amount of a compound of Formula Ib:

Formula Ib

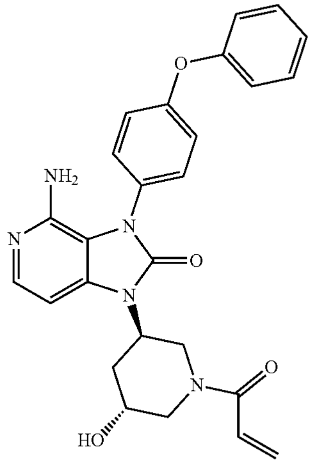

or a salt thereof, wherein the compound or salt thereof is about 90% pure. In some embodiments, the compound of Formula Ib or salt thereof is about 95% pure. In some embodiments, the compound of Formula Ib or salt thereof is about 98% pure. In some embodiments, the compound of Formula Ib or salt thereof is about 99% pure.

In some embodiments, the composition for use as a medicament for treating a patient, e.g., a human patient, in need thereof comprises an effective amount of a compound of Formula Ia or salt thereof for treating MS. In some embodiments, the composition for use as a medicament for treating a patient, e.g., a human patient, in need thereof comprises an effective amount of a compound of Formula Ia or salt thereof for treating autoimmune disorders such as rheumatoid arthritis and lupus.

In one aspect, provided herein is a composition for use as a medicament for treating a patient, e.g., a human patient, in need thereof comprising an effective amount of a compound of Formula II:

Formula II

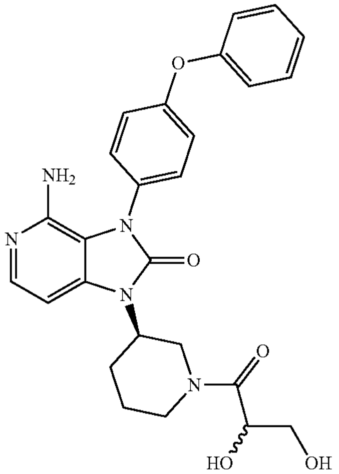

or salt thereof, wherein the compound or salt thereof is about 99.6% pure.

In some embodiments, the composition for use as a medicament for treating a patient, e.g., a human patient, in need thereof comprises an effective amount of a compound of Formula II or salt thereof for treating MS. In some embodiments, the composition for use as a medicament for treating a patient, e.g., a human patient, in need thereof comprises an effective amount of a compound of Formula II or salt thereof for treating autoimmune disorders such as rheumatoid arthritis and lupus.

In some embodiments, the compound is

Formula IIa

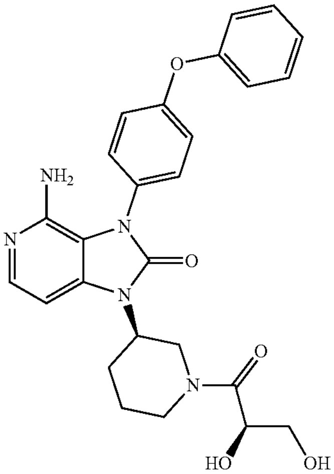

or salt thereof, wherein the compound of Formula IIa or salt thereof is about 90% pure. In some embodiments, the compound of Formula IIa or salt thereof is about 95% pure. In some embodiments, the compound of Formula IIa or salt thereof is about 98% pure.

In some embodiments, the composition for use as a medicament for treating a patient, e.g., a human patient, in need thereof comprises an effective amount of a compound of Formula IIa or salt thereof for treating MS. In some embodiments, the composition for use as a medicament for treating a patient, e.g., a human patient, in need thereof comprises an effective amount of a compound of Formula IIa or salt thereof for treating autoimmune disorders such as rheumatoid arthritis and lupus.

In some instances, the compound is

Formula IIb

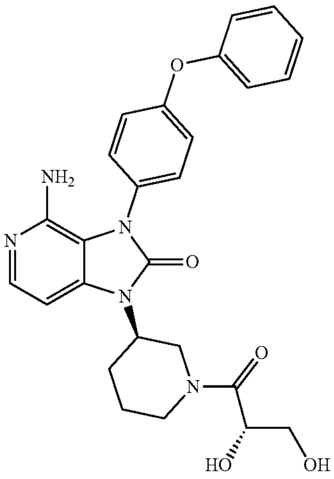

or salt thereof, wherein the compound of Formula IIb or salt thereof is about 90% pure. In some embodiments, the compound of Formula IIb or salt thereof is about 95% pure. In some embodiments, the compound of Formula IIb or salt thereof is about 98% pure.

In some embodiments, the composition for use as a medicament for treating a patient, e.g., a human patient, in need thereof comprises an effective amount of a compound of Formula IIb or salt thereof for treating MS. In some embodiments, the composition for use as a medicament for treating a patient, e.g., a human patient, in need thereof comprises an effective amount of a compound of Formula IIb or salt thereof for treating autoimmune disorders such as rheumatoid arthritis and lupus.

In one aspect, provided herein is a composition for use as a medicament for treating a patient, e.g., a human patient, in need thereof comprising a pharmaceutically acceptable excipient and an effective amount of at least one compound chosen from Formula Ia

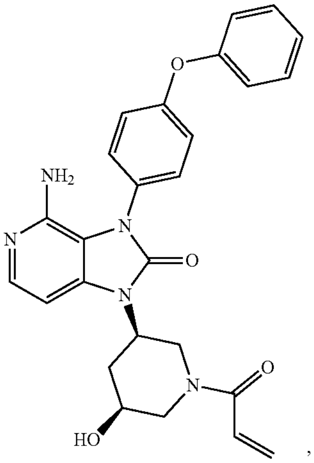

,

Formula Ib

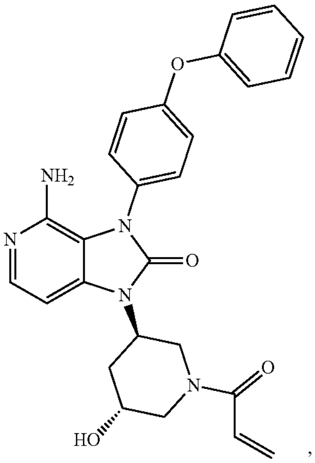

,

-continued

Formula II

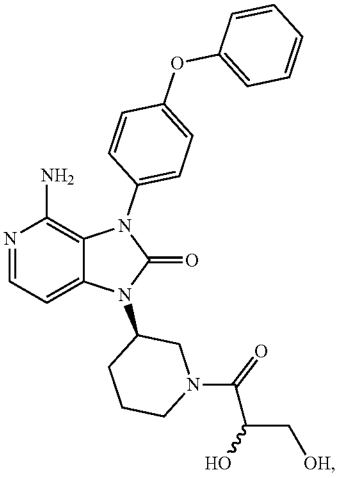

and

Formula III

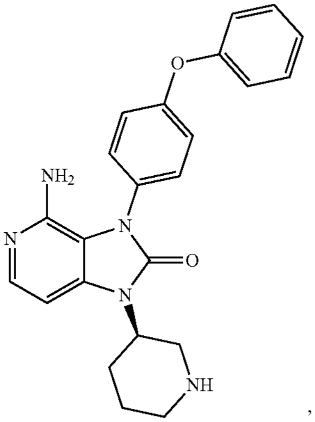

, or salt thereof. In some embodiments, at least one compound or salt thereof is present in an effective amount. In some embodiments, the compound or salt thereof is about 90% pure. In some embodiments, the compound or salt thereof is about 95% pure. In some embodiments, the compound or salt thereof is about 98% pure. In some embodiments, the compound or salt thereof is about 99% pure.

In some embodiments, the composition for use as a medicament for treating a patient, e.g., a human patient, in need thereof comprises a pharmaceutically acceptable excipient and an effective amount of at least one compound chosen from Formula Ia, Formula Ib, Formula II, and Formula III or salt thereof is for treating MS. In some embodiments, the composition for use as a medicament for treating a patient, e.g., a human patient, in need thereof comprises a pharmaceutically acceptable excipient and an effective amount of at least one compound chosen from Formula Ia, Formula Ib, Formula II, and Formula III, and/or salt thereof is for treating an autoimmune disorder such as rheumatoid arthritis and lupus.

V. Methods of Synthesis

In one aspect, provided herein are methods of synthesizing and preparing derivatives of 4-amino-3-(4-phenoxyphenyl)-1,3-dihydro-2H-imidazo[4,5-c]pyridin-2-one or salt thereof.

In one embodiment, provided herein is a method of preparing a compound of Formula Ia or salt thereof Formula Ia

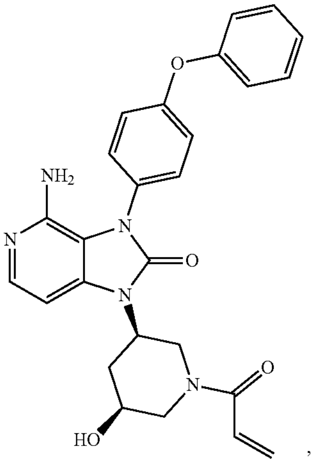

, the method comprising reacting a compound of Formula VIa

Formula VIa

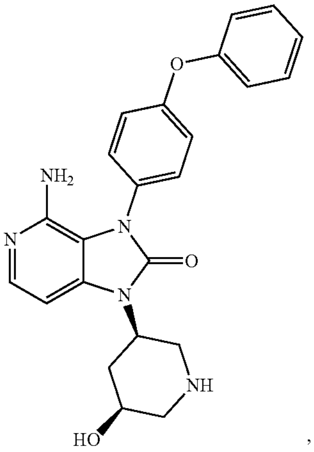

, with acryloyl chloride.

In some embodiments, the method further comprises preparing a compound of Formula VIa from a compound of Formula IX Formula IX

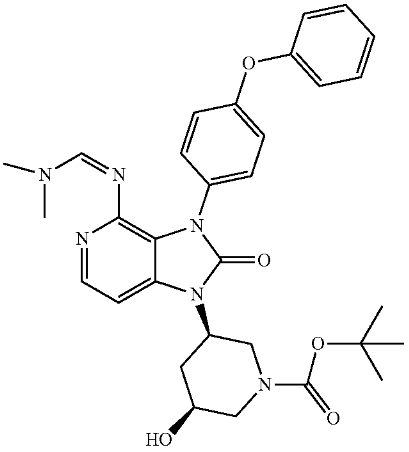

by acid-based deprotection.

In one embodiment, provided herein is a method of preparing a compound of Formula Ib or salt thereof Formula Ib

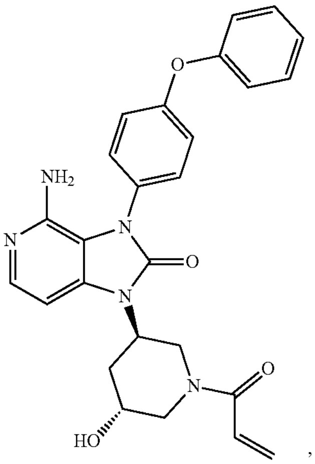

, the method comprising reacting a compound of Formula VIb

Formula VIb

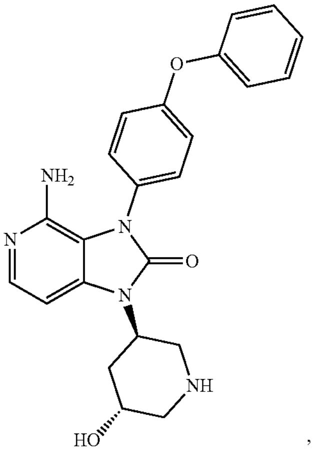

, with acryloyl chloride.

In some embodiments, the method further comprises preparing a compound of Formula VIb from a compound of Formula VII Formula VII

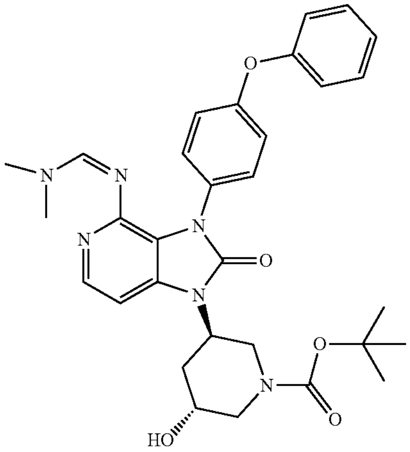

by acid-based deprotection.

In some embodiments, the method further comprises preparing a compound of Formula VII from a compound of Formula VIII Formula VIII

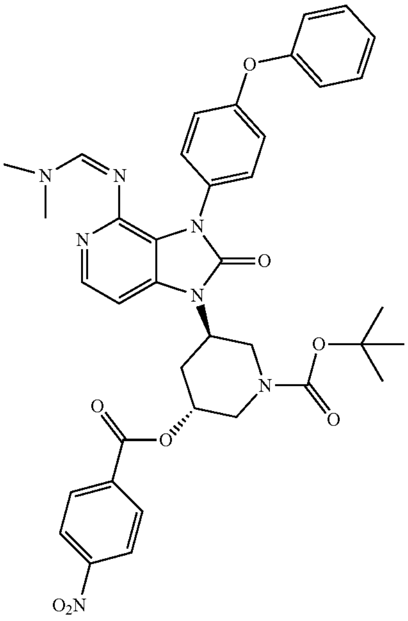

by deprotection using a base.

In some embodiments, the method further comprises preparing a compound of Formula VIII from a compound of Formula IX Formula IX

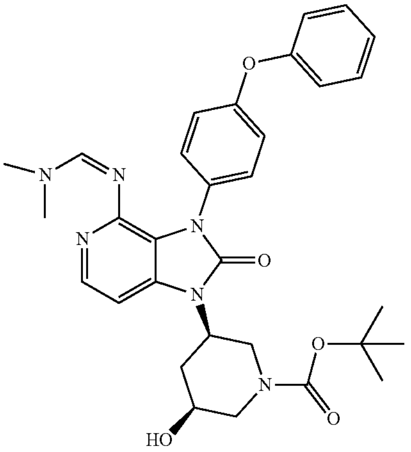

with triphenylphosphine and an azodicarboxylate.

In some embodiments, the azodicarboxylate is chosen from diethyl azodicarboxylate and diisopropyl azodicarboxylate. In some embodiments, the azodicarboxylate is diisopropyl azodicarboxylate.

In one embodiment, provided herein is a method of preparing a compound of Formula IV or salt thereof Formula IV

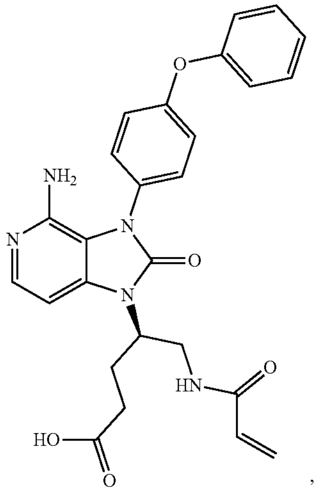

the method comprising reacting (4R)-5-amino-4-[4-amino-2-oxo-3-(4-phenoxyphenyl)imidazo[4,5-c]pyridin-1-yl] pentanoic acid with acryloyl chloride.

In some embodiments, the method further comprises preparing (4R)-5-amino-4-[4-amino-2-oxo-3-(4-phenoxyphenyl)imidazo[4,5-c]pyridin-1-yl]pentanoic acid, or a salt thereof, from (4R)-4-[4-[bis(tert-butoxycarbonyl)amino]-2-oxo-3-(4-phenoxyphenyl)imidazo[4,5-c]pyridin-1-yl]-5-(tert-butoxycarbonylamino)pentanoic acid by acid deprotection.

In some embodiments, the method further comprises preparing from (4R)-4-[4-[bis(tert-butoxycarbonyl)amino]-2-oxo-3-(4-phenoxyphenyl)imidazo[4,5-c]pyridin-1-yl]-5-(tert-butoxycarbonylamino)pentanoic acid, or a salt thereof, from tert-butyl (5R)-5-[4-[bis(tert-butoxycarbonyl)amino]-2-oxo-3-(4-phenoxyphenyl)imidazo[4,5-c]pyridin-1-yl]-2-oxo-piperidine-1-carboxylate by ring-opening in the presence of a base.

In some embodiments, the method further comprises preparing tert-butyl (5R)-5-[4-[bis(tert-butoxycarbonyl) amino]-2-oxo-3-(4-phenoxyphenyl)imidazo[4,5-c]pyridin-1-yl]-2-oxo-piperidine-1-carboxylate, or salt thereof, from tert-butyl (3R)-3-[4-[bis(tert-butoxycarbonyl)amino]-2-oxo-3-(4-phenoxyphenyl)imidazo[4,5-c]pyridin-1-yl]piperidine-1-carboxylate by an electrochemical reaction utilizing a mediator and an electrolyte. In some embodiments, the mediator is quinucleidine. In further embodiments, the electrolyte is tetramethylammonium tetrafluoroborate.

In one embodiment, provided herein is a method of preparing a compound of Formula V or salt thereof Formula V

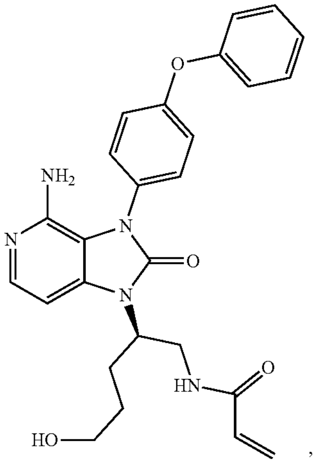

the method comprising reacting 4-amino-1-[(1R)-1-(aminomethyl)-4-hydroxy-butyl]-3-(4-phenoxyphenyl)imidazo [4,5-c]pyridin-2-one with acryloyl chloride.

In some embodiments, the method further comprises preparing 4-amino-1-[(1R)-1-(aminomethyl)-4-hydroxy-butyl]-3-(4-phenoxyphenyl)imidazo[4,5-c]pyridin-2-one, or salt thereof, from tert-butyl N-tert-butoxycarbonyl-N-[1-[(1R)-1-[(tert-butoxycarbonylamino)methyl]-4-hydroxy-butyl]-2-oxo-3-(4-phenoxyphenyl)imidazo[4,5-c]pyridin-4-yl]carbamate by acid deprotection.

In some embodiment, the method further comprises preparing tert-butyl N-tert-butoxycarbonyl-N-[1-[(1R)-1-[(tert-butoxycarbonylamino)methyl]-4-hydroxy-butyl]-2-oxo-3-(4-phenoxyphenyl)imidazo[4,5-c]pyridin-4-yl]carbamate, or salt thereof, from tert-butyl (5R)-5-[4-[bis(tert-butoxycarbonyl)amino]-2-oxo-3-(4-phenoxyphenyl)imidazo[4,5-c]pyridin-1-yl]-2-oxo-piperidine-1-carboxylate by ring-opening in the presence of a base.

In some embodiment, the method further comprises preparing tert-butyl (5R)-5-[4-[bis(tert-butoxycarbonyl) amino]-2-oxo-3-(4-phenoxyphenyl)imidazo[4,5-c]pyridin-1-yl]-2-oxo-piperidine-1-carboxylate, or salt thereof, from tert-butyl (3R)-3-[4-[bis(tert-butoxycarbonyl)amino]-2-oxo-3-(4-phenoxyphenyl)imidazo[4,5-c]pyridin-1-yl]piperidine-1-carboxylate by an electrochemical reaction utilizing a mediator and an electrolyte. In some embodiments, the mediator is quinucleidine. In further embodiments, the electrolyte is tetramethylammonium tetrafluoroborate.

TABLE 1

| Abbreviation | Definition |
|---|---|
| AcOEt and EtOAc | Ethyl acetate |
| ATP | Adenosine triphosphate |
| Boc | t-Butyloxycarbonyl protecting group |
| BTK | Bruton's tyrosine kinase |
| DCM | Dichloromethane |
| DIAD | Diisopropyl azodicarboxylate |
| DIEA | N,N-Diisopropylethylamine |
| DIPEA | N,N-diisopropylethylamine |
| DMAP | 4-Dimethylaminopyridine |
| DMF | N,N-Dimethylformamide |
| DMF DMA | N,N-dimethylformamide dimethyl acetal |
| DMSO | Dimethyl sulfoxide |
| HFIP | 1,1,1,3,3,3-hexafluoropropan-2-ol |
| HPLC | High-performance liquid chromatography |
| HOBt | Hydroxybenzotriazole |
| MeOH | Methanol |
| MS | Molecular sieve |
| MTBE | Methyl t-butyl ether |
| PMB | p-Methoxybenzyl protecting group |
| SGC | Silica gel chromatography |
| tBuOH | t-Butyl alcohol |
| TFA | Trifluoroacetic acid |
| THF | Tetrahydrofuran |
| TLC | Thin layer chromatography |

Abbreviations and names used in the following examples and elsewhere herein include: (TABLE 1 and TABLE 1-continued)

EXAMPLES

Example 1. Synthesis of 4-amino-1-[(3R,5S)-5-hydroxy-1-prop-2-enoyl-3-piperidyl]-3-(4-phenoxyphenyl)imidazo[4,5-c]pyridin-2-one and 4-amino-1-[(3R,5R)-5-hydroxy-1-prop-2-enoyl-3-piperidyl]-3-(4-phenoxyphenyl)imidazo[4,5-c]pyridin-2-one

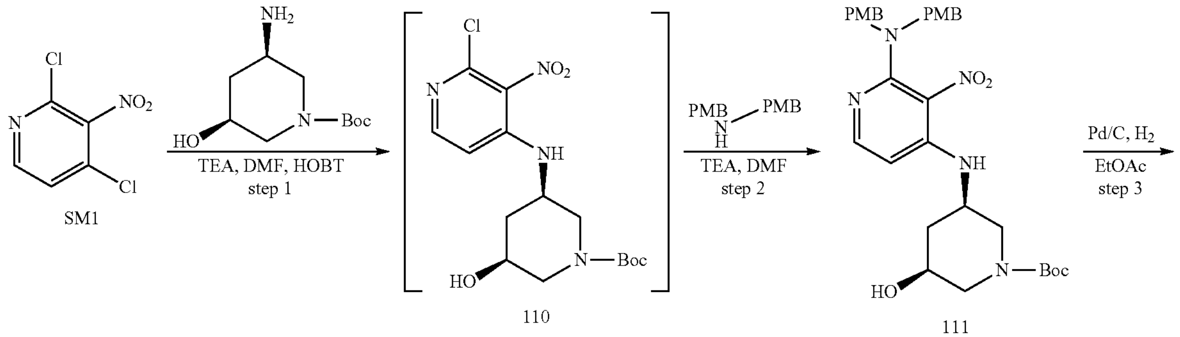

SM1 110 111

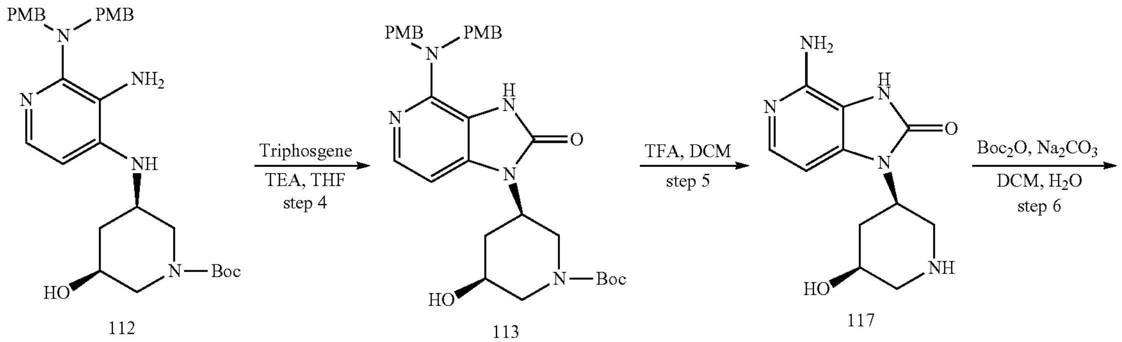

112 113 117

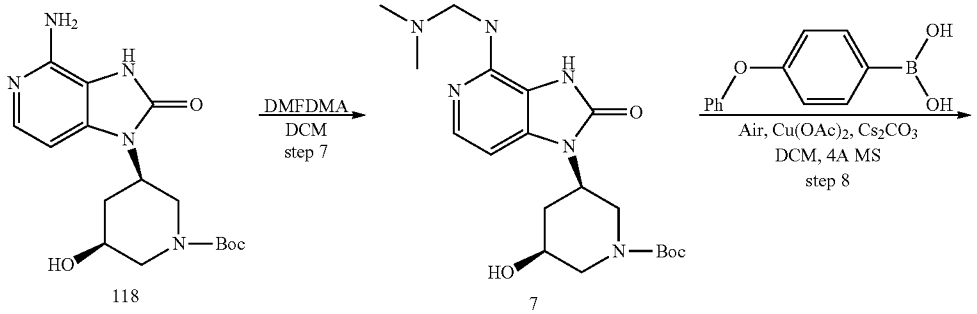

118 7

-continued
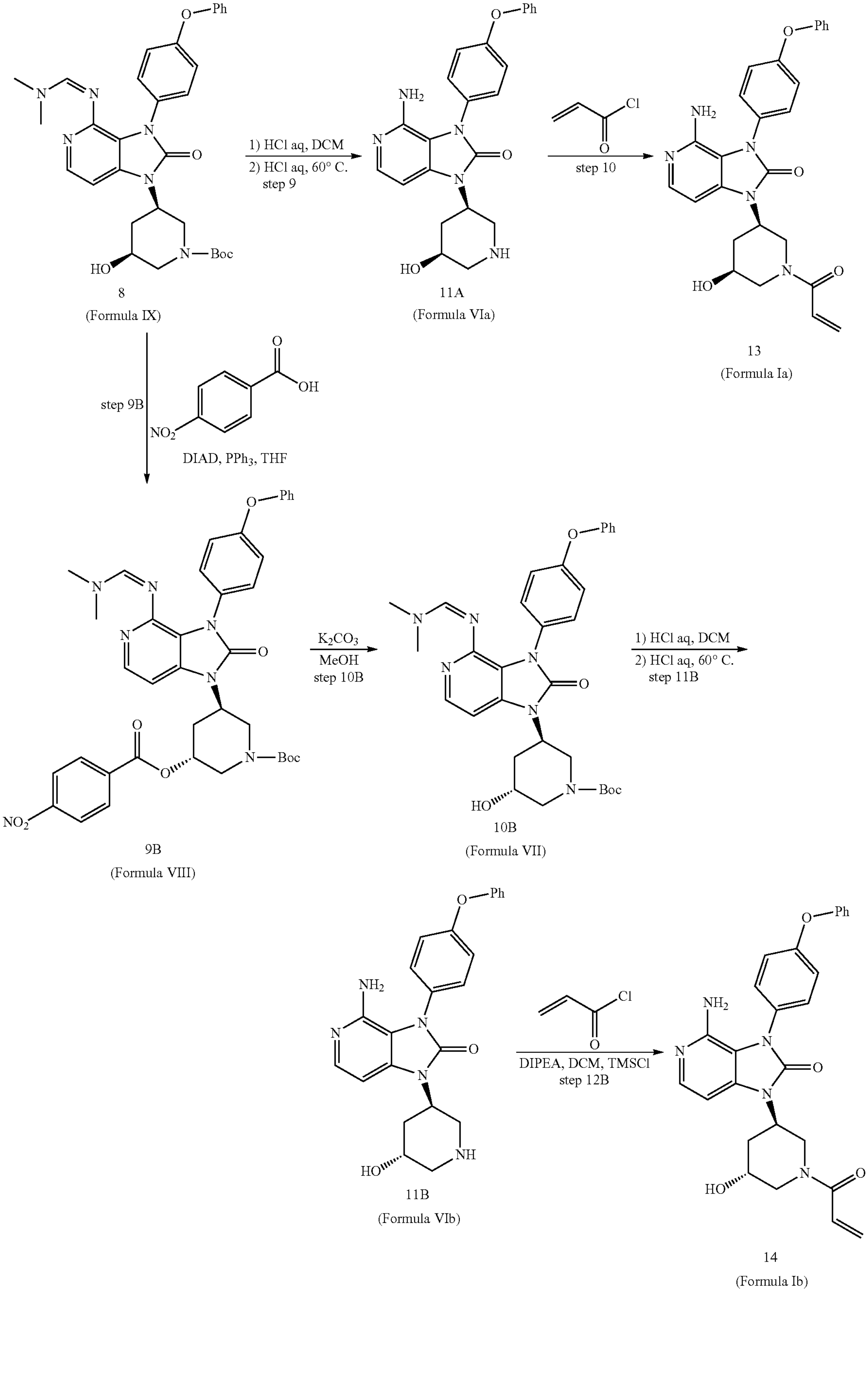
8
(Formula IX)
11A
(Formula VIa)
13
(Formula Ia)
9B
(Formula VIII)
10B
(Formula VII)
11B
(Formula VIb)
14
(Formula Ib)

Compounds of Formula Ia and Formula Ib were synthesized as shown in the Scheme above (referred to as compounds 13 and 14 respectively) and as described in more detail below.

Step 1: A reactor under nitrogen atmosphere was charged with DMF (21.5 mL). 2,4-dichloro 3 nitropyridine (SM1) (4.3 g, 22.28 mmol, 1.0 eq) was added at 20±5° C. After stirring for 5 minutes, triethylamine (4.75 mL, 33.81 mmol, 1.5 eq) was added and the mixture was cooled to 0±5° C. After adding HOBt (301 mg, 2.23 mmol, 0.1 eq), a solution of tert-butyl (3R,5S)-3-amino-5-hydroxy-piperidine-1-carboxylate (4.8 g, 22.28 mmol, 1.0 eq) in DMF (64.5 mL) was added dropwise. During addition of the reagents, the temperature was maintained between −10° C. and 0° C. The reaction mixture was stirred for 2 hours at 0±5° C., then for 4 hours at 20±5° C. HPLC analysis was performed to check for formation of tert-butyl (3R,5S)-3-[[2-(benzotriazol-1-yloxy)-3-nitro-4-pyridyl]amino]-5-hydroxy-piperidine-1-carboxylate (110).

Step 2: Next step was immediately carried out in one pot by charging triethylamine (4.75 mL, 33.81 mmol, 1.5 eq) and 1-(4-methoxyphenyl)-N-[(4-methoxyphenyl)methyl] methanamine (5.7 g, 22.28 mmol, 1.0 eq). The reaction solution was warmed to 40~45° C. and stirred at this temperature for 62 hours. HPLC analysis was performed to check that below 1% of intermediate was left. After cooling to 10~20° C., EtOAc (129 mL) and water (129 mL) were added to the solution, which was stirred for 30 minutes at 10~20° C. The organic phase was separated and washed with $CaCl_2$ aq. (5%, 43 mL×5). The organic phase was concentrated under vacuum below 35-C to afford tert-butyl (3R,5S)-3-[[2-[bis[(4-methoxyphenyl)methyl]amino]-3-nitro-4-pyridyl]amino]-5-hydroxy-piperidine-1-carboxylate (111) in EtOAc solution (brown solution) (94.3% purity), which was directly used in next step.

Step 3: Tert-butyl (3R,5S)-3-[[2-[bis[(4-methoxyphenyl) methyl]amino]-3-nitro-4-pyridyl]amino]-5-hydroxy-piperidine-1-carboxylate (111) (14.7 g, 24.76 mmol, 1 eq) (theoretical quantity) was dissolved in AcOEt (73.5 mL) and charged in a reactor. The reactor was inerted under vacuum and filled with nitrogen for five times, wet 10% Pd/C (2.64 g, 20 wt. %) was added, the reactor was inerted under vacuum and filled with nitrogen for five times and the reactor was then inerted under vacuum and filled with hydrogen for three times. The reaction mass was maintained under hydrogen pressure at 20±5° C. and stirred for 22 hours. HPLC analysis was performed to check the disappearance of starting material. The suspension was filtered, the cake was washed with EtOAc (73.5 mL×5). The filtrate was concentrated under vacuum to afford tert-butyl (3R,5S)-3-[[3-amino-2-[bis[(4-methoxyphenyl)methyl]amino]-4-pyridyl]amino]-5-hydroxy-piperidine-1-carboxylate (112) as a yellow foam solid (12 g, Yield=87%, 91.1% purity). This compound was used in next step without any further purification.

Step 4: In a reactor were charged THF (60 mL), tert-butyl (3R,5S)-3-[[2-[bis[(4-methoxyphenyl)methyl]amino]-3-nitro-4-pyridyl]amino]-5-hydroxy-piperidine-1-carboxylate (112) (12.0 g, 20.21 mmol, 1.0 eq) and triethylamine (4.4 mL, 40.42 mmol, 2.0 eq). The solution was stirred 10 min at 20±5° C., then triphosgene (1.07 mL, 6.46 mmol, 0.32 eq) was added in 3 batches and the resulting solution was stirred for 1.5 hour at 20~25° C. HPLC analysis was performed to check that below 1% of intermediate was left. The solution was concentrated at 24 mL, $CH_2Cl_2$ (120 mL) and $NaHCO_3$ aq. (60 mL) were added, the mixture was stirred for 10 minutes. The organic phase was separated and concentrated under vacuum below 40° C. to provide the crude product, which was purified by SGC ($CH_2Cl_2$/MeOH=30/1) to afford tert-butyl (3R,5S)-3-[4-[bis[(4-methoxyphenyl)methyl] amino]-2-oxo-3H-imidazo[4,5-c]pyridin-1-yl]-5-hydroxy-piperidine-1-carboxylate (113) as a foam solid (10 g, yield=74%, 97.1% purity).

Step 5: A solution of tert-butyl (3R,5S)-3-[4-[bis[(4-methoxyphenyl)methyl]amino]-2-oxo-3H-imidazo[4,5-c] pyridin-1-yl]-5-hydroxy-piperidine-1-carboxylate (113) (10.0 g, 16.95 mmol, 1.0 eq) in $CH_2Cl_2$ (70 mL) was stirred 10 minutes at 20±5° C., then cooled to 5±5° C.; TFA (10 mL) was added slowly so the temperature was kept ≤10° C. The reaction solution was stirred for 30 minutes at 5±5° C., warmed to 40±5° C., then stirred for 14 hours. HPLC analysis was performed to check that starting material was ≤1.0%. The reaction mass was cooled to 15~25° C. The pH was adjusted to 9-10 with $NaCO_3$ aq. The aqueous phase containing 4-amino-1-[(3R,5S)-5-hydroxy-3-piperidyl]-3H-imidazo[4,5-c]pyridin-2-one (117) was separated and kept to be engaged directly in next step.

Step 6: To the aqueous solution containing 4-amino-1-[(3R,5S)-5-hydroxy-3-piperidyl]-3H-imidazo[4,5-c]pyridin-2-one (117) cooled to 5±5° C. was added $CH_2Cl_2$ (40 mL), and a solution of $Boc_2O$ (3.7 g, 16.95 mmol, 1.0 eq) in $CH_2Cl_2$ (10 mL) dropwise at 5±5° C. The solution was warmed to 15~25° C. and stirred for 42 hours at 20~25° C. HPLC analysis was performed to check that starting material was ≤3.0%. The aqueous phase was separated, extracted with $CH_2Cl_2$ (100 mL×3) and THF (100 mL×2). The organic phases were combined, concentrated under vacuum below 35-C to afford 5.4 g of tert-butyl (3R,5S)-3-(4-amino-2-oxo-3H-imidazo[4,5-c]pyridin-1-yl)-5-hydroxy-piperidine-1-carboxylate (118) as a solid with 92.2% purity (contains $CH_2Cl_2$/THF).

Step 7: In a reactor were charged $CH_2Cl_2$ (21.6 mL) and tert-butyl (3R,5S)-3-(4-amino-2-oxo-3H-imidazo[4,5-c] pyridin-1-yl)-5-hydroxy-piperidine-1-carboxylate (118) (5.4 g, 15.45 mmol, 1.0 eq). The suspension was stirred for 10 minutes. After adding N,N-dimethylformamide dimethyl acetal (6.1 mL, 46.35 mmol, 3.0 eq) at 20±5° C., the solution became clear. Upon stirring for 20 hours at 20±5° C., a solid precipitated. HPLC analysis was performed to check that starting material was ≤2.0%. MTBE (54 mL) was added and the reaction mass was stirred for 2 hours at 20±5° C. The suspension was filtered. The cake was washed with MTBE (21.6 mL), dried under vacuum at 35±5° C. for 8 hours to afford tert-butyl (3R,5S)-3-[4-[(Z)-dimethylaminomethyleneamino]-2-oxo-3H-imidazo[4,5-c]pyridin-1-yl]-5-hydroxy-piperidine-1-carboxylate (7) as an off-white solid (4.3 g, Yield=83%, 93.4% purity).

Step 8: In a reactor at 20±5° C. were charged $CH_2Cl_2$ (75 mL), $Cu(OAc)_2$ (561.2 mg, 3.09 mmol, 0.5 eq), 2,2'-Dipyridyl (482 mg, 3.09 mmol, 0.5 eq), $Cs_2CO_3$ (4.02 g, 12.36 mmol, 2.0 eq.), 4A MS (2.5 g, 1.0 w/w) and tert-butyl (3R,5S)-3-[4-[(Z)-dimethylaminomethyleneamino]-2-oxo-3H-imidazo[4,5-c]pyridin-1-yl]-5-hydroxy-piperidine-1-carboxylate (7) (2.5 g, 6.18 mmol, 1.0 eq). Compressed air (21% Oxygen and 79% Nitrogen) was bubbled to the reaction mass for 30 minutes at 20±5° C. To the reaction mixture, 4-Phenoxyphenylboronic (1.98 g, 9.27 mmol, 1.5 eq.) was added in four batches over 1.5 hours at 15~25° C. Compressed air (21% Oxygen and 79% Nitrogen) was bubbled to the reaction mass for 5 hours at 20±5° C. HPLC analysis was performed to check that starting material was ≤5.0%. The suspension was filtered, the cake was washed with $CH_2Cl_2$ (25 mL×2). The filtrate was concentrated and the crude product was purified SGC ($CH_2Cl_2$/MeOH=50/1)

to afford tert-butyl (3R,5S)-3-[4-[(Z)-dimethylaminomethyleneamino]-2-oxo-3-(4-phenoxyphenyl)imidazo[4,5-c]pyridin-1-yl]-5-hydroxy-piperidine-1-carboxylate (Compound of Formula IX, also referred to as (8) above) as solid with 97.5% purity and 47.2% yield.

Step 9: Tert-butyl (3R,5S)-3-[4-[(Z)-dimethylaminomethyleneamino]-2-oxo-3-(4-phenoxyphenyl)imidazo[4,5-c]pyridin-1-yl]-5-hydroxy-piperidine-1-carboxylate (8) (0.3 g, 0.52 mmol, 1.0 eq.) was dissolved in $CH_2Cl_2$ (1.5 mL). To this solution, aqueous HCl solution (3 N, 3 mL) was added dropwise at 20±5° C. The solution was stirred at 30~35° C. for 2 hours and at 60~65° C. for 14 hours. HPLC analysis was performed to check that starting material was ≤1.0%. To the solution cooled to 20~25° C., $CH_2Cl_2$ (15 mL) and water (45 mL) were added. The solution was stirred for 10 minutes, then the aqueous phase was separated, extracted with $CH_2Cl_2$ (30 mL), and the pH of the aqueous phase was adjusted to 9-10 with $Na_2CO_3$ aq. The aqueous phase became pink. After stirring for 30 minutes, the organic phase was extracted and washed with brine (15 mL), dried over $Na_2SO_4$, filtered to provide 4-amino-1-[(3R,5S)-5-hydroxy-3-piperidyl]-3-(4-phenoxyphenyl)imidazo[4,5-c]pyridin-2-one (Compound of Formula VIa, also referred to as (11A) above) (81% purity) in solution in $CH_2Cl_2$. It was engaged directly in the Step 10.

Step 10: The previous solution of 4-amino-1-[(3R,5S)-5-hydroxy-3-piperidyl]-3-(4-phenoxyphenyl)imidazo[4,5-c]pyridin-2-one (11A) (164 mg, 0.39 mmol, 1 eq) in $CH_2Cl_2$ was cooled to 0±5° C., N,N-diisopropylethylamine (133 μL, 0.78 mmol, 2.0 eq) and trimethyl silyl chloride (50 μL, 0.39 mmol, 1.0 eq) in $CH_2Cl_2$ (2.5 ml) were charged, the solution was stirred for 30 minutes at 0±5° C. After cooling the solution to −20±5° C., acryloyl chloride (32 μL, 0.39 mmol, 1.0 eq) in $CH_2Cl_2$ (5 ml) was added dropwise. The reaction was quenched with water (20 mL), and the organic phase was separated and concentrated under vacuum below 35° C. to get the crude product. The crude product was purified by Prep-TLC ($CH_2Cl_2$/EtOH=15/1), the fraction was concentrated and $CH_2Cl_2$ was switched with EtOH. The solution was concentrated to 10 mL and n-heptane (15 ml) was charged. The solution was then concentrated to 10 mL and a solid precipitated. The precipitate was filtered to afford 80 mg of 4-amino-1-[(3R,5S)-5-hydroxy-1-prop-2-enoyl-3-piperidyl]-3-(4-phenoxyphenyl)imidazo[4,5-c]pyridin-2-one (Compound of Formula Ia, also referred to as (13) above) as an off-white solid with 98.1% purity and 43% yield. 1H NMR spectrum (500 MHz, DMSO D6, δ in ppm): 7.77 (d, 1H); 7.51-7.41 (m, 4H); 7.22 (t, 1H); 7.18-7.11 (m, 4H); 6.96 (br. m, 1H); 6.81 (m, 1H); 6.15 (d, 1H); 5.71 (dd, 1H); 5.28 (br. s, 1H); 4.83 (br. m, 21-1); 4.58 (br. d, 0.5H); 4.47 (br. d, 0.5H); 4.25 (br. qd, 1H); 4.15 (br. d, 0.5H); 4.1 (br. d, 0.5H); 3.69 (br. t, 0.5H); 3.60 (m, 1H); 3.27 (br. t, 0.5H); 2.95 (br. t, 0.5H); 2.49 (br. t, 0.5H); 2.28 (m, 1H); 2.13 (br. m, 1H)

Step 9B: In a reactor inerted with azote, THF (12.5 mL), DIAD (683 μL, 3.48 mmol, 4.0 eq), and $Ph_3P$ (912 mg, 3.48 mmol, 4.0 eq) were charged. The reaction mass was cooled to 0~5° C., then tert-butyl (3R,5S)-3-[4-[(Z)-dimethylaminomethyleneamino]-2-oxo-3-(4-phenoxyphenyl)imidazo[4,5-c]pyridin-1-yl]-5-hydroxy-piperidine-1-carboxylate (8) (0.5 g, 0.87 mmol, 1.0 eq) was added to the reactor. The reaction mass was stirred for 10 minutes at 0~5° C., 4-nitro benzoic acid (291 mg, 1.74 mmol, 2.0 eq) was added to the reactor and the reaction was stirred a further 2 hours at 0~5° C. The reaction mixture was then stirred 14 hours at 15~20° C., concentrated under vacuum below 35° C. The residual was purified with SGC ($CH_2Cl_2$/MeOH=50/1) to afford crude tert-butyl (3R,5R)-3-[4-[(Z)-dimethylaminomethyleneamino]-2-oxo-3-(4-phenoxyphenyl)imidazo[4,5-c]pyridin-1-yl]-5-(4-nitrobenzoyl)oxy-piperidine-1-carboxylate (Compound of Formula VIII, also referred to as (9B) above) as a foam solid (purity 87%) which contains $Ph_3PO$. The $Ph_3PO$ was hard to separate and this intermediate was not further purified.

Step 10B: MeOH (9 mL), tert-butyl (3R,5R)-3-[4-[(Z)-dimethylaminomethyleneamino]-2-oxo-3-(4-phenoxyphenyl)imidazo[4,5-c]pyridin-1-yl]-5-(4-nitrobenzoyl)oxy-piperidine-1-carboxylate (9B) (0.45 g, 0.62 mmol, 1.0 eq) and $K_2CO_3$ (258 mg, 1.87 mmol, 3.0 eq) were charged to a flask. The reaction mixture was stirred for 14 hours at 15~20° C. HPLC analysis showed that no starting material was left. The suspension was filtered, the cake was washed with MeOH (2.25 mL), the filtrate was concentrated under vacuum below 35° C. to provide the crude product. The crude product was purified by SGC ($CH_2Cl_2$/MeOH=50/1) to afford tert-butyl (3R,5R)-3-[4-[(Z)-dimethylaminomethyleneamino]-2-oxo-3-(4-phenoxyphenyl)imidazo[4,5-c]pyridin-1-yl]-5-hydroxy-piperidine-1-carboxylate (Compound of Formula VII, also referred to as (10B) above) (0.16 g, yield 44%, 98.2% purity) as a powder solid.

Step 11B: To a flask were charged $CH_2Cl_2$ (1 mL), tert-butyl (3R,5R)-3-[4-[(Z)-dimethylaminomethyleneamino]-2-oxo-3-(4-phenoxyphenyl)imidazo[4,5-c]pyridin-1-yl]-5-hydroxy-piperidine-1-carboxylate (10B) (0.16 g, 0.28 mmol, 1 eq) and HCl aq (3.0M, 2 mL). The solution was stirred for 2 hours at 25~30° C., then for 14 hours at 60~65° C. HPLC analysis showed that no starting material remained. The reaction mixture was cooled to 15~20° C., and $CH_2Cl_2$ (15 ml) and $H_2O$ (30 ml) were added to the flask. The organic phase was separated. $CH_2Cl_2$ (30 ml) was added to the aqueous phase, the pH value of the aqueous phase was adjusted to 9-10 with saturated $Na_2CO_3$ aq. The organic phase was separated, the aqueous phase was re-extracted with $CH_2Cl_2$ (30 mL×2). The different organic phases were gathered, washed with brine (10 mL), dried with $Na_2SO_4$, filtered and concentrated under vacuum below 35° C. to afford 0.11 g of crude material 4-amino-1-[(3R,5R)-5-hydroxy-3-piperidyl]-3-(4-phenoxyphenyl)imidazo[4,5-c]pyridin-2-one (Compound of Formula VIb, also referred to above as (11B)) as a foam solid which was not further purified and engaged in Step 12B directly.

Step 12B: To a solution of 4-amino-1-[(3R,5R)-5-hydroxy-3-piperidyl]-3-(4-phenoxyphenyl)imidazo[4,5-c]pyridin-2-one (11B) (0.11 g, 0.26 mmol, 1 eq) in $CH_2Cl_2$ (44 mL) was added N,N-diisopropylethylamine (177 L, 1.04 mmol, 4.0 eq). The solution was cooled to −5~0° C., and a solution of trimethyl silyl chloride (33 μL, 0.26 mmol, 1.0 eq) in $CH_2Cl_2$ (2.5 ml) was added dropwise. The solution was stirred 30 minutes at −5~0° C., cooled to −25~−20° C. Acryloyl chloride (27.5 μL, 0.34 mmol, 1.3 eq) in $CH_2Cl_2$ (2.5 mL) was added dropwise. The reaction was stirred for 10 minutes, warmed to 0~5° C., and quenched with water (20 mL). The organic phase was separated, washed with brine (10 mL) and concentrated under vacuum below 35° C. to get the crude material. The crude product was purified by prep-TLC ($CH_2Cl_2$/MeOH=15/1) to get 4-amino-1-[(3R,5R)-5-hydroxy-1-prop-2-enoyl-3-piperidyl]-3-(4-phenoxyphenyl)imidazo[4,5-c]pyridin-2-one (Compound of Formula Ib, also referred to above as (14)) (63 mg, Yield=51%, 99.1% purity) as an off-white powder solid. LC/HRMS: 472.1821 (M+H)+, 470.1790 $(M-H)^-$. 1H NMR spectrum (500 MHz, DMSO D6, δ in ppm): 7.76 (d, 1H); 7.50-7.42 (m, 4H); 7.22 (t, 1H), 7.18-7.11 (m, 4H); 6.90 (d, 1H); 6.79 (dd, 1H); 6.13 (dd, 1H); 5.68 (dd, 1H); 5.05 (br. d, 0.75H);

4.96 (br. d, 0.25H); 4.81 (br. s, 2K); 4.65 (br. m, 0.25H); 4.59-4.46 (m, 1.75H); 4.19 (br. d, 0.25H); 4.07 (br. s, 1H); 3.97 (br. d, 0.75H); 3.72 (t, 0.25H); 3.38 (d, 0.75H); 3.32 (m, 0.75H); 2.90 (d, 0.25H); 2.53 (m, 1H); 1.92 (br. d, 1H).

Example 2. Synthesis of 4-amino-3-(4-phenoxyphenyl)-1-[(3R)-1-(2,3-dihydroxypropanoyl)-3-piperidyl]imidazo[4,5-c]pyridin-2-one

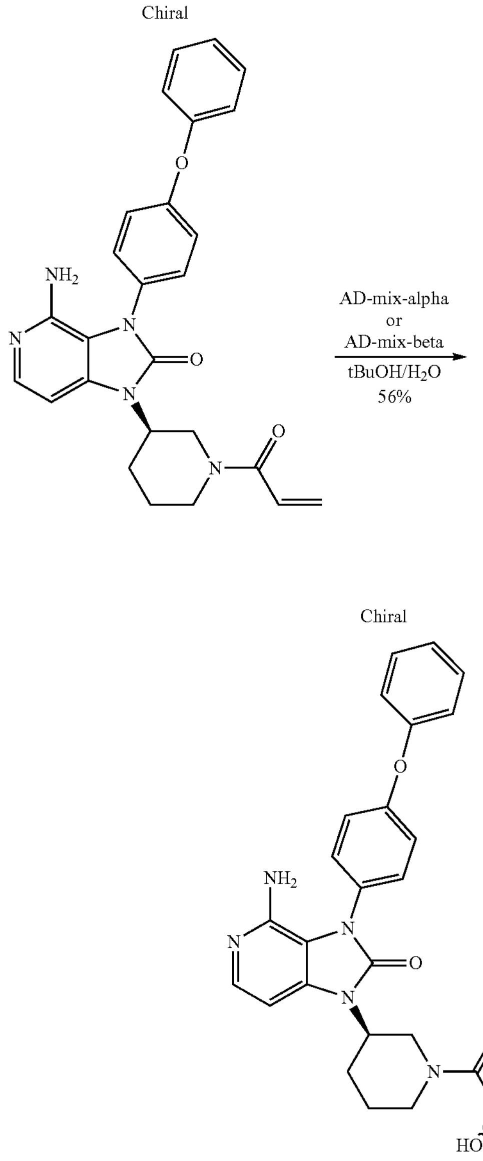

Formula IIa + Formula IIb

As shown in the scheme above, Compounds of Formula IIa and IIb were prepared from 4-amino-3-(4-phenoxyphenyl)-1-[(3R)-1-prop-2-enoyl-3-piperidyl]imidazo[4,5-c]pyridin-2-one using AD-Mix-alpha (i.e., (DHQ)2PHAL (hydroquinine 1,4-phthalazinediyl diether, Sigma Aldrich Cat. No. 392723) 0.0016 mole; potassium carbonate, powder 0.4988 mole; potassium ferricyanide 0.4988 mole; potassium osmate dihydrate 0.0007 mol) or AD-Mix-beta (i.e., (DHQD)2PHAL (Sigma Aldrich Cat. No. 392731) 0.0016 mole; potassium carbonate, powder 0.4988 mole; potassium ferricyanide 0.4988 mole; potassium osmate dihydrate 0.0007 mole).

The starting material, 4-amino-3-(4-phenoxyphenyl)-1-[(3R)-1-prop-2-enoyl-3-piperidyl]imidazo[4,5-c]pyridin-2-one, was prepared according to the procedure described in U.S. Pat. No. 9,688,676 at Example 3.

To make the Compounds of Formula IIa and IIb, a suspension of AD-Mix-alpha (154 mg) or AD-Mix-beta (154 mg) in water/tBuOH (1/1, 1 mL/1 mL) was stirred for about 10 minutes until dissolution of the solids. To the yellow solution, under an argon atmosphere, was added the starting material, 4-amino-3-(4-phenoxyphenyl)-1-[(3R)-1-prop-2-enoyl-3-piperidyl]imidazo[4,5-c]pyridin-2-one. Because the starting material was insoluble in the mixture, a yellow suspension was obtained. This suspension was stirred for 20 hours at room temperature. The advancement of the reaction was checked by TLC (AcOEt/MeOH 10/1). The reaction mixture was hydrolyzed with $Na_2SO_3$, stirred for 20 minutes, extracted with $CH_2Cl_2$. The organic phase was separated, dried over $MgSO_4$, filtered and concentrated under vacuum to afford the crude product. The crude product was purified by SCX (strong cation exchange) column (MeOH, then $NH_3$ 3.5N solution in MeOH) to provide a transparent oil 4-amino-3-(4-phenoxyphenyl)-1-[(3R)-1-(2,3-dihydroxypropanoyl)-3-piperidyl]imidazo[4,5-c]pyridin-2-one as a mixture of two diastereoisomers which were separated by chiral chromatography to provide the Compound of Formula IIa (98% purity) and the Compound of Formula IIb (98% purity). IIa: 1H NMR (500 MHz, DMSO-d6) (2 rotamers 50/50) 6 ppm 1.45-1.65 (m, 1H), 1.80-1.95 (m, 2H), 2.45 (m, 1H), 3.10 (m, 0.5H), 3.25 (m, 0.5H), 3.40-3.55 (m, 2H), 3.67 (m, 0.5H), 4.05-4.50 (m, 4.5H), 4.62 (t, J=4 Hz, 0.5H), 4.77 (t, J=4 Hz, 0.5H), 4.80 (m, 2H), 4.95 (d, J=4 Hz, 0.5H), 5.01 (d, J=4 Hz, 0.5H), 6.90-6.96 (m, 1H), 7.15 (m, 4H), 7.22 (t, J=7 Hz, 1H), 7.45 (m, 4H), 7.75 (d, J=5 Hz, 1H).

IIb: 1H NMR (500 MHz, DMSO-d6) (2 rotamers 50/50) 6 ppm 1.45-1.65 (m, 1H), 1.80-1.95 (m, 2H), 2.45 (m, 1H), 3.10 (m, 0.5H), 3.25 (m, 0.5H), 3.40-3.55 (m, 2H), 3.67 (m, 0.5H), 4.05-4.50 (m, 4.5H), 4.65 (t, J=4 Hz, 0.5H), 4.76 (t, J=4 Hz, 0.5H), 4.80 (m, 2H), 4.98 (m, 1H), 6.90-6.96 (m, 1H), 7.15 (m, 4H), 7.22 (t, J=7 Hz, 1H), 7.45 (m, 4H), 7.75 (d, J=5 Hz, 1H) LC/MS: 490 (M+H)+.

Example 3. Synthesis of (R)-5-acrylamido-4-(4-amino-2-oxo-3-(4-phenoxyphenyl)-2,3-dihydro-1H-imidazo[4,5-c]pyridin-1-yl)pentanoic acid
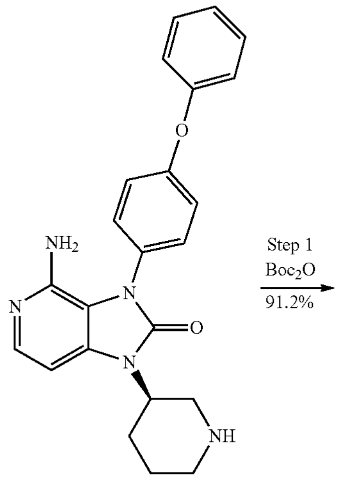
(1)
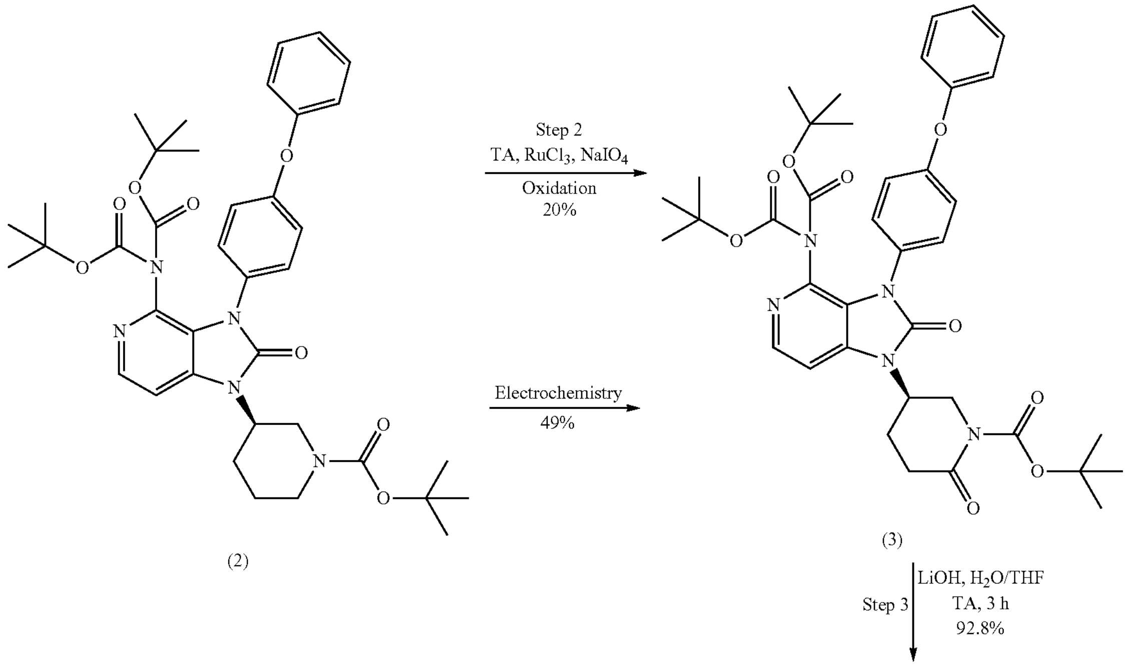
(2)
(3)

-continued

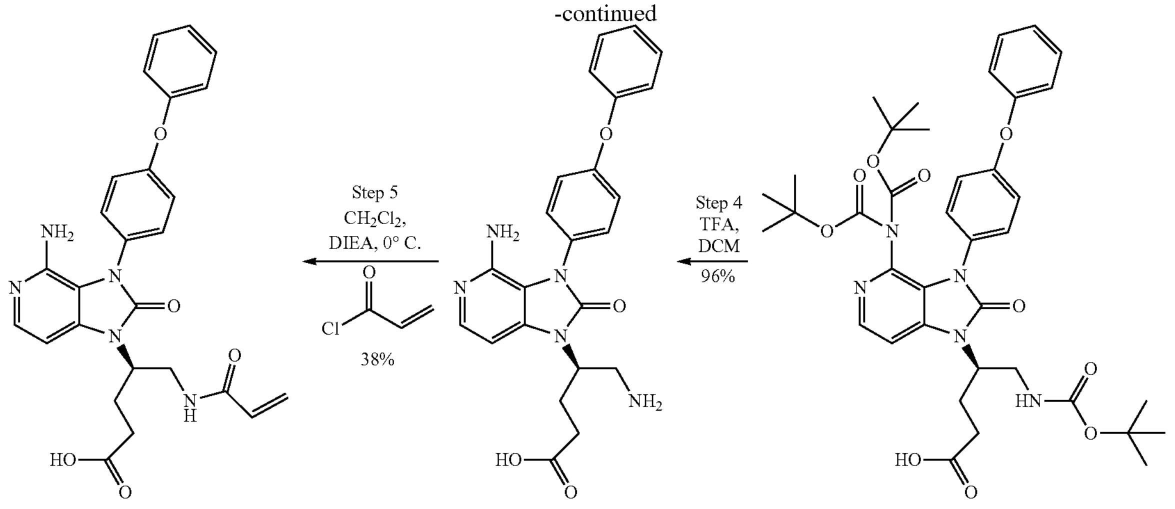

(6)
Formula IV
(5)
(4)

The Compound of Formula IV (referred to above as compound (6)) was prepared as shown in the scheme above and as described in more detail below. The starting material, 4-amino-3-(4-phenoxyphenyl)-1-[(3R)-3-piperidyl]imidazo [4,5-c]pyridin-2-one (1), was prepared according to the procedure described in U.S. Pat. No. 9,688,676 at Example 2. 4-amino-3-(4-phenoxyphenyl)-1-[(3R)-3-piperidyl]imidazo[4,5-c]pyridin-2-one (1) was then converted to an oxalate salt by adding DCM to Compound (1). The solution was switched to EtOH and the resulting solution was reacted with oxalic acid. After filtration, the crude solid was slurried in MTBE, filtered, and dried to afford the oxalate salt of Compound (1).

Step 1: To a flask under an argon atmosphere were added $CH_2Cl_2$ and the oxalate salt of 4-amino-3-(4-phenoxyphenyl)-1-[(3R)-3-piperidyl]imidazo[4,5-c]pyridin-2-one (1.3 g, 2.66 mmol, 1 eq). To the suspension was then charged DMAP (487 mg, 3.98 mmol, 1.5 eq), DIEA (1.35 mL, 7.97 mmol, 3 eq) and $Boc_2O$ (2.90 g, 13.28 mmol, 5 eq). The starting material dissolved, and the reaction mass became limpid. The solution was stirred at room temperature for 20 hours. The reaction mass was hydrolyzed with water, extracted with $CH_2Cl_2$. The organic phase was separated, dried over $MgSO_4$, filtered and concentrated under vacuum to afford the crude product. The crude product was purified by flash chromatography ($SiO_2$, Hep/AcOEt (1/1)) to give tert-butyl (3R)-3-[4-[bis(tert-butoxycarbonyl)amino]-2-oxo-3-(4-phenoxyphenyl)imidazo[4,5-c]pyridin-1-yl]piperidine-1-carboxylate (2) (1.86 g, yield=91.2%).

Step 2: To a solution of tert-butyl (3R)-3-[4-[bis(tert-butoxycarbonyl)amino]-2-oxo-3-(4-phenoxyphenyl)imidazo[4,5-c]pyridin-1-yl]piperidine-1-carboxylate (2) (1 g, 1.42 mmol, 1 eq) in $MeCN/H_2O/CCl_4$ (15 mL/20 mL/15 mL) were added $NaIO_4$ (1.22 g, 5.7 mmol, 4 eq) and $RuCl_3 \cdot xH_2O$ (32 mg, 142 mol, 0.1 eq) in that order. The reaction was a light brown mixture. After stirring for 1 hour at room temperature, some more $NaIO_4$ (152 mg, 0.7 mmol, 0.25 eq) was added. The reaction mass was stirred 24 hours at room temperature, it was dark brown. Upon hydrolyzing with aqueous $Na_2S_2O_5$ and stirring for 30 minutes, the solution became light yellow. It was extracted with AcOEt. The organic phase was separated, dried over $MgSO_4$, filtered and concentrated under vacuum to provide the crude product. Purification of the crude product by flash chromatography ($SiO_2$, Hep/AcOEt (1/1)) provided tert-butyl (3R)-3-[4-[bis(tert-butoxycarbonyl)amino]-2-oxo-3-(4-phenoxyphenyl)imidazo[4,5-c]pyridin-1-yl]piperidine-1-carboxylate (starting material) (450 mg, yield=45%) and tert-butyl (5R)-5-[4-[bis(tert-butoxycarbonyl)amino]-2-oxo-3-(4-phenoxyphenyl)imidazo[4,5-c]pyridin-1-yl]-2-oxo-piperidine-1-carboxylate (desired product) (3) (200 mg, yield=20%).

Step 2: Electrochemical process—Using Electrasyn 2.0 (IKA) with 20 mL vial setup, to a solution of tert-butyl (3R)-3-[4-[bis(tert-butoxycarbonyl)amino]-2-oxo-3-(4-phenoxyphenyl)imidazo[4,5-c]pyridin-1-yl]piperidine-1-carboxylate (2) (300 mg, 0.43 mmol, 1 eq) in MeCN (12 mL) were added quinuclidine as a mediator (2 eq, 0.86 mmol, 95 mg), 1,1,1,3,3,3-hexafluoropropan-2-ol ("HFIP") (11 eq, 4.70 mmol, 790 mg) and tetramethylammonium tetrafluoroborate as an electrolyte (2.05 eq, 0.88 mmol, 141 mg). Vial cap set: (Working Electrode) RVC—Reticulated Vitreous Carbon Foam as the anode and Ni Foam as the cathode. The electrochemical reaction was conducted in galvanostatic mode; constant current of 8 mA with no polarity switch. Total load 16 Faradays per mol at room temperature. The reaction was monitored by LC/MS. The reaction was poured into ice water, then a 1M solution of sodium thiosulfate was added. The aqueous phase was washed with ethyl acetate. The organic phase was separated, dried over sodium sulfate, filtered and concentrated under vacuum to provide the crude product. Purification by flash chromatography on silica gel, elution mixture ethyl acetate/pentane (70/30), provided the expected product—tert-butyl (5R)-5-[4-[bis(tert-butoxycarbonyl)amino]-2-oxo-3-(4-phenoxyphenyl)imidazo[4,5-c]pyridin-1-yl]-2-oxo-piperidine-1-carboxylate (3) (150 mg, yield=49%).

Step 3: To a solution of tert-butyl (5R)-5-[4-[bis(tert-butoxycarbonyl)amino]-2-oxo-3-(4-phenoxyphenyl)imidazo[4,5-c]pyridin-1-yl]-2-oxo-piperidine-1-carboxylate (3) (820 mg, 1.15 mmol, 1 eq) in $THF/H_2O$ (30 mL/30 mL) was added LiOH (471 mg, 19.4 mmol, 17 eq). The solution was stirred 3 hours at room temperature. The reaction mixture was hydrolyzed with HCl aq 1N until pH=1-2, and then extracted with AcOEt. The organic phase was separated, dried over $MgSO_4$, filtered and concentrated under vacuum to afford the desired compound: (4R)-4-[4-[bis(tert-butoxycarbonyl)amino]-2-oxo-3-(4-phenoxyphenyl)imidazo[4,5-c]pyridin-1-yl]-5-(tert-butoxycarbonylamino)pentanoic acid (4) (780 mg, Yield=92.8%).

Step 4: In a flask under argon atmosphere, were charged $CH_2Cl_2$ (5 mL), (4R)-4-[4-[bis(tert-butoxycarbonyl)amino]-2-oxo-3-(4-phenoxyphenyl)imidazo[4,5-c]pyridin-1-yl]-5-(tert-butoxycarbonylamino)pentanoic acid (720 mg, 0.98 mmol, 1 eq) (4), and TFA (2 mL). The mixture was stirred 6 hours at room temperature. After evaporation of the $CH_2Cl_2$ and the TFA and drying under high vacuum for 10 hours, (4R)-5-amino-4-[4-amino-2-oxo-3-(4-phenoxyphenyl)imidazo[4,5-c]pyridin-1-yl]pentanoic acid (5) (410 mg, 96%) was obtained. It was not further purified and was engaged in next step as is.

Step 5: To a suspension of (4R)-5-amino-4-[4-amino-2-oxo-3-(4-phenoxyphenyl)imidazo[4,5-c]pyridin-1-yl]pentanoic acid (5) (425 mg, 0.98 mmol, 1 eq) and $CH_2Cl_2$ (6 mL), DMF (0.5 mL) was added in order to solubilize the starting material. Then, the reaction solution was cooled to 0° C., DIEA (343 µL, 1.96 mmol, 2 eq) was charged and a solution of acryloyl chloride (41 µL, 0.49 mmol, 0.5 eq) in $CH_2Cl_2$ (2 mL) was added dropwise. The solution was allowed to warm to room temperature and stirred for 2 hours. The reaction mass was concentrated under vacuum and directly purified by preparative HPLC, then by supercritical HPLC, to obtain (4R)-4-[4-amino-2-oxo-3-(4-phenoxyphenyl)imidazo[4,5-c]pyridin-1-yl]-5-(prop-2-enoylamino)pentanoic acid (Compound of Formula IV, also referred to above as (6)) (180 mg, Yield=38%, 98% purity). 1H NMR (500 MHz, DMSO-d6) δ ppm 2.02 (m, 1H), 2.17 (m, 2H), 2.28 (m, 1H), 3.65 (m, 2H), 4.36 (m, 1H), 4.78 (s, 2H), 5.53 (dd, J=8, 2 Hz, 1H), 6.02 (dd, J=17, 2 Hz, 1H), 6.09 (dd, J=17, 8 Hz, 1H), 6.65 (m, 1H), 7.15 (d, J=8 Hz, 4H), 7.21 (t, J=7 Hz, 1H), 7.45 (m, 4H), 7.71 (d, J=5 Hz, 1H), 8.28 (t, J=6 Hz, 1H) LC/MS: 488.2 (M+H)+/486.1 $(M-H)^-$.

Example 4. Synthesis of (R)-N-(2-(4-amino-2-oxo-3-(4-phenoxyphenyl)-2,3-dihydro-1H-imidazo[4,5-c]pyridin-1-yl)-5-hydroxypentyl)acrylamide

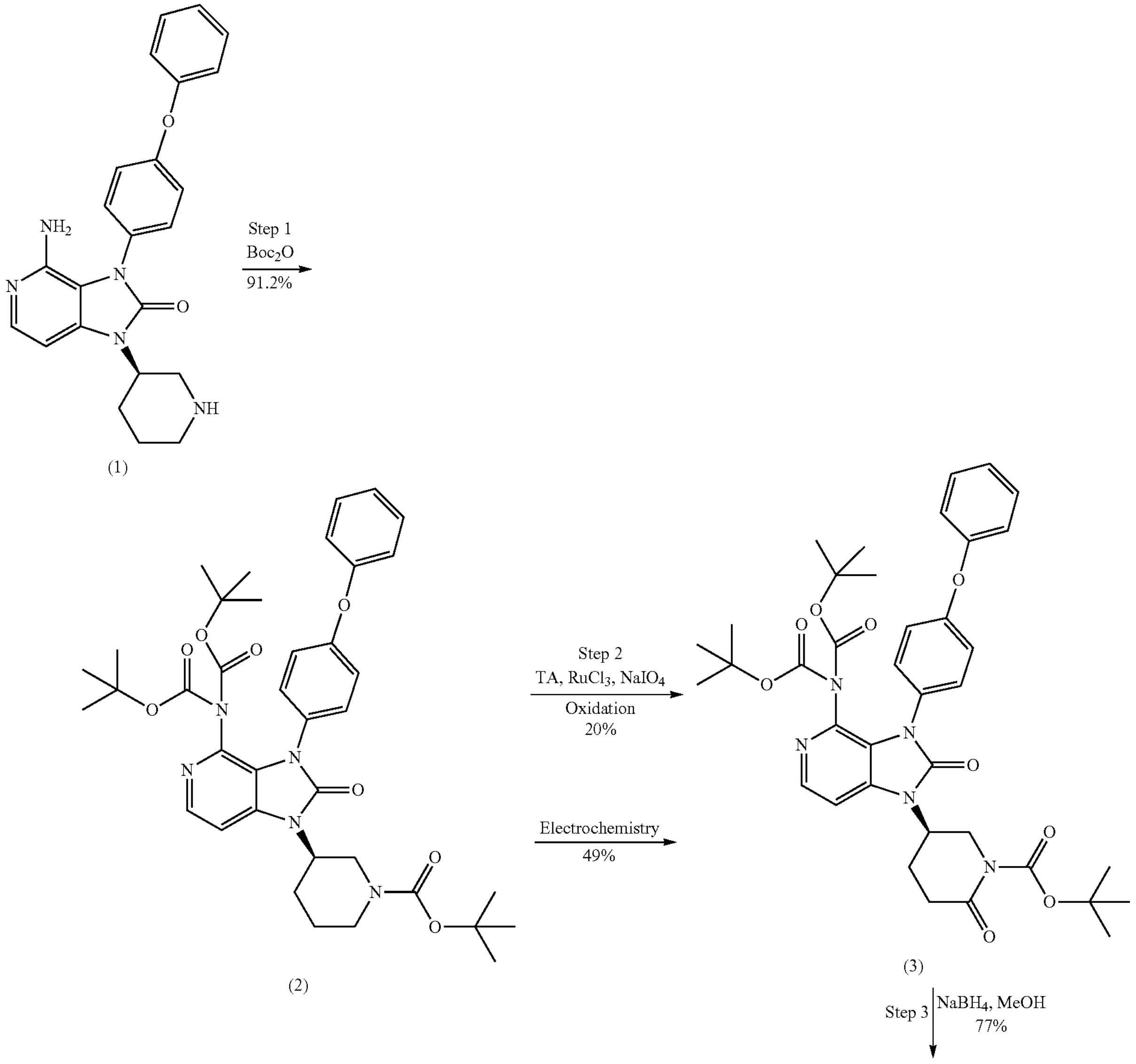

(1)

(2)

(3)

-continued

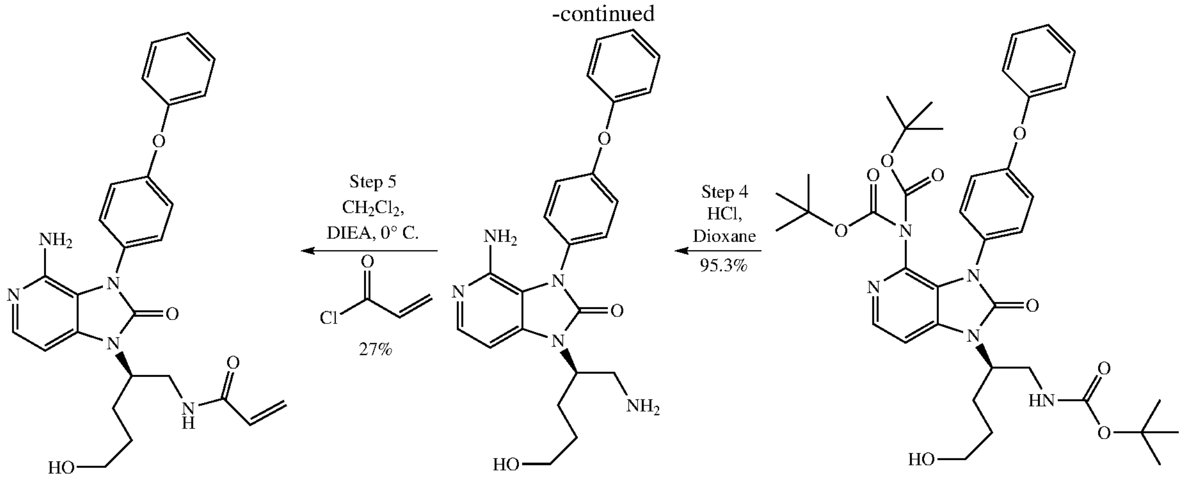

(6)
Formula V
(5)
(4)

The Compound of Formula V (referred to above as compound (6)) was prepared as shown in the scheme above and as discussed in more detail below.

Steps 1 and 2 were conducted as described in steps 1 and 2 of Example 3. Step 3: To a flask under argon atmosphere at room temperature, were added tert-butyl (5R)-5-[4-[bis(tert-butoxycarbonyl)amino]-2-oxo-3-(4-phenoxyphenyl)imidazo[4,5-c]pyridin-1-yl]-2-oxo-piperidine-1-carboxylate (3) (280 mg, 0.39 mmol, 1 eq), MeOH (8 mL), $NaBH_4$ (148 mg, 3.9 mmol, 10 eq). The reaction mixture was stirred at room temperature for 3 hours, and then hydrolyzed with $H_2O$. The organic phase was separated, dried over $MgSO_4$, filtered and concentrated under vacuum to afford the desired compound tert-butyl (3R)-3-[4-[bis(tert-butoxycarbonyl)amino]-2-oxo-3-(4-phenoxyphenyl)imidazo[4,5-c]pyridin-1-yl]piperidine-1-carboxylate (4) (281 mg, Yield=77%). It was not further purified and directly engaged in the next step.

Step 4: To the starting material tert-butyl N-tert-butoxycarbonyl-N-[1-[(1R)-1-[(tert-butoxycarbonylamino)methyl]-4-hydroxy-butyl]-2-oxo-3-(4-phenoxyphenyl)imidazo[4,5-c]pyridin-4-yl]carbamate (4) (216 mg, 0.30 mmol, 1 eq) was added HCl in dioxane (15 mL). The solution was stirred 2 hours at room temperature. The solvent was evaporated and the crude product 4-amino-1-[(1R)-1-(aminomethyl)-4-hydroxy-butyl]-3-(4-phenoxyphenyl)imidazo[4,5-c]pyridin-2-one (5) (126 mg, Yield=95.3%) was engaged in the next step.

Step 5: To a flask under argon atmosphere were added 4-amino-1-[(1R)-1-(aminomethyl)-4-hydroxy-butyl]-3-(4-phenoxyphenyl)imidazo[4,5-c]pyridin-2-one (125 mg, 0.29 mmol, 1 eq) (5) and $CH_2Cl_2$ (2 mL). Then, the reaction solution was cooled to 0° C., after charging DIEA (104 μL, 0.59 mmol, 2 eq), and a solution of acryloyl chloride (12.5 μL, 0.15 mmol, 0.5 eq) in $CH_2Cl_2$ (1 mL) was added dropwise. The solution was kept at 0° C. and stirred for 1 hour. The reaction mass was hydrolyzed with $H_2O$ and extracted with AcOEt. The organic phase was separated, dried over $MgSO_4$, filtered and concentrated under vacuum to afford the crude compound which was purified by preparative HPLC to give N-[(2R)-2-[4-amino-2-oxo-3-(4-phenoxyphenyl)imidazo[4,5-c]pyridin-1-yl]-5-hydroxy-pentyl]prop-2-enamide (Compound of Formula V, as referred to above as (6)) (38 mg, Yield=27%, >95% purity). 1H NMR (500 MHz, DMSO-d6) δ ppm 1.25-1.40 (m, 2H), 1.83 (m, 1H), 2.08 (m, 1H), 3.35 (m, 2H), 3.50-3.70 (m, 2H), 4.35 (m, 1H), 4.43 (m, 1H), 4.80 (s, 2H), 5.53 (dd, J=8, 2 Hz, 1H), 6.03 (dd, J=17, 2 Hz, 1H), 6.11 (dd, J=17, 8 Hz, 1H), 6.70 (m, 1H), 7.15 (d, J=8 Hz, 4H), 7.22 (t, J=7 Hz, 1H), 7.43 (d, J=7 Hz, 2H), 7.48 (t, J=7 Hz, 2H), 7.74 (d, J=5 Hz, 1H), 8.29 (t, J=6 Hz, 1H) LC/MS: 474.1 (M+H)+.

Example 5. BTK(h) Study

Compounds of Formula Ib, Formula II, and Formula III were tested against BTK(h) as described herein. All compounds tested were prepared to a working stock of 50× final assay concentration in 100% DMSO. Where appropriate, more concentrated stocks were diluted manually to 50× using 100% DMSO. Compounds, which were powders, were reconstituted to a 10 mM stock in 100% DMSO before further dilution to 50×.

Assay Procedure:

The required volume of the 50× stock of test compound was added to the assay well before a reaction mix containing the enzyme and substrate was added. The reaction was initiated by the addition of ATP at the selected concentration. There was no pre-incubation of the compound with the enzyme/substrate mix prior to ATP addition.

Data Analysis:

Results are expressed as kinase activity remaining, as a percentage of the DMSO control. This is calculated using the following formula:

$$\frac{\text{Mean of Sample Counts} - \text{Mean of Blank Counts}}{\text{Mean of Control Counts}}$$

For $IC_{50}$ determinations, data are analyzed using XLFit version 5.3 (ID Business Solutions). Sigmoidal dose-response (variable slope) curves are fit based on the mean result for each test concentration using non-linear regression analysis. Where the top and/or bottom of the curve fall >10% out with 100 and 0, respectively, either or both of these limits may be constrained at 100 and 0, provided that the QC criterion on $R^2$ is met.

Results are as shown in Table 2.

TABLE 2

| Compound | $IC_{50}$ (nM) |
|---|---|
| Formula Ib | 34 |
| Formula II | 279 |
| Formula III | 1375 |

Example 6. In Vitro Studies

Compounds of Formula Ia, Formula Ib, Formula III, Formula IV, and Formula V were tested in various in vitro assays. Compound binding was calculated as a % inhibition of the binding of a radioactively labeled ligand specific for each target. Compound enzyme inhibition effect was calculated as a % inhibition of control enzyme activity. Certain compounds showed significant activity, which was defined in this instance as an inhibition or stimulation higher than 50%, in certain assays.

BZD Binding Assay:

The general procedure is noted below. See Le Fur, G. et al. (1983), *Life Sci.,* 33: 449-457. Kd is affinity of the radioligand for the receptor. Minor variations to the experimental protocol described below may have occurred during the testing, but if so, they had no impact on the quality of the results obtained.

| Receptor | Source | Ligand | Conc. | Kd | Non specific | Incubation | Detection Method |
|---|---|---|---|---|---|---|---|
| BZD (peripheral) (antagonist radioligand) | Rat Heart | [$^3$H]PK 11195 | 0.2 nM | 1.8 nM | PK 11195 (10 μM) | 15 min RT | Scintillation counting |

The compound of Formula Ia showed significant activity in this assay, exhibiting 52.2% inhibition.

Dopamine Binding Assay:

The general procedure is noted below. See Pristupa, Z. B. et al. (1994), *Mol. Pharmacol.,* 45: 125-135. Minor variations to the experimental protocol described below may have occurred during the testing, but if so, they had no impact on the quality of the results obtained.

| Receptor | Source | Ligand | Conc. | Kd | Non specific | Incubation | Detection Method |
|---|---|---|---|---|---|---|---|
| Dopamine transporter (h) (antagonist radioligand) | Human recombinant (CHO cells) | [$^3$H]BTCP 11195 | 4 nM | 4.5 nM | BTCP (10 μM) | 120 min 4° C. | Scintillation counting |

The compound of Formula Ia showed significant activity in this assay, exhibiting 65% inhibition. The compound of Formula III also showed significant activity, exhibiting 96.2% inhibition.

$D_1$ (b) Binding Assay:

The general procedure is noted below. See Zhou, Q. Y. et al. (1990), *Nature,* 347: 76-80. Minor variations to the experimental protocol described below may have occurred during the testing but if so, they had no impact on the quality of the results obtained.

| Receptor | Source | Ligand | Conc. | Kd | Non specific | Incubation | Detection Method |
|---|---|---|---|---|---|---|---|
| $D_1$ (h) (antagonist radioligand) | Human recombinant (CHO cells) | [$^3$H]SCH 23390 | 0.3 nM | 0.2 nM | SCH 23390 (1 μM) | 60 min RT | Scintillation counting |

The compound of Formula III showed significant activity in this assay, exhibiting 80% inhibition.

$H_2$ (b) Binding Assay: The general procedure is noted below. See Leurs, R. et al. (1994), *Brit. J. Pharmacol.,* 112: 847-854. Minor variations to the experimental protocol described below may have occurred during the testing but if so, they had no impact on the quality of the results obtained.

| Receptor | Source | Ligand | Conc. | Kd | Non specific | Incubation | Detection Method |
|---|---|---|---|---|---|---|---|
| $H_2$ (h) (antagonist radioligand) | Human recombinant (CHO cells) | $[^{125}I]$APT | 0.075 nM | 2.9 nM | tiotidine (100 μM) | 120 min RT | Scintillation counting |

The compound of Formula III showed significant activity in this assay, exhibiting 56.7% inhibition.

δ (DOP) (h) Binding Assay:

The general procedure is noted below. See Simonin, F. et al. (1994), *Mol. Pharmacol.,* 46: 1015-1021. Minor variations to the experimental protocol described below may have occurred during the testing but if so, they had no impact on the quality of the results obtained.

| Receptor | Source | Ligand | Conc. | Kd | Non specific | Incubation | Detection Method |
|---|---|---|---|---|---|---|---|
| δ (DOP) (h) (agonist radioligand) | Human recombinant (Chem-1 (RBL) cells) | $[^3H]$ DADLE | 0.5 nM | 0.6 nM | naltrexone (10 μM) | 60 min RT | Scintillation counting |

The compound of Formula III showed significant activity in this assay, exhibiting 56.7% inhibition.

kappa (h) (KOP) Binding Assay:

The general procedure is noted below. See Simonin, F. et al. (1995), *Proc. Natl. Acad. Sci. U.S.A.,* 92: 7006-7010. Minor variations to the experimental protocol described below may have occurred during the testing but if so, they had no impact on the quality of the results obtained.

| Receptor | Source | Ligand | Conc. | Kd | Non specific | Incubation | Detection Method |
|---|---|---|---|---|---|---|---|
| kappa (h) (KOP) (agonist radioligand) | Human recombinant (RBL cells) | $[^3H]$ U69593 | 0.5 nM | 0.6 nM | naloxone (10 μM) | 60 min RT | Scintillation counting |

The compound of Formula III showed significant activity in this assay, exhibiting 54.6% inhibition.

5-$HT_{5a}$ (h) Binding Assay:

The general procedure is noted below. See Rees, S. et al. (1994), *FEBS Lett.,* 355: 242-246. Minor variations to the experimental protocol described below may have occurred during the testing but if so, they had no impact on the quality of the results obtained.

| Receptor | Source | Ligand | Conc. | Kd | Non specific | Incubation | Detection Method |
|---|---|---|---|---|---|---|---|
| 5-$HT_{5a}$ (h) (agonist radioligand) | Human recombinant (HEK-293 cells) | [$^3$H] LSD | 1.5 nM | 1.5 nM | serotonin (100 μM) | 120 min 37° C. | Scintillation counting |

The compound of Formula III showed significant activity in this assay, exhibiting 56.1% inhibition.

Norepinephrine Transporter (h) Binding Assay:

The general procedure is noted below. See Pacholczyk, T. et al. (1991), *Nature,* 350: 350-354. Minor variations to the experimental protocol described below may have occurred during the testing but if so, they had no impact on the quality of the results obtained.

| Receptor | Source | Ligand | Conc. | Kd | Non specific | Incubation | Detection Method |
|---|---|---|---|---|---|---|---|
| Nor-epinephrine transporter (h) (antagonist radioligand) | Human recombinant (CHO cells) | [$^3$H] nisoxetine | 1 nM | 2.9 nM | desipramine (1 μM) | 120 min 4° C. | Scintillation counting |

The compound of Formula III showed significant activity in this assay, exhibiting 66.7% inhibition.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant FIGURE.

What is claimed is:

1. A compound of Formula Ia:

Formula Ia

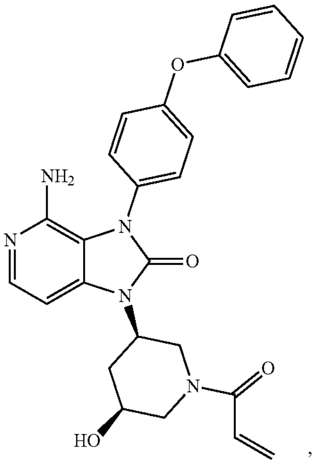

, or a salt thereof, wherein the compound or salt thereof is about 90% pure.

2. The compound of claim 1, wherein the compound or salt thereof is about 95% pure.

3. The compound of claim 1, wherein the compound or salt thereof is about 98% pure.

4. A compound of Formula Ib:

Formula Ib

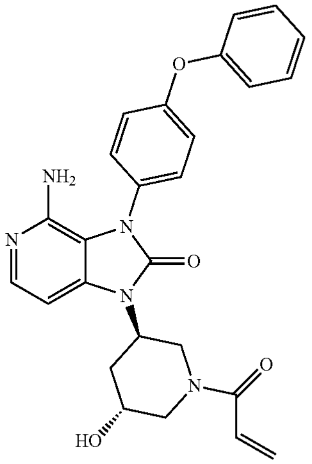

or a salt thereof, wherein the compound or salt thereof is about 90% pure.

5. The compound of claim 4, wherein the compound or salt thereof is about 95% pure.

6. The compound of claim 4, wherein the compound or salt thereof is about 98% pure.

7. The compound of claim 4, the compound or salt thereof is about 99% pure.

8. A compound of Formula II

Formula II

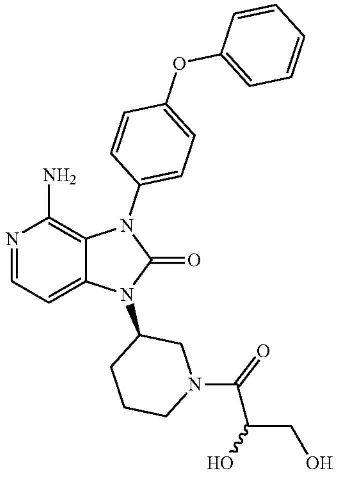

or salt thereof, wherein the compound or salt thereof is about 99.6% pure.

9. The compound of claim 8, wherein the compound is

Formula IIa

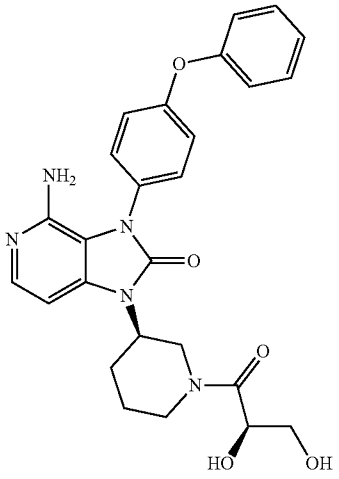

or salt thereof, wherein the compound or salt thereof is about 90% pure.

10. The compound of claim 9, wherein the compound of Formula IIa or salt thereof is about 95% pure.

11. The compound of claim 9, wherein the compound of Formula IIa or salt thereof is about 98% pure.

12. The compound of claim 8, wherein the compound is

Formula IIb

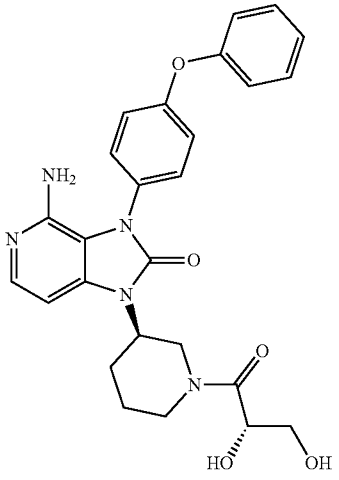

or salt thereof, wherein the compound or salt thereof is about 90% pure.

13. The compound of claim 12, wherein the compound of Formula IIb or salt thereof is about 95% pure.

14. The compound of claim 12, wherein the compound of Formula IIb or salt thereof is about 98% pure.

15. A composition comprising a pharmaceutically acceptable excipient and at least one compound chosen from:

Formula Ia

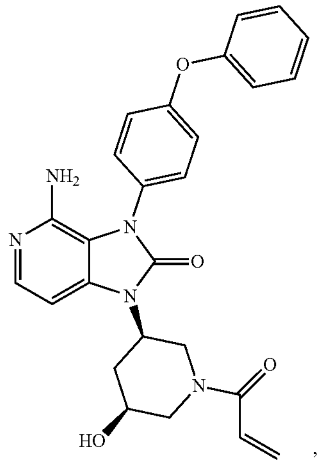

,

Formula Ib

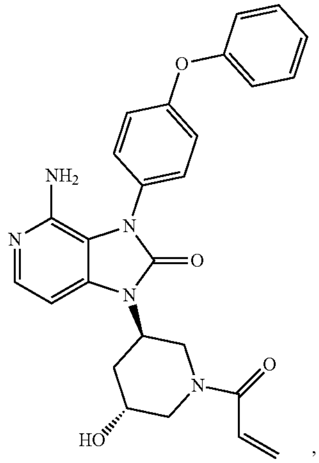

,

Formula II

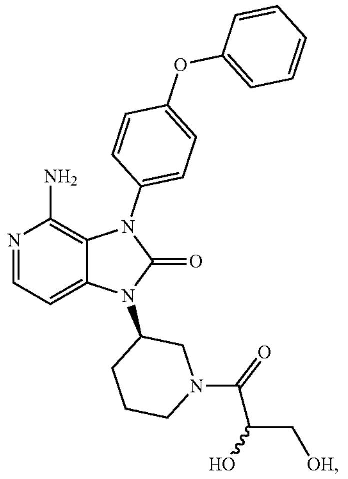

and

-continued

Formula III

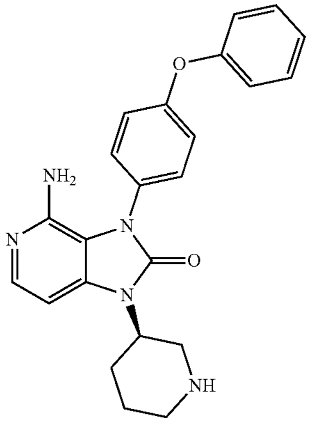

or salts thereof.

16. The composition of claim 15, wherein at least one compound is a compound of Formula Ia or a salt thereof, and wherein the compound of Formula Ia or a salt thereof is at least about 98% pure.

17. The composition of claim 15, wherein at least one compound is a compound of Formula Ib or a salt thereof, and wherein the compound of Formula Ib or salt thereof is at least about 99% pure.

18. The composition of claim 15, wherein the composition is in the form of a capsule, tablet, or pill.

19. A method of preparing the compound of Formula Ia of claim 1 or salt thereof, Formula Ia

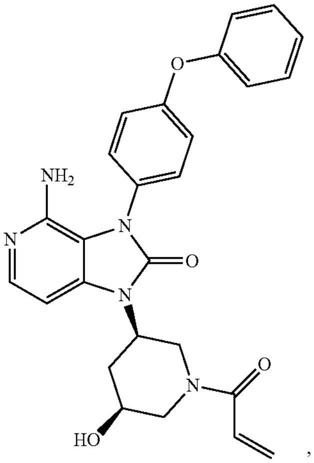

, the method comprising reacting a compound of Formula VIa

Formula VIa

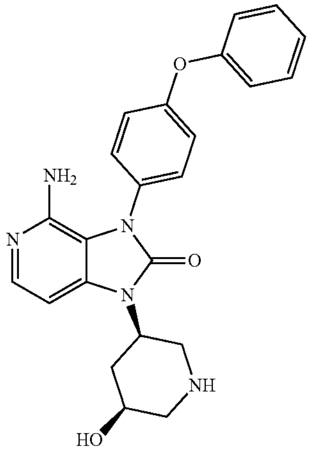

with acryloyl chloride.

20. The method of claim 19, wherein the method further comprises preparing a compound of Formula VIa from a compound of Formula IX Formula IX

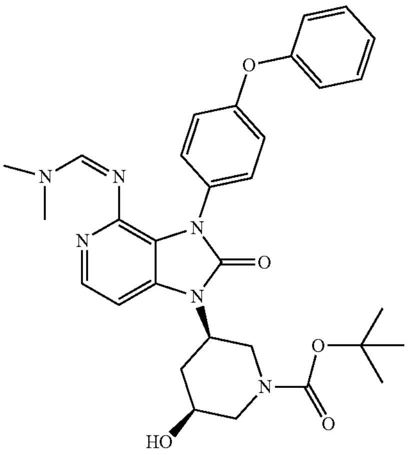

by acid-based deprotection.

21. A method of preparing the compound of Formula Ib of claim 4 or salt thereof, Formula Ib

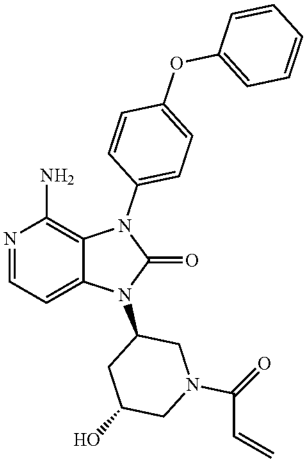

the method comprising reacting a compound of Formula VIb

Formula VIb

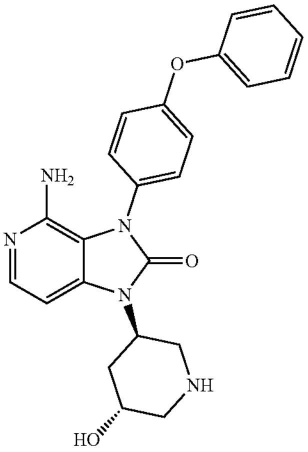

with acryloyl chloride.

22. The method of claim 21, wherein the method further comprises preparing a compound of Formula VIb from a compound of Formula VII Formula VII

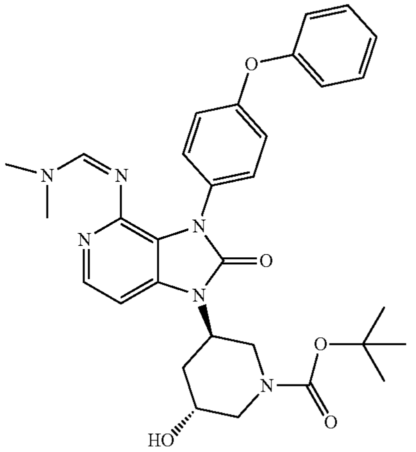

by acid-based deprotection.

23. The method of claim 22, wherein the method further comprises preparing a compound of Formula VII from a compound of Formula VIII Formula VIII

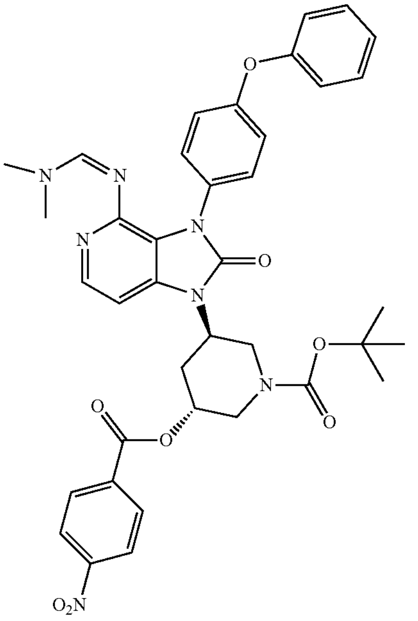

by deprotection using a base.

24. The method of claim 23, wherein the method further comprises preparing a compound of Formula VIII from a compound of Formula IX Formula IX

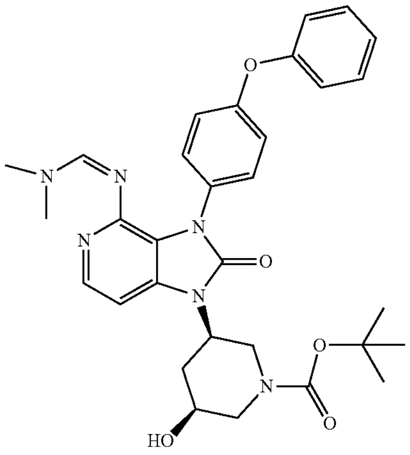

with triphenylphosphine and an azodicarboxylate.

25. The method of claim 24, wherein the azodicarboxylate is chosen from diethyl azodicarboxylate and diisopropyl azodicarboxylate.

26. The composition of claim 15, wherein at least one compound is a compound of Formula Ia or a salt thereof.

27. The composition of claim 15, wherein at least one compound is a compound of Formula Ib or a salt thereof.

28. The composition of claim 15, wherein at least one compound is a compound of Formula II or a salt thereof.

29. The composition of claim 15, wherein at least one compound is a compound of Formula III or a salt thereof.

* * * * *